US012778792B2

(12) United States Patent
Ghuge

(10) Patent No.: US 12,778,792 B2
(45) Date of Patent: Nov. 3, 2026

(54) MAXILLARY AND MANDIBULAR DEVICES THAT INCREASE THE SMALLEST CONCENTRIC AIRWAY CROSS-SECTIONAL AREA OF A USER FOR IMPROVEMENTS DURING PHYSICAL ACTIVITIES

(71) Applicant: Sleep Solutions of Texas, LLC, Tyler, TX (US)

(72) Inventor: Raghavendra Vitthalrao Ghuge, Tyler, TX (US)

(73) Assignee: SLEEP SOLUTIONS OF TEXAS, LLC, Tyler, TX (US)

( * ) Notice: Subject to any disclaimer, the term of this patent is extended or adjusted under 35 U.S.C. 154(b) by 0 days.

(21) Appl. No.: 19/392,810

(22) Filed: Nov. 18, 2025

(65) Prior Publication Data

US 2026/0130787 A1 May 14, 2026

Related U.S. Application Data

(63) Continuation of application No. 18/466,365, filed on Sep. 13, 2023, now Pat. No. 12,485,036, which is a (Continued)

(51) Int. Cl.
*A61F 5/56* (2006.01)
*A63B 71/08* (2006.01)

(52) U.S. Cl.
CPC ............ *A61F 5/566* (2013.01); *A63B 71/085* (2013.01); *A61F 2005/563* (2013.01)

(58) Field of Classification Search
CPC ..... A61B 5/1072; A61B 5/1076; A61B 5/481; A61B 5/4812; A61B 5/4818; A61B 5/4557; A61B 5/14552; A61B 5/682; A61B 5/746; A61B 5/296; A61B 5/297; A61B 5/01; A61B 5/4542; A61B 5/097; A61B 17/8071; A61B 2560/0214; A61B 2560/0219; A61B 71/085; A61B 71/2562; A61B 71/0247; A61B 71/0271; A63B 2071/086; A63B 71/085; A61F 2002/30991; A61F 2/2803; A61F 5/56; A61F 5/566; A61F 2005/563;
(Continued)

(56) References Cited

U.S. PATENT DOCUMENTS

2018/0078343 A1* 3/2018 Falkel ................. A61F 5/05891
2020/0121493 A1* 4/2020 Yukita ..................... A61F 5/566

* cited by examiner

*Primary Examiner* — Ophelia A Hawthorne
*Assistant Examiner* — Michael Milo
(74) *Attorney, Agent, or Firm* — FisherBroyles, LLP; Susan M. Oiler

(57) ABSTRACT

Mandibular repositioning devices have a maxillary piece with a right side backmost teeth mold and/or left side backmost teeth mold and a driver flange having an anterior side with a convex curvature protruding from one or both thereof. The devices have a mandibular piece with a protrusive flange extending cranially therefrom positioned to have a posterior side engaged with the anterior side of each driver flange and with a plateau of a preselected height between the base of the protrusive flange and the tooth covering. The posterior side of each protrusive flange has a concave-to-convex curvature from a base of the protrusive flange toward a most cranial point of the protrusive flange and a convex portion of the concave-to convex curvature engages the convex curvature of the driver flange in a rest position. The plateau prevents disconnect between each protrusive flange and a respective driver flange.

20 Claims, 40 Drawing Sheets

Related U.S. Application Data continuation of application No. 17/366,649, filed on Jul. 2, 2021, now Pat. No. 11,806,273.

(58) Field of Classification Search
CPC ......... A61C 19/045; A61C 11/00; A61C 7/08; A61C 7/36; A61C 9/0006; Y10S 602/902
USPC .......................................................... 128/848
See application file for complete search history.

FIG. 30

COMBINED EFFECT OF ANTERIOR AND VERTICAL ADVANCEMENT OF MANDIBLE (TAVMLRD)

| PLATEAU HEIGHT | MOUTH OPENING* | | ANTERIOR MOVEMENT IN THE AT REST POSITION | | | | | | | |
|---|---|---|---|---|---|---|---|---|---|---|
| (mm) | (degrees) | (mm) | 0 mm | 1 mm | 2 mm | 3 mm | 4 mm | 5 mm | 6 mm | |
| 1.06 | 1 | 1.66 | 1.25 | 2.25 | 3.25 | 4.25 | 5.25 | 6.25 | 7.25 | AREA 0 |
| 2.12 | 2 | 3.31 | 2.50 | 3.50 | 4.50 | 5.50 | 6.50 | **7.50** | **8.50** | **AREA 1** |
| 3.18 | 3 | 4.97 | 3.75 | 4.75 | 5.75 | 6.75 | 7.75 | 8.75 | 9.75 | AREA 2 |
| 4.24 | 4 | 6.62 | 5.00 | 6.00 | 7.00 | 8.00 | 9.00 | 10.00 | 11.00 | AREA 3 |
| 5.3 | 5 | 8.28 | 6.25 | 7.25 | 8.25 | 9.25 | 10.25 | 11.25 | 12.25 | |
| 6.36 | 6 | 9.93 | 7.50 | 8.50 | 9.50 | 10.50 | 11.50 | 12.50 | 13.50 | |
| 7.42 | 7 | 11.59 | 8.75 | 9.75 | 10.75 | 11.75 | 12.75 | 13.75 | 14.75 | AREA 4 |
| 8.48 | 8 | 13.24 | 10.00 | 11.00 | 12.00 | 13.00 | 14.00 | 15.00 | 16.00 | |
| 9.54 | 9 | 14.90 | 11.25 | 12.25 | 13.25 | 14.25 | 15.25 | 16.25 | 17.25 | |
| 10.6 | 10 | 16.55 | 12.50 | 13.50 | 14.50 | 15.50 | 16.50 | 17.50 | 18.50 | AREA 5 |
| 11.66 | 11 | 18.21 | 13.75 | 14.75 | 15.75 | 16.75 | 17.75 | 18.75 | 19.75 | |
| 12.72 | 12 | 19.86 | 15.00 | 16.00 | 17.00 | 18.00 | 19.00 | 20.00 | 21.00 | |
| 13.78 | 13 | 21.52 | 16.25 | 17.25 | 18.25 | 19.25 | 20.25 | 21.25 | 22.25 | |
| 14.84 | 14 | 23.17 | 17.50 | 18.50 | 19.50 | 20.50 | 21.50 | 22.50 | 23.50 | |
| 15.9 | 15 | 24.83 | 18.75 | 19.75 | 20.75 | 21.75 | 22.75 | 23.75 | 24.75 | |
| 16.96 | 16 | 26.48 | 20.00 | 21.00 | 22.00 | 23.00 | 24.00 | 25.00 | 26.00 | |
| 18.02 | 17 | 28.14 | 21.25 | 22.25 | 23.25 | 24.25 | 25.25 | 26.25 | 27.25 | |
| 19.08 | 18 | 29.79 | 22.50 | 23.50 | 24.50 | 25.50 | 26.50 | 27.50 | 28.50 | |
| 20.14 | 19 | 31.45 | 23.75 | 24.75 | 25.75 | 26.75 | 27.75 | 28.75 | **29.75** | AREA 6 |
| 21.2 | 20 | 33.10 | 25.00 | 26.00 | 27.00 | 28.00 | 29.00 | **30.00** | **31.00** | |
| 22.26 | 21 | 34.76 | 26.25 | 27.25 | 28.25 | **29.25** | **30.25** | **31.25** | **32.25** | |
| 23.32 | 22 | 36.41 | 27.50 | 28.50 | **29.50** | **30.50** | **31.50** | **32.50** | **33.50** | |
| 24.38 | 23 | 38.07 | 28.75 | **29.75** | **30.75** | **31.75** | **32.75** | **33.75** | **34.75** | |

*ϕ2 = 42 MM = Radius of trailing superior curvature of the protrusive flange as labeled in FIG. 21

FIG. 31

THEORETICAL
POST-TREATMENT AIRWAY DMENSIONS AND OXYGENATION IN MILD/MODERATE OSA USING
FIXED 2-3 MM VERTICAL AND 5-6 MM ANTERIOR MANDIBULAR ADVANCEMENT (Area 1)

| | PRE-TREATMENT | | POST-TREATMENT | | ABSOLUTE CHANGE | | PERCENTAGE CHANGE | |
|---|---|---|---|---|---|---|---|---|
| PARAMETER | MEAN | SD | MEAN | SD | MEAN | SD | MEAN | SD |
| EPWORTH Sleepiness Scale | 18.54 | 3.17 | 5.21 | 1.51 | -13.33 | 3.3 | -71.90% | 21.47% |
| Oxygen Saturation ( %) | 87.97 | 4.43 | 94.89 | 1.54 | 6.92 | 4.3 | 7.87% | 5.15% |
| Airway Volume ($mm^3$) | 12140 | 4773.9 | 14500 | 5114.6 | 2360 | 5.3 | 19.44% | 0.07% |
| SMCA of Upper Airway (mm) | 81.95 | 55.23 | 128.5 | 54.78 | 46.55 | 6.3 | 56.80% | 23.58% |
| Anterior-posterior-SMCA (mm) | 4.9 | 1.65 | 8.01 | 2.04 | 3.11 | 7.3 | 63.47% | 224.62% |
| Transverse-SMCA (mm) | 27.67 | 8.52 | 31.94 | 8.59 | 4.27 | 8.3 | 15.43% | 43.34% |

FIG. 32

ACTUAL
POST-TREATMENT DATE AND OXYGENATION IN SEVERE OSA USING
0 mm Anterior Advancement at Rest, 23 mm Vertical advancement, a 17.5 mm combined Effect

| PARAMETER | Pre-Treatment | BIPAP | AVMLRD | BIPAP Effect | AVMLRD Effect | \|AVMLRD over BIPAP\| |
|---|---|---|---|---|---|---|
| Total Sleep Time (min) | 360 | 365 | 465 | 1.4% | 22.6% | 21.5% |
| Apnea Hypopnea Index | 32 | 6.3 | 4.8 | -407.9% | -566.7% | 31.3% |
| Respiratory Disturb Index | 37 | 12.9 | 8.6 | -186.8% | -330.2% | 50% |
| Oxygen Saturation (%) | 76 | 84 | 88 | 9.5% | 13.6% | 4.5% |
| REM Sleep (%) | 12.5 | 8.48 | 25.37 | -47.4% | 50.7% | 66.6% |
| Sleep Efficiency (%) | 76.5 | 78.44 | 88.74 | 2.5% | 13.8% | 11.6% |
| Deep Sleep (%) | 10.5 | 15.59 | 16.96 | 32.6% | 38.1% | 8.1% |

FIG. 57

PREDICTIVE ALOGITHMN FOR CALCULATING
TAVMLR, REHYDRATION QUANTITY, AND CARDIO-PULMONARY BIOMETRIC PARAMETERS

| INPUTS | | | | | | |
|---|---|---|---|---|---|---|
| **Age (years)** | **Target HR (THR)** | **Baseline HR (BHR)** | **Baseline Respiratory Rate (BRR)** | **Baseline Core Body Temp. (BT) (°F)** | **Baseline Minute Ventilation (BMV)** | **Baseline Air Pressure (BAP) ($N/m^2L$)** |
| [INPUT] | [INPUT] | [INPUT] | [INPUT] | [INPUT] | [INPUT] | [INPUT] |
| **OUTPUTS** | | | | | | |
| **Peak HR for Age (PHR)** | **% Peak HR** | **Change in HR** | **Airflow Resistance (AR)** | **Airway Radius $R_a$ (mm)*** | **Target Respiratory Rate (RR)** | **Target Minute Ventilation (TMV)** |
| 220-Age | BHR/PHR*100 | (THR - BHR)/BHR | (THR – BHR) / (BAP*100) | $(8*(V_a)*L_{airway})$ / $AR^{1/4}$ | THR/5 | RR*0.5 |
| **Target Air Pressure (TAP)** | **Work of Breathing** | **Target Core Body Temp. (TT) (°F)** | **Dehydration per hr (ml)** | **SMCA** | | **TAVMLR** |
| (TMV-BMV/TMV) +BAP | TMV*TAP* 0.01 | BT + (THR – BHR) *0.1 | ((RR-BRR)*0.5*BMV*1.1) + ((TT-BT)*0.5*BMV*1.1) | $3.142*R_a^2$ | | (0.1839 * SMCA) – 1.1643 |

HR = Heartrate
BP = Blood Pressure
Viscosity of air ($V_a$) = 1.81
$L_{airway}$ = 10 cm

FIG. 58

PREDICTIVE ALOGITHMN FOR CALCULATING
TAVMLR, REHYDRATION QUANTITY, AND CARDIO-PULMONARY BIOMETRIC PARAMETERS

| **INPUTS** | | | | | | |
|---|---|---|---|---|---|---|
| **Age (years)** | **Target HR (THR)** | **Baseline HR (BHR)** | **Baseline Respiratory Rate (BRR)** | **Baseline Core Body Temp. (BT) (°F)** | **Baseline Minute Ventilation (BMV)** | **Baseline Air Pressure (BAP) (N/m$^2$L)** |
| 24 | 120 | 60 | 12 | 98.4 | 6 | 1.2 |
| **OUTPUTS** | | | | | | |
| **Peak HR for Age (PHR)** | **% Peak HR** | **Change in HR** | **Airflow Resistance (AR)** | **Airway Radius $R_a$ (mm)*** | **Target Respiratory Rate (RR)** | **Target Minute Ventilation (TMV)** |
| 196 | 61 | 200% | 0.5000 | 4.13 | 1.70 | 12 |
| **Target Air Pressure (TAP)** | **Work of Breathing** | **Target Core Body Temp. (TT) (°F)** | **Dehydration per hr (ml)** | **SMCA for exercise** | | **TAVMLR** |
| 1.70 | 20% | 110.4 | 550 | 53.47 | | 8.7 |

FIG. 59

PREDICTIVE ALGORITHM II: TAVMLR, REHYDRATION RECOMMENDATION AND CARDIO-PULMONARY BIOMETRIC PARAMETERS

| | D | E | F | G | H | I | J | K | L |
|---|---|---|---|---|---|---|---|---|---|
| | TARGET EXERCISE HR | RESTING HR | ACTUAL EXERCISE HR | AGE | BODY WEIGHT (lbs) | HEIGHT (in) | RESTING SYSTOLIC BP | RESTING DIASTOLIC BP | RESTING CORE TEMP (·F) |
| | [INPUT] | [INPUT] | [INPUT] | [INPUT] | [INPUT] | [INPUT] | [INPUT] | [INPUT] | [INPUT] |
| | TARGET % PEAK HR | ACTUAL % PEAK HR | PEAK HR FOR AGE | PREDICTED PEAK SBP | PRED. PEAK DBP | DOUBLE PRODUCT DP | BMI | DEHYD/HOUR (ml/hr) | EXERCISE BODY TEMP (·F) |
| 29 | =D27/F29 | =F27/F29 | =(220-G27) | =1.2*J27 | =1.2*K27 | =G29*D27 | $=((H27)/((I27)^2))*703$ | =(((D33-L31)*22.917)+((L29-L27)*22.917)) | =L27+((D27-E27)*0.1) |
| | TARGET TAVMLR | TARGET SMCA | ACTUAL PRED SMCA | TARGET AF RESIST | ACTUAL AF RESIST | TARGET RADIUS (mm) | ACTUAL RADIUS (mm) | RESTING MIN VENT | RESTING RR |
| 31 | =(-1.1643)+(0.1839*E31) | $=3.142*(I31^2)$ | $=3.142*(J31^2)$ | =(D27-E27)/(1.2*100) | =(F27-E27)/(1.2*100) | $=((8*1.81*10)/(G31))^{1/4}$ | $=((8*1.81*10)/(H31))^{1/4}$ | =L31*0.5 | =E27/5 |
| | TARGET RR | ACTUAL RR | TARGET MIN VENT | ACTUAL MIN VENT | TARGET WORK BREATH | ACT WORK OF BREAT | TARGET AIR PRESSURE (atm) | ACTUAL AIR PRESSURE (atm) | RESTING PRESSURE (atm) |
| 33 | =D27/5 | =F27/5 | =0.5*D33 | =E33*0.5 | =F33*J33*0.01 | =G33*K33*0.01 | =(D33-L31)/D33+L33 | =((E33-L31)/E33)+L33 | =1+(L31/80) |

| | | | | | | | | |
|---|---|---|---|---|---|---|---|---|
| TARGET EXERCISE HR | RESTING HR | ACTUAL EXERCISE HR | AGE | BODY WEIGHT (lbs) | HEIGHT (in) | RESTING SYSTOLIC BP | RESTING DIASTOLIC BP | RESTING CORE TEMP (·F) |
| 120 | 60 | 137 | 56 | 185 | 67 | 120 | 80 | 98.4 |
| TARGET % PEAK HR | ACTUAL % PEAK HR | PEAK HR FOR AGE | PREDICTED PEAK SBP | PRED. PEAK DBP | DOUBLE PRODUCT DP | BMI | DEHYD/HOUR (mL/hr) | EXERCISE BODY TEMP (·F) |
| 73% | 84% | 164 | 144 | 96 | 17280 | 28.97 | 412.51 | 104.4 |
| TARGET TAVMLR | TARGET SMCA | ACTUAL PRED SMCA | TARGET AF RESIST | ACTUAL AF RESIST | TARGET RADIUS (mm) | ACTUAL RADIUS (mm) | RESTING MIN VENT | RESTING RR |
| 53.47 | 53.47 | 47.20 | 0.50 | 0.6417 | 0.50 | 3.88 | 6 | 12 |
| TARGET RR | ACTUAL RR | TARGET MIN VENT | ACTUAL MIN VENT | TARGET WORK BREATH | ACT WORK OF BREAT | TARGET AIR PRESSURE (atm) | ACTUAL AIR PRESSURE (atm) | RESTING PRESSURE (atm) |
| 24 | 27.4 | 12 | 13.7 | 20% | 23% | 1.65 | 1.71 | 1.15 |

FIG. 60

WORKING EXAMPLE 2
PREDICTIVE ALOGITHMN I

| | | | | | | |
|---|---|---|---|---|---|---|
| Age (years) | Target HR (THR) | Baseline HR (BHR) | Baseline Respiratory Rate (BRR) | Baseline Core Body Temp. (BT) (˚F) | Baseline Minute Ventilation (BMV) | Baseline Air Pressure (BAP) |
| 56 | 117 | 60 | 12 | 98.4 | 12 | 1.69 |
| Peak HR for Age (PHR) | % Peak HR | Change in HR | Airflow Resistance (AR) | Airway Radius ($R_a$) (mm)* | Target Respiratory Rate (RR) | Target Minute Ventilation (TMV) |
| 164 | 71 | 195% | 0.475 | 4.17 | 23 | 12 |
| Target Air Pressure (TAP) | Work of Breathing | Target Core Body Temp. (TT) (˚F) | Dehydration (ml/hr) | SMCA for exercise | | TAVMLR |
| 1.66 | 20% | 110.1 | 529.38 | 54.86 | | 8.9 |

ALGORITHM II
Weight 185 lbs

| | | | | | | | | |
|---|---|---|---|---|---|---|---|---|
| TARGET EXERCISE HR | RESTING HR | ACTUAL EXERCISE HR | AGE | BODY WEIGHT (lbs) | HEIGHT (in) | RESTING SYSTOLIC BP | RESTING DIASTOLIC BP | RESTING CORE TEMP (◦F) |
| 117 | 60 | 137 | 56 | 185 | 67 | 120 | 80 | 98.4 |
| TARGET % PEAK HR | ACTUAL % PEAK HR | PEAK HR FOR AGE | PREDICTED PEAK SBP | PRED. PEAK DBP | DOUBLE PRODUCT DP | BMI | DEHYD/HOUR (mL/hr) | EXERCISE BODY TEMP (◦F) |
| 71% | 84% | 164 | 144 | 96 | 16848 | 28.97 | 391.88 | 104.1 |
| TARGET TAVMLR | TARGET SMCA | ACTUAL PRED SMCA | TARGET AF RESIST | ACTUAL AF RESIST | TARGET RADIUS (mm) | ACTUAL RADIUS (mm) | RESTING MIN VENT | RESTING RR |
| 9 | 54.86 | 47.20 | 0.4750 | 0.6417 | 4.18 | 3.88 | 6 | 12 |
| TARGET RR | ACTUAL RR | TARGET MIN VENT | ACTUAL MIN VENT | TARGET WORK BREATH | ACT WORK OF BREAT | TARGET AIR PRESSURE (atm) | ACTUAL AIR PRESSURE (atm) | RESTING PRESSURE (atm) |
| 23 | 27.4 | 12 | 13.7 | 19% | 23% | 1.64 | 1.71 | 1.15 |

FIG. 61

ALGORITHM II
Weight 200 lbs

| | | | | | | | | |
|---|---|---|---|---|---|---|---|---|
| TARGET EXERCISE HR | RESTING HR | ACTUAL EXERCISE HR | AGE | BODY WEIGHT (lbs) | HEIGHT (in) | RESTING SYSTOLIC BP | RESTING DIASTOLIC BP | RESTING CORE TEMP (°F) |
| 100 | 60 | 137 | 56 | 200 | 67 | 160 | 90 | 98.4 |
| TARGET % PEAK HR | ACTUAL % PEAK HR | PEAK HR FOR AGE | PREDICTED PEAK SBP | PRED. PEAK DBP | DOUBLE PRODUCT DP | BMI | DEHYD/HOUR (mL/hr) | EXERCISE BODY TEMP (°F) |
| 61% | 84% | 164 | 192 | 108 | 19200 | 31.32 | 275 | 102.4 |
| TARGET TAVMLR | TARGET SMCA | ACTUAL PRED SMCA | TARGET AF RESIST | ACTUAL AF RESIST | TARGET RADIUS (mm) | ACTUAL RADIUS (mm) | RESTING MIN VENT | RESTING RR |
| 11 | 65.49 | 47.20 | 0.3333 | 0.6417 | 4.57 | 3.88 | 6 | 12 |
| TARGET RR | ACTUAL RR | TARGET MIN VENT | ACTUAL MIN VENT | TARGET WORK BREATH | ACT WORK OF BREAT | TARGET AIR PRESSURE (atm) | ACTUAL AIR PRESSURE (atm) | RESTING PRESSURE (atm) |
| 20 | 27.4 | 1o | 13.7 | 16% | 23% | 1.55 | 1.71 | 1.15 |

MAXILLARY AND MANDIBULAR DEVICES THAT INCREASE THE SMALLEST CONCENTRIC AIRWAY CROSS-SECTIONAL AREA OF A USER FOR IMPROVEMENTS DURING PHYSICAL ACTIVITIES

RELATED APPLICATIONS

This application is a continuation of U.S. application Ser. No. 18/466,365, filed Sep. 13, 2023, which is a continuation of U.S. application Ser. No. 17/366,649, filed Jul. 2, 2021, the entirety of which is incorporated herein by reference.

TECHNICAL FIELD

This application relates to maxillary and mandibular devices, referred to as mandibular repositioning devices, and methods of improving performance including heart rate during physical activity, more particularly, to a mandibular repositioning device having a protrusive flange on the mandibular piece in operative communication with a driver flange on the maxillary piece.

BACKGROUND

Many individuals suffer from disordered breathing while asleep and many more have significant narrowing at the level of the smallest concentric airway cross-sectional area (SMCA) size while awake when studied by cone CT scans. Some example disorders associated with reduced SMCA include obstructive sleep apnea (OSA), snoring, snore arousals, sleep-related hypoxia, and other conditions dependent on and caused by snoring or OSA. OSA is a condition in which sleep is repeatedly interrupted by an inability to breathe, which is typically a results of intermittent obstruction of the airway by the tongue and a general relaxation of the muscles which stabilize the upper airway segment, which can cause a lack of oxygen, snoring, cardiovascular and neurological complications, such as sleep-induced hypertension, heart attacks, cardiac arrythmias, strokes, Alzheimer's disease, hypertension, sleep-induced hypertension, diabetes, weight gain, and depression. The maximum heart rate that human being is able to attain during physical activity is often given by a formula that is equal to 220 minus the age of the individual (in years). A desired heart rate during exercise for burning fat is found to be in the range of 60% to 70% of the maximum heart rate and while the desired hear rate for cardio activity is 70% to 80% of the maximum heart rate. People with a narrowing of their SMCA will often find themselves breathing much harder during exercise and thus may generate a higher heart rate that is greater than the 60% to 70% range; thus, moving more quickly from the fat burning rate to a cardio rate (70% to 80% range), which may not be desired. These observations are important because the windows for these two exercise goals (fat burning and cardio) are narrow and adjacent to each other, and an individual can very easily be in cardio range while desiring to be in fat burning range.

The SMCA on average is about 149 $mm^2$. This is the narrowest point in an adult human airway. Many humans have much smaller airways as shown by cone CT scans of the airway. It has been observed that OSA patients have an SMCA on average of about 40 $mm^2$-67 $mm^2$. In OSA, the mandible lowers to a greater degree than in normal sleep due to activation of the upper airway muscles (due to lack of oxygen) allowing traction on hyoid bone and mouth opening to facilitate mouth breathing. However, this lowering of the mandible comes at a price of reducing the antero-posterior diameter of the airway due to posterior movement of the mandible and tongue in the second half of the lowering process (the second 13°). Anterior (sagittal) repositioning of the mandible alone does not counteract this part of physiology. Studies have shown that vertical (caudal) repositioning of the mandible has a greater influence on increasing the transverse diameter of the SMCA than anterior repositioning. Moreover, applicant believes that simultaneously advancing the mandible sagittally while advancing it caudally can mitigate airway narrowing that occurs during voluntary mouth opening in OSA. Both such repositionings increase the AP diameter and transverse diameter of the SMCA simultaneously. These simultaneous increase in AP and transverse diameters effectively incrementally increase the SMCA.

Mandibular repositioning devices have been FDA-approved and used as a treatment for sleep apnea when treatment by a CPAP (Continuous Positive Airway Pressure) machine has been ineffective for the particular patient, or when a patient is unable to tolerate a PAP (Positive Airway Pressure) device, but not for use while awake. Regardless of use while awake or asleep, a mandibular repositioning device, as with all mouthpieces, can trigger saliva production, i.e., an autonomic nervous system response. The parotid, submandibular, and sublingual salivary glands are the three main saliva producing glands in the human oral cavity. Saliva functions to lubricate and mechanically/enzymatically digest food and assist in vocalization, swallowing, and breathing. Too little saliva can cause difficulties with these functions, and too much saliva can interfere with these functions.

The parotid salivary gland is located in the upper part of the cheek and it drains on the inside of the cheek besides the maxillary molar teeth. The saliva circles around the teeth and flows from back to front and drips down onto the teeth and down onto the tongue. The tongue then laps it back over the palate and then reflex swallowing takes place. The submandibular glands reside under the mandible and drain behind the lower mandibular incisors. The sublingual glands reside beneath the tongue and drain onto the floor of the mouth under the tongue. The tongue moves the saliva from the sublingual gland forward under the tongue and combines it with the submandibular saliva and then moves this saliva up over the inside of the mandibular and maxillary incisors and then laps it back across the palate and back into the oropharynx for swallowing.

An oral appliance of any nature disrupts the channels of natural flow of saliva and automatically induces excess saliva production. This overwhelms the system of natural saliva drainage and causes drooling, difficulty speaking or articulating (quite important in team sports like football that requires communicating strategy) and interferes with rhythmic breathing which is extremely essential during performance sports. Also, this phenomenon is a common source of insomnia in oral appliance users, such as those treating OSA or bruxism or those for orthodontic treatment. It is also a source of nocturnal anxiety, disruption of deep sleep or REM sleep and constant evoking of the gag reflex.

There is a need for improvement in mandibular repositioning devices to increase the size of a user's smallest concentric airway cross-sectional area to keep the heart rate lower, which makes breathing easier during physical activity, in particular by moving the mandible forward and downward and moving the tongue forward and one that effectively restores the disrupted natural channels of salivary flow.

SUMMARY

The mandibular repositioning device introduced herein opens a user's airway, especially increasing the size of a user's smallest concentric airway cross-sectional area, for improvement in numerous aspects of performance during physical activity, especially a lower heart rate, and has effective salivary flow through one or more salivary flow channels in one or both of the mandibular piece and maxillary piece. The methods and devices disclosed herein are able to increase the smallest concentric airway cross-sectional area of any human airway, be it small, average, or large at its original size. The methods and devices are able to advance the mandible and tongue of the user anteriorly and caudally to increase the rate of airflow, decrease the work of breathing, and thereby enhance physical performance of the user, fore example, speed, endurance, strength, and accuracy. Individuals with a reduced SMCA will likely see a greater benefit than those with a "normal" SMCA, but both will see benefits.

In all aspects, methods of lowering heart rate during physical activity are disclosed. The methods include identifying a person having a smallest concentric airway cross-sectional area in need of being increased while awake and providing the person with a mandibular repositioning device fitted for their respective mandible and maxilla that has a maxillary piece comprising a tooth covering having a driver flange protruding laterally outward on a right side proximate a backmost teeth mold and/or on a left side proximate a backmost teeth mold and a mandibular piece comprising a tooth covering having a protrusive flange extending cranially therefrom positioned to have a posterior side engaged with the anterior side of each driver flange. Each driver flange having an anterior side with a convex curvature, and each protrusive flange has a posterior side with a concave-to-convex curvature from its base toward its most cranial point and a convex portion of the concave-to convex curvature engages the convex curvature of the driver flange in a rest position. In use, downward movement of the mandibular piece moves the convex portion of the posterior side of the protrusive flange along the convex curvature of the driver flange, thereby moving a user's mandible forward as well. During physical activity, the mandibular repositioning device increases the size of the person's smallest concentric airway cross-sectional area, thereby lowering said person's heart rate. The physical activity can be weight-lifting, sports, a fitness exercise, a weight loss activity, running, flying an aircraft or spacecraft, etc. The heart rate is decreased by at least 10% compared to the same person performing the same physical activity without the mandibular repositioning device.

In one embodiment, the person is over-weight, and the physical activity is a weight loss activity; wherein the method maintains the person's hear rate at a fat burning rate for a longer period of time compared to the same person without the mandibular repositioning device.

In another aspect, the mandibular piece has a plateau of a preselected height between the base of the protrusive flange and the tooth covering. The preselected height of the plateau prevents disconnect between each protrusive flange and its respective driver flange relative to a fully open mouth measurement between incisors of the user. In all embodiments, the plateau can extend across the full width of the tooth covering. In one embodiment, the plateau is wedge-shaped, has a first height at the anterior base of the protrusive flange, a second height at the posterior base of the protrusive flange, and the first height is greater than the second height; and wherein the protrusive flange and driver flange are inclined equivalently to the plateau to maintain the engaged convex portion to convex curvature thereof. Here, the plateau extends posteriorly to a posterior terminus of the tooth covering and terminates with a third height that is smaller than the first height and the second height.

In all aspects, the protrusive flange can be removably replaceably attached to the mandibular piece. In one embodiment, the protrusive flange slides into the tooth covering of the mandibular piece from a rear surface and engagingly saddles the dental crown against cranial movement. Also, the driver flange can be removably replaceably attached to the maxillary piece. In one embodiment, the driver flange comprises a posteriorly extending post receivable in a slot having an anterior opening and being buccally juxtaposed to the backmost teeth mold of the maxillary piece.

In another aspect, the protrusive flange and the driver flange are positioned to place an engagement point of the convex portion of the concave-to convex curvature with the convex curvature of the driver flange at a midpoint length that is at half the lineal distance from a vertical axis at the front of the incisors (incisor vertical axis) to a point on a parallel vertical axis aligned with the temporo-mandibular joint (TMJ) at rest (TMJ vertical axis).

In all aspects, the maxillary piece can have a housing proximate one or both of a left molar portion and a right molar portion, wherein each housing encloses a power source electrically connected to a motor and to an on-board circuit board and has a driver operatively connected to the motor and to the driver flange for anterior and posterior movements of the driver flange and/or cranial and caudal movements of the driver flange. Also, the mandibular piece can have a housing proximate one or both of a left molar portion and a right molar portion and the mandibular device has a laterally inward extending protrusion extending from each housing toward the tongue at a position proximate a lingual muscle of the tongue, wherein each housing of the mandibular piece encloses a power source electrically connected to an on-board circuit board which is in electrical communication with one or more sensors enclosed within the laterally inward extending protrusion, or the maxillary piece has a palate housing portion and/or a buccal housing portion extending from each housing thereof and each palate housing portion and buccal housing portion encloses therein a power source electrically connected to an on-board circuit board which is in electrical communication with one or more sensors. When the mandibular piece houses the one or more sensors, each on-board circuit within housings of the maxillary piece include a receiver and a microprocessor having an instruction stored in nontransitory memory to activate each motor and each on-board circuit board within housings of the mandibular piece include a receiver, a transmitter, and a microprocessor having an instruction in nontransitory memory to activate each motor within housing of the maxillary piece simultaneously based on data received from the one or more sensors, and, when the maxillary piece houses the one or more sensors, each on-board circuit within the housings of the maxillary piece include a microprocessor having an instruction in nontransitory memory to activate each motor simultaneously based on data received from the one or more sensors. When the maxillary piece only has anterior to posterior movement of the driver flange, the mandibular piece has a motor housed within each housing thereof and has a cranial-to-caudal driver operatively connected to each motor; wherein the cranial-to-caudal driver is operatively engaged with the maxillary piece for cranial and caudal adjustment of the device from instructions stored in the nontransitory memory of the on-board circuit board within each housing of the mandibular piece based on data received from the one or more sensors. In one embodiment, one or both of the laterally inward extending protrusion house an electrode operatively connected to the on-board circuit board and the power source of the housing from which laterally inward extending protrusion extends; wherein the on-board circuit board within each housings of the mandibular piece include instructions that based on data from the one or more sensors activates each motor within housing of the maxillary piece and the electrode simultaneously or sequentially as needed to open an airway of a user.

In all aspects, the mandibular piece can have a housing proximate one or both of a left molar portion and a right molar portion and the mandibular device has a laterally inward extending protrusion extending from each housing toward the tongue at a position proximate a lingual muscle of the tongue. Each housing of the mandibular piece encloses a power source electrically connected to an on-board circuit board which is in electrical communication with one or more sensors and with an electrode, and the on-board circuit board within each housings include instructions that based on data from the one or more sensors activates each electrode as needed to open an airway of a user.

In another aspect, the maxillary piece has a housing proximate one or both of a left molar portion and a right molar portion, wherein each housing encloses a power source electrically connected to a motor and to a microprocessor and has a driver operatively connected to a means for moving the driver flange for anterior-posterior movement and cranial-caudal movement. In one embodiment, the means for moving the driver flange comprises a piezo-electric motor and an internal robotic armature positioned for repositioning of the piezo-electric motor as the cranial-caudal movement, or robotic arms connected to integrated plates in the driver flange, or robotic arms connected to separate plates for the independent cranial-caudal movement and anterior-posterior movement of the driver flange. In another embodiment, the microprocessor has a quantum microchiplet and/or a photonic integrated circuit. Position sensors that measure a first distance for cranial-caudal movement and a second distance for anterior-posterior movement of the driver flange can be included in the device.

In another aspect, mandibular repositioning devices are disclosed that have a maxillary piece comprising a tooth covering having a driver flange protruding laterally outward on a right side proximate a backmost teeth mold and/or on a left side proximate a backmost teeth mold and a mandibular piece comprising a tooth covering having a protrusive flange extending cranially therefrom positioned to have a posterior side engaged with the anterior side of each driver flange. Each driver flange has an anterior side with a convex curvature, and each protrusive flange has a posterior side with a concave-to-convex curvature from its base toward its most cranial point and a convex portion of the concave-to convex curvature engages the convex curvature of the driver flange in a rest position. The downward movement of the mandibular piece moves the convex portion of the posterior side of the protrusive flange along the convex curvature of the driver flange moves the user's mandible forward. The mandibular piece has a first buccal saliva drain in a right buccal surface and a second buccal saliva drain in a left buccal surface, which each are formed of an elongate arcuate ridge extending from proximate an incisor region to a posterior terminus surface. The mandibular piece can also include a first lingual saliva drain in a right lingual surface and a second lingual saliva drain in a left lingual surface, which each have an elongate arcuate ridge extending from proximate the incisor region to the posterior terminus surface. Each elongate arcuate ridge is sloped caudally away from the tooth covering.

In another aspect, the maxillary piece has a first cranial saliva drain and a second cranial saliva drain, that each have an elongate trough extending from proximate the incisor region to the posterior terminus surface thereof. The maxillary piece comprises a front saliva flow channel extending between left and right incisor regions. The maxillary piece comprises an undulated sloping saliva drain channels on each of the lingual surfaces proximate the respective incisor region to the respective posterior terminus surface. The undulations are angled to direct saliva posteriorly to the soft palate.

In another aspect, the maxillary piece comprises a flow tube at the incisor region having flow therethrough in an anterior to posterior direction and vice versa. The flow tube houses a sensor in electrical communication with a microprocessor housed in the maxillary piece. The flow tube houses a speech module configured to adjust the volume and amplitude of speech.

BRIEF DESCRIPTION OF THE DRAWINGS

Many aspects of the disclosure can be better understood with reference to the following drawings. The components in the drawings are not necessarily to scale, emphasis instead being placed upon clearly illustrating the principles of the present system.

FIG. 30 is a chart of plateau height and combined cranial-caudal repositioning and anterior-posterior repositioned effect.

FIG. 31 is a chart of theoretical post treatment airway dimension and oxygenation in severe and moderate OSA when using an AVMLRD disclosed herein.

FIG. 32 is a chart of actual post-treatment data using an AVMLR as compared to a BiPAP machine for a selected user.

FIG. 57 is a Table version of Algorithm I from an Excel worksheet showing the equations in the cells.

FIG. 58 is Algorithm I filled in with one example of data inputs and the corresponding calculated outputs.

FIG. 59 is a Table version of Algorithm II from an Excel worksheet showing the equations in the cells and then filled in with one example of data inputs and the corresponding calculated outputs.

FIG. 60 is Algorithm I and Algorithm II filled in with data inputs from Working Example 2 and the corresponding calculated outputs.

FIG. 61 is Algorithm II filled in with a change in the target heart rate because the individual in Working Example two gained weight, thereby changing many of the calculated outputs.

DETAILED DESCRIPTION

Figure 1:
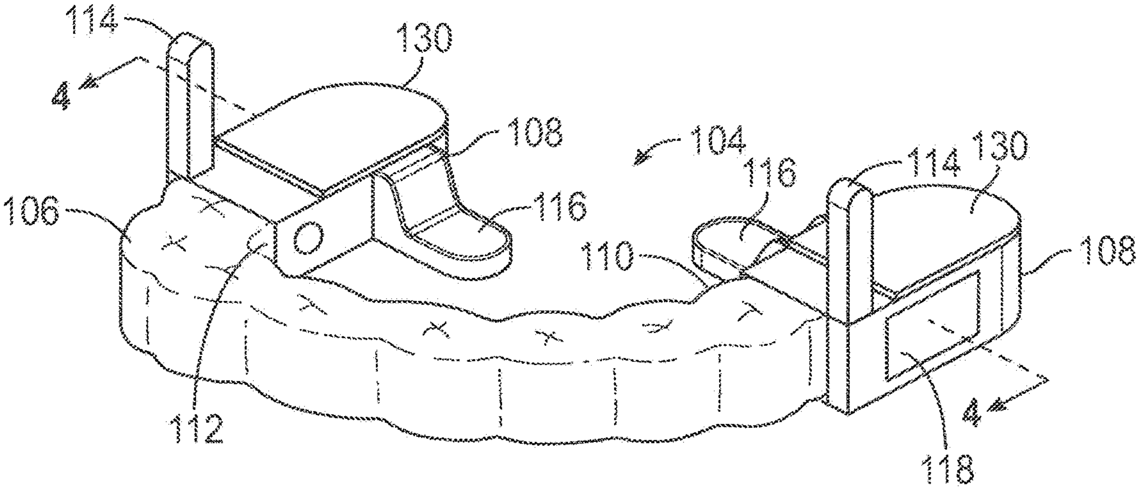
FIG. 1 is a left-side view of a first embodiment of a mandibular lingual repositioning device.

The following detailed description will illustrate the general principles of the invention, examples of which are additionally illustrated in the accompanying drawings. In the drawings, like reference numbers indicate identical or functionally similar elements.

Figure 2:
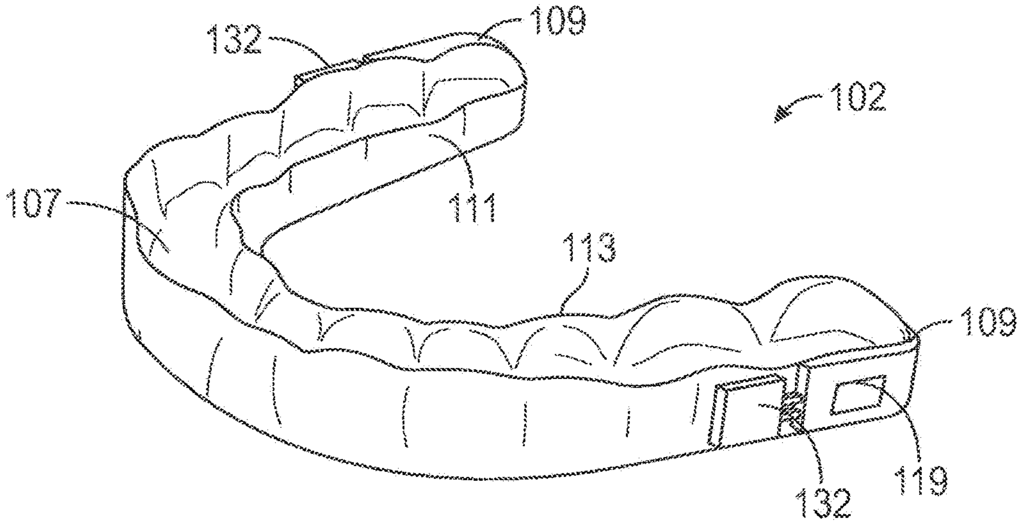
FIG. 2 is a side, perspective view of the mandibular piece of the mandibular lingual repositioning device of FIG. 1.
Figure 3:
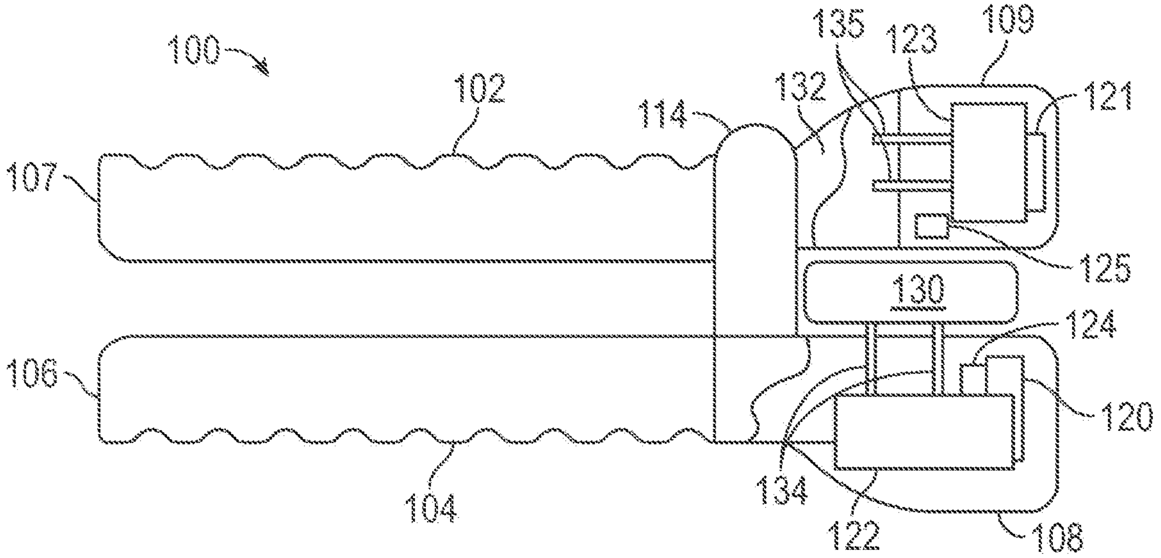
FIG. 3 is a side, perspective view of the maxillary piece as it articulates and fits with the mandibular lingual repositioning device of FIG. 1.

Referring now to FIGS. 1 to 4, a mandibular lingual repositioning device (MLRD) that is dynamic in its movement of the jaw(s) and tongue is represented collectively in FIG. 3 by reference number 100. The MLRD 100 has a maxillary piece 102 seated on a mandibular piece 104 for operative communication of drivers built therein.

Figure 4:
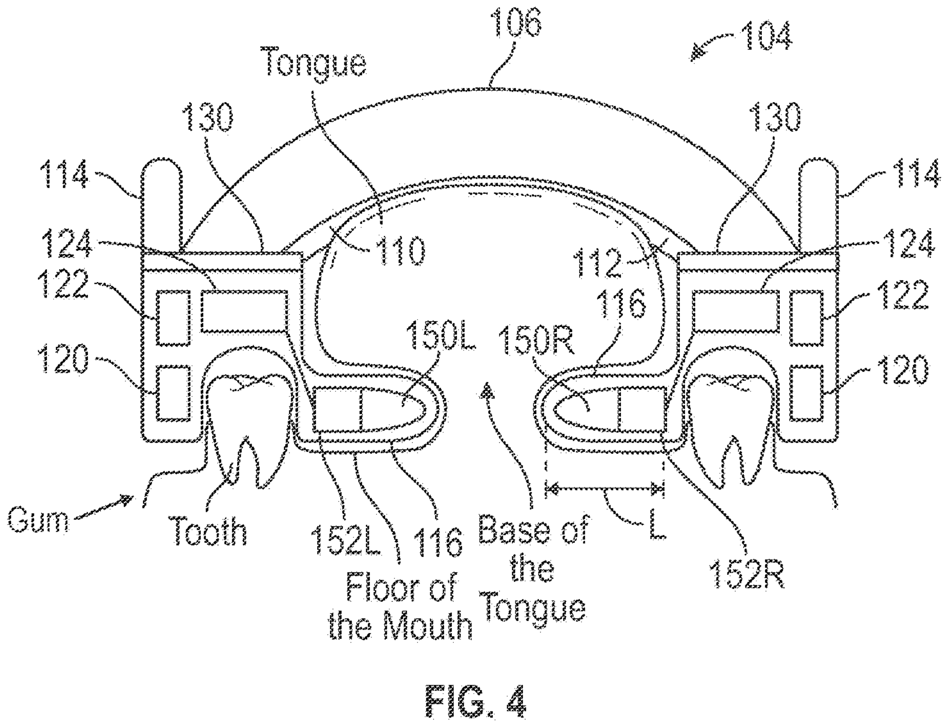
FIG. 4 is a cross-sectional view of the mandibular lingual repositioning device along line 4-4 in FIG. 1.

Turning to FIGS. 1 and 4, the mandibular piece 104 is shown, which has a first teeth covering 106 and has a housing 108 proximate each of a left molar portion 110 and a right molar portion 112. A protrusive flange 114 extends cranially from each housing 108, and a stimulator 116 extends from each housing 108 toward the tongue at a position to lie under the tongue in contact with lingual muscles, in particular the Genioglossus (GG), the Geniohyoid (GH), sub-mentalis (SM), and Glossopharyngeal (GP) muscles. The stimulator protrusion 116 of each housing 108 should be fitted to the user/custom made for the user to ensure proper contact with the lingual muscles. Each stimulator portion 116 while appearing somewhat boxy-looking in the drawings, is more preferably molded of moldable material suitable for use in a human oral cavity and has smooth transitions to its shape and is shaped to match the shape of the user's mouth, especially to sit under the tongue in contact with the base of the tongue and the floor of the mouth as shown in FIG. 4. The stimulator may extend into a flexible soft, continuous stretch of material that extends from the lingual caudal edge of the mandibular piece wrapping around to the left and right molar region and gently lays on the floor of the mouth and around the base of the tongue in close contact with the genioglossus and geniohyoid muscles that originates at the caudal sub-mental surface of the mandible. Electrical stimulation of the entire floor of the oral cavity through the stimulator will create contraction of these muscles thus facilitating the entire bulk of the posterior aspect of the tongue to be pulled anteriorly, the floor of the mouth pulled cranially, the hyoid bone pulled anteriorly and lifted cranially while pulling the lateral walls of the SMCA laterally. This movement widens the antero-posterior and lateral diameters of SMCA while shortening the entire length of the airway tube in the vertical dimension.

The moldable material may be any of those commercially available or hereinafter developed for use in a human oral cavity. The moldable material can be shaped and sized to fit the entire tongue like a glove or sock. It may also retain the tongue in its awake position thereby preventing it from falling back passively into the airway while asleep whilst still allowing voluntary movements of the tongue such as involved in speech and swallowing. The moldable material could also extend from the molar left side all the way to the front and then to the right side, thus fitting like a horse-shoe around the base of the tongue so as to evenly electrify all components of the muscles it comes in contact with when an electrical stimulator is present.

Referring now to the transverse cross-section of FIG. 4, each housing 108 encloses, in a fluid-tight manner, a power source 120 electrically connected to a motor 122, to a circuit board 124, and to the stimulator 116. A first driver 130 is operatively connected to each motor 122 for cranial to caudal adjustments of the device 100. The first driver 130 is linearly translatable by linkages 134 operatively connected to the motor 122 within its housing 108 as shown in FIG. 3. The linkages 134 will be fluid-proof, heat-resistant and acid-resistant and thus able to withstand the conditions found within the oral cavity of a user.

With reference to FIGS. 2 and 3, the maxillary piece 102 is shown, which has a second teeth covering 107 and has a housing 109 proximate each of a left molar portion 111 and a right molar portion 113. Referring to the partial cross-sectional view of FIG. 3, each housing 109 encloses a power source 121 electrically connected to a motor 123 and to a circuit board 125. A second driver 132 is operatively connected to each motor 123 for anterior to posterior adjustments of the device 100. The second driver 132 is linearly translatable by linkages 135 operatively connected to the motor 123 within its housing 109.

In all embodiments, the housings 108 and 109 may be fixedly attached to the respective teeth covering, integral therewith, or removable attachable thereto. When removable attachable, the housings 108, 109 may be slid over a molar portion of the teeth covering, have a snap fit thereto, an interference fit thereto, may be a two-piece compartment that snaps together over a predetermined location of the teeth covering, may be three-dimensionally printed to cover or fit over a portion of the teeth covering. In all embodiments, while the teeth coverings 106, 107 are shown as full coverings for all teeth in the mandible and all teeth in the maxilla, the teeth coverings are not limited thereto. Instead, each teeth covering may be a partial cover for one or more teeth, as such, the mandibular piece 104 may be a two-part configuration having a left and a right portion each with a housing 108 and the maxillary piece 102 may be a two-part configuration having a left and a right portion each with a housing 109.

In all embodiments herein, each housing 108, 109 is described herein as positioned proximate a molar portion of a teeth covering, but is not limited to any particular size, i.e., the number of teeth to which it is associated. Each housing may be associated with one tooth region, a two-tooth region, a three-tooth region, or whatever number of teeth is needed to accommodate the size and position of the housing and its stimulator protrusion.

Figure 6:
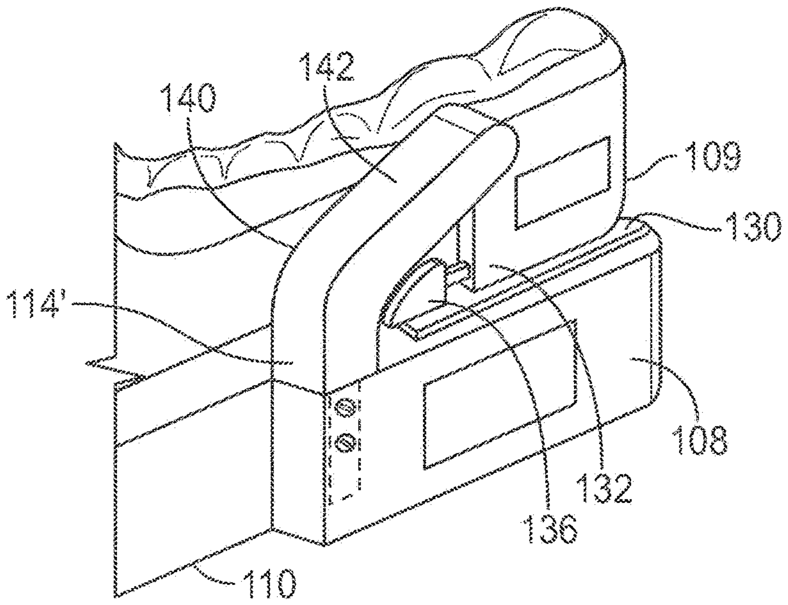
FIG. 6 is an enlarged view of the left movement mechanism of the mandibular lingual repositioning device of FIG. 1.
Figure 7:
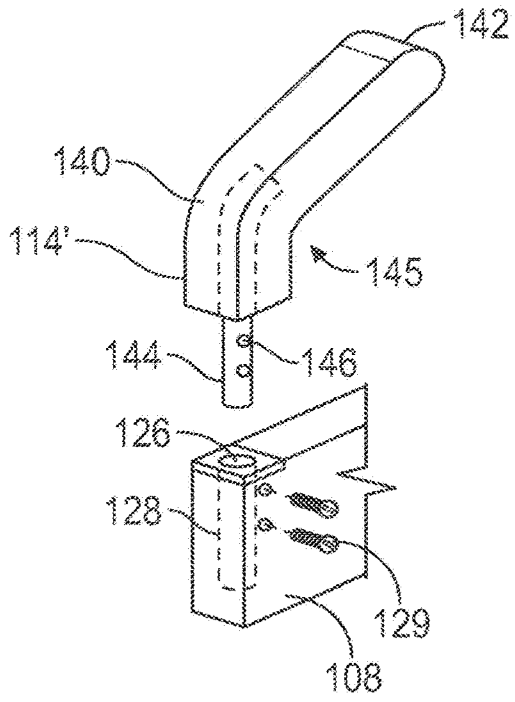
FIG. 7 is an enlarged view of an alternate embodiment of the left movement mechanism of the mandibular lingual repositioning device.

Referring to FIGS. 1, 3, and 4, the protrusive flange 114 of the mandibular piece 104 is an elongate flange that is releasably, removably attached to or may be integral with the housing 108. A releasably, removably attachable protrusive flange 114 is shown in FIGS. 6 and 7 to accommodate an interchangeability of protrusive flanges 114 of different shapes and sizes to provide the best fit for the user's mouth. In the embodiment of FIG. 1, the protrusive flanges 114 are generally an elongate linear flange protruding cranially from each of the housing 108. The protrusive flange 114 may be a housing containing within an antenna, a receiver-transmitter for two-way communication, an infrared homing or signaling device, a unique signature emitting device, an encoder or a multi-polarity magnetic clasp that facilitates coordinated movements with the second driver 132 with which the protrusive flange 114 articulates.

Turning now to FIGS. 6 and 7, the protrusive flange 114' is releasably attachable to the housing 108 of the mandibular piece 104. The protrusive flange terminates with a post 144 opposite a free end 142 thereof. The post 142 includes a releasably attachable feature 146, such as a snap fit feature, a friction fit feature, or threaded holes as shown in FIG. 7. The housing 108 defines a receptacle 126 shaped to receive the post 144. The receptacle 126 will have a releasably attachable mating feature 128 that mates with the releasably attachable feature 146 of the post 144. In FIG. 7, the releasably attachable mating feature 128 is a set of threaded holes and screws 129.

Figure 8:
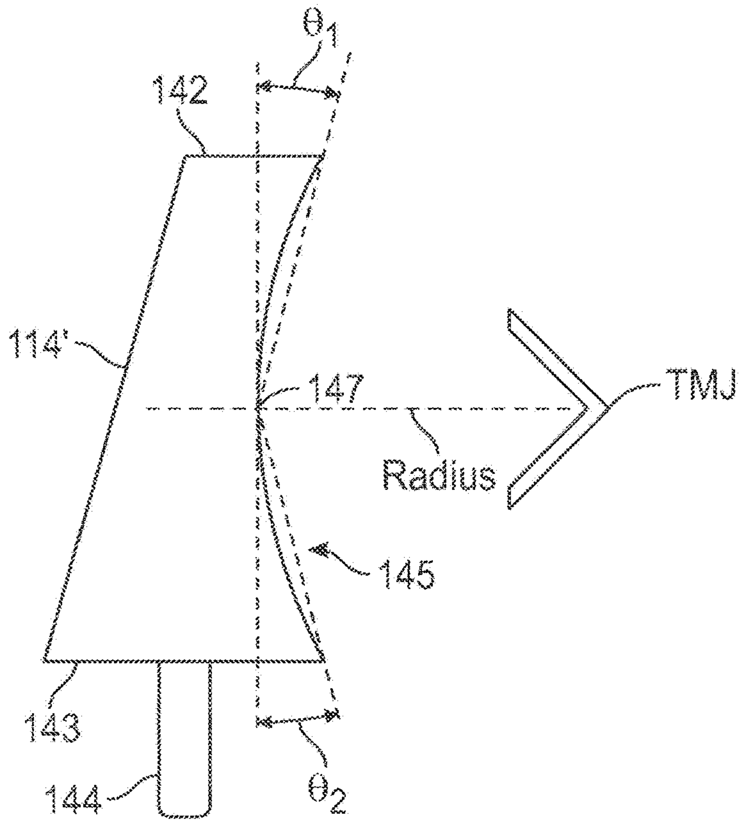
FIG. 8 is an enlarged side view of an embodiment of a protrusive flange.

As shown in FIGS. 6 and 7, the protrusive flange 114' can have a bend 140 on the anterior side of the flange, but this is not required. The new feature in this embodiment is that the posterior side 145 of the protrusive flange 114' is arcuately shaped as best shown in FIG. 8 as a concave surface, which mates with a driver 132 having a convex surface shaped to match the concavity of the posterior side 145. The protrusive flange 114 or 114' and its post 144 may lean posteriorly at any angle that may suit the need of a particular user. The midpoint 147, relative to being the middle or halfway point between the free end 142 and the opposing end 143, of the arcuately shaped posterior side 145 defines an arc of a circle having its center at the temporo-mandibular joint (TMJ) in this illustration and the free end 142 has a width that is smaller than a width of the opposing end 143 of the flange. The arc of the circle is one that defines $\theta_1$ as being any angle with the range of 12 degrees to 15 degrees in increments of whole degrees, half degree, or 0.2 degree increments. The angle of the arc $\theta_1$ defines the amount of protrusion of the mandible with each degree of mouth opening. The larger this angle θ1, the greater the protrusion with mouth opening. The larger the angle of mouth opening, the larger the protrusion of the mandible. Furthermore, a strong correlation between mandible movement and Apnea/Hypopnea events has been shown in the literature. Increased respiratory effort (due to OSA) is associated with increased mandibular movements and mouth opening. Data shows 98% (n=33) of open mouthing and large mandibular movement of 99.6% (n=33) were observed in OSA patients (children) who were confirmed to have OSA by polysomnography. "Mandibular movements were predominantly a change in position during increased upper airway resistance during the respiratory cycle as exhibited by mandibular lowering and jaw opening". Mandibular Movements Identify Respiratory Effort in Pediatric Obstructive Sleep Apnea (aasm.org). "The mandible is the anchor for upper airway muscles that dilate and elongate the pharynx and its position determines mouth opening. In OSA, the mandible lowers to a greater degree than in normal sleep due to activation of the upper airway muscles allowing traction on hyoid bone and mouth opening to facilitate mouth breathing".

The arcuate surface is customizable to provide a curvature that provides the best forward movement of the mandible for the user in relation to the individual user's mouth shape and size. Depending upon the shape and size of the user's mouth and jaws, the radius defining the point of the arc may be offset by moving this point up or down relative to the midpoint 147, which may change the widths of the free end 142 and the opposing end 143.

The advantage to the arcuately shaped side 145 of the protrusive flange 114' is that it will help protrude the mandible forward as the Temporo-Mandibular joint (TMJ) relaxes and the mouth falls open during sleep, wake or any other transitional state of the human mind (such as various Parasomnia create) thus allowing gradual smooth arcuate incremental forward mandibular movement to occur as concave surface 145 of protrusive flange 114' smoothly glides against convex surface 136 of driver 132'. The maximum protrusive distance (MPD) for anterior movement of the mandible is in a range of 0 mm to 15 mm, more typically 6 mm to 10 mm. Typically, the first 13 degrees of rotation of the mandible about the TMJ during natural, un-aided spontaneous mouth opening does not move the mandible anteriorly, i.e., this rotation does not change or open the airway. Drivers 130, 132 will actively coordinate simultaneous desired amount of vertical and protrusive movements of the mandible (controlled by controller) during this first 13 degrees of mouth opening while the arcuate opposing gliding movements of concave surface 145 of protrusive flange 114' smoothly against convex surface 136 of driver 132' surfaces will passively create mild forward movement of the mandible and tongue away from the airway, thus increasing the size of the airway. Driver 132 will ensure constant contact between surfaces 145 and 136 while driver 130 will adjust height of oral cavity through its own cranial movements that translate caudal mandibular advancement, facilitating mouth opening and thus increase oral cavity volume in order to create room for the advancing tongue while simultaneously stiffening the soft palate and Uvula (through the muscles palatoglossus, palatopharyngeus and tensor palatini). This entire process will work in synergy (keeping the person's sleep undisturbed) to increase cross-sectional area of upper airway and increase the cubic volume of the oral cavity which in turn allows 150L/R (through the controller) in 116 to appropriately incrementally protrude the base of tongue forward into the increased oral cavity volume utilizing electric stimulation of the tongue nerves and muscles (details described elsewhere in this document), further increasing the cross-sectional area of the upper airway (the tongue forms the anterior wall of the upper airway).

In the natural state, the mandible must rotate beyond this initial 13 degrees, typically through another 7 to 13 degrees to have an effect on the airway size. This natural movement comes at the price of reducing the antero-posterior (AP) diameter of the airway, thus constricting the airway. In an example, where the arcuately shaped side 145 is based on a 15 degrees jaw rotation (end to end) curvature, i.e., $q_1$ and $q_2$ are 15 degrees each or they may be any combination of two different angles that add up to 30 degrees. The approximate midpoint 147 of the arc 145 is the point at which transition between angle of $q_2$ and $q_1$ occurs and is approximately the point at which the mandible (mouth) is expected to have opened or rotated to the first 13 degrees (12 to 15 degree range). Total theta at the point of transition 147=180−($q_1$+$q_2$). Surface 136 of driver 132 should align with the lower part of surface 145 closer to 143 when the mouth is completely closed (Centric Occlusion CO with a Centric Relation CR between mandibular and maxillary incisor teeth). Angle of $q_2$ can be different from angle of $q_1$, i.e. the arc may or may not be one fixed radius from TMJ. Each of the $q_1$ and $q_2$ should remain between the ranges of 12-15 degrees each although both $q_1$ or $q_2$ or both could be zero degrees each (0-15 degrees each). These angles could exceed 15 degrees each based on individual needs of the user/patient. Total of ($q_1$+$q_2$) will ordinarily be between 24-30 degrees but could be 0-30 degrees or greater. Theta at point of transition 147 is (180−($q_1$+$q_2$))=150 to 180 degrees unless angles of $q_1$ and or $q_2$ exceeded 15 degrees. A q of 0 degrees will essentially create a straight vertical posterior surface 145 and would require a similar angle for surface 136. An angle of 180 would produce incremental forward protrusive movement of the mandible throughout the entire range of mandibular rotation (CR/CO to MMO) during mouth opening. The congruent relationship of surfaces 145 and 136 may create a posterior lean in the vertical axes of both surfaces such that their superior (cranial) edges may be posterior in relationship to their inferior (caudal) edges, thereby facilitating an anterior mandibular advancement as surface 145 slides down surface 136 with mouth opening (caudal mandibular advancement).

$q_2$ is primarily useful to control neutral mandibular protrusion during the initial 13 degrees of mandibular rotation (although protrusive flange can protrude the mandible when using MRD with motorized protrusive flange option) but can be adjusted to produce protrusive movement (the more $q_2$ is, the less the radius of mandibular incisor to TMJ, the less protrusion of the mandible during early rotation or mouth opening and the less $q_2$ is the more protrusion with each degree of mandibular rotation). On the other hand, $q_1$ is used to create the majority of the forward mandibular protrusion during the remainder of the mandibular rotation or mouth opening all the way to MMO (Maximum mouth opening). Resistance to mouth opening will also occur during this part of mandibular rotation due to the resistance from stretching the muscles of the TMJ as the mandible incrementally protrudes with every additional degree of mandibular rotation. Increasing $q_1$ will cause even more protrusion of mandible and thus also cause incremental resistance to mouth opening created by forward jaw movement. Essentially, if the desired outcome is to keep the mouth closed or barely open (CR/CO position), one could use only $q_1$ and remove $q_2$ altogether. This would require an arcuate or non-arcuate straight posterior surface 145 with $q_1$ of 0-15 degrees from the vertical axis starting at base 143 all the way up to 142 as shown in FIG. 6 and FIG. 7 with a corresponding surface 136 that is straight non-arcuate surface with a corresponding angle $90+q_1$ or a corresponding arcuate surface that leans back as shown in FIG. 6 or combination of arcuate and non-arcuate surfaces such as shown in FIG. 6. Under these circumstances, greater the $q_1$ greater the protrusion of the mandible with the least amount of mandibular rotation or mouth opening (mm of protrusion for each degree of mandibular rotation) and thus also ensure the highest resistance to mandibular rotation and mouth opening to match the needs of the user/patient. In an example, where the arcuately shaped side 145 is customized with $q_1$ and $q_2$ of 15 degrees each as well (total theta=180−30=150) for the sake of simplicity of driving home the point, a mandibular rotation or mouth opening of about 20 degrees will protrude the jaw anteriorly about 5 mm and a mandibular rotation of about 24 degrees will protrude the jaw anteriorly about 11 mm. Since the MPD (Maximum Protrusive Distance with range of 6-10 mm) typically has an absolute maximum of 10 mm, 11 mm is nearly impossible for most people and thus the mechanics of the device create the environment where the mouth will not open to MMO (Maximum mouth opening) of 24 degrees. However, as in some individuals, maximum advancement may be up to 15 mm, in those individuals the device would allow the freedom of further advancement.

The releasably attachable features of the flange 114' accommodates the interchangeability of protrusive flanges 114 of different shapes and sizes to provide the best fit for the user's mouth.

Turning now to FIGS. 18-21, some people in need of Continuous Open Airway Technology (COAT) may suffer from dysfunction or abnormalities of the temporo-mandibular joint (TMJ). These individuals may not have evidence of TMJ disease but may have mild restriction of the range of movement of the TMJ and mandibular advancement. As such, milder advancements of the mandible are needed for these individuals when using a mandibular repositioning device (MRD), such as the MRD 800 of FIG. 18. The MRD 800 has Dynamic Continuous Open Airway Technology (DCOAT) because the mandible will follow $Arc_2$ of FIG. 20 in which as the mandible drops to open the mouth, the mandible will move forward in small increments because of the shape of the protrusive flange 814 and the driver flange 832, thereby opening the airway. $Arc_2$ demonstrates that when the mandible opens in 5 degree increments relative to the TMJ, the forward point of the mandible changes as shown in Table 1 below.

TABLE 1

$Arc_2$ Degrees of Travel corelated to Mandible position

| Degrees of Mouth Opening | Distance from the TMJ (centimeters) |
|---|---|
| 0 | 7 7/8 |
| 5 | 8 1/8 |
| 10 | 8 3/8 |
| 15 | 8 7/16 |
| 20 | 8 9/16 |
| 25 | 8 3/4 |

In comparison, $Arc_1$ demonstrates the movement of commercially available COAT MRDs, which allow the mandible to open caudally, but allow the mandible to fall backward toward the throat; thus, obstructing the airway or adding to the obstruction.

Figure 18:
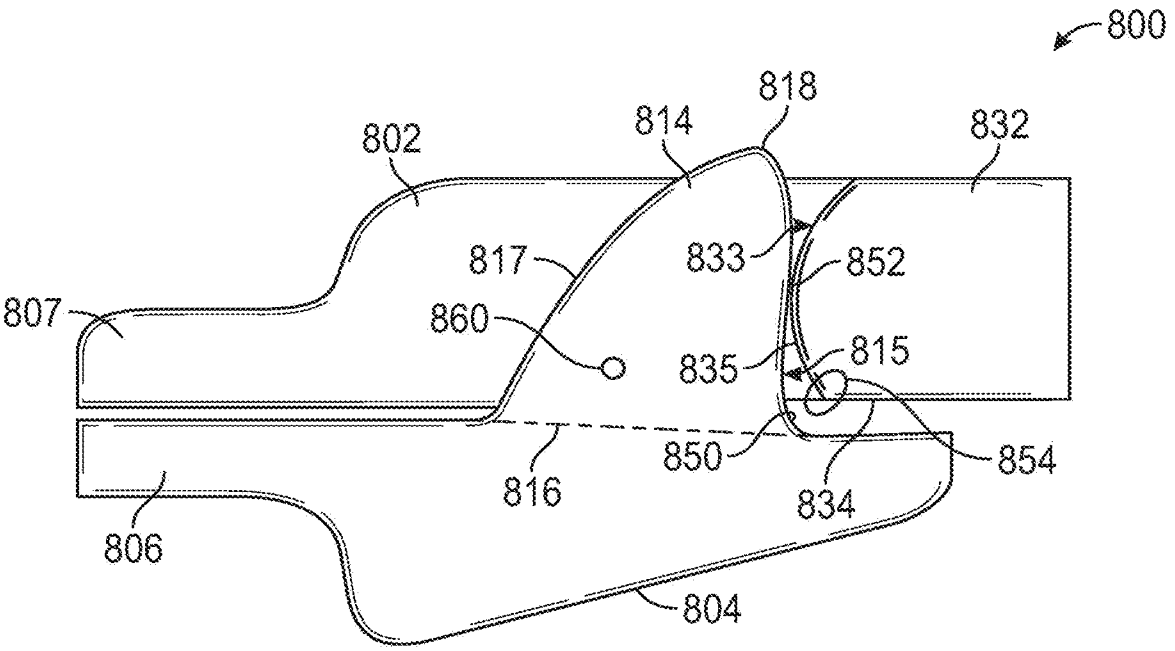
FIG. 18 is a side view of an embodiment of a mandibular repositioning device that provides Dynamic Continuous Open Airway Technology (DCOAT) to the user.
Figure 19:
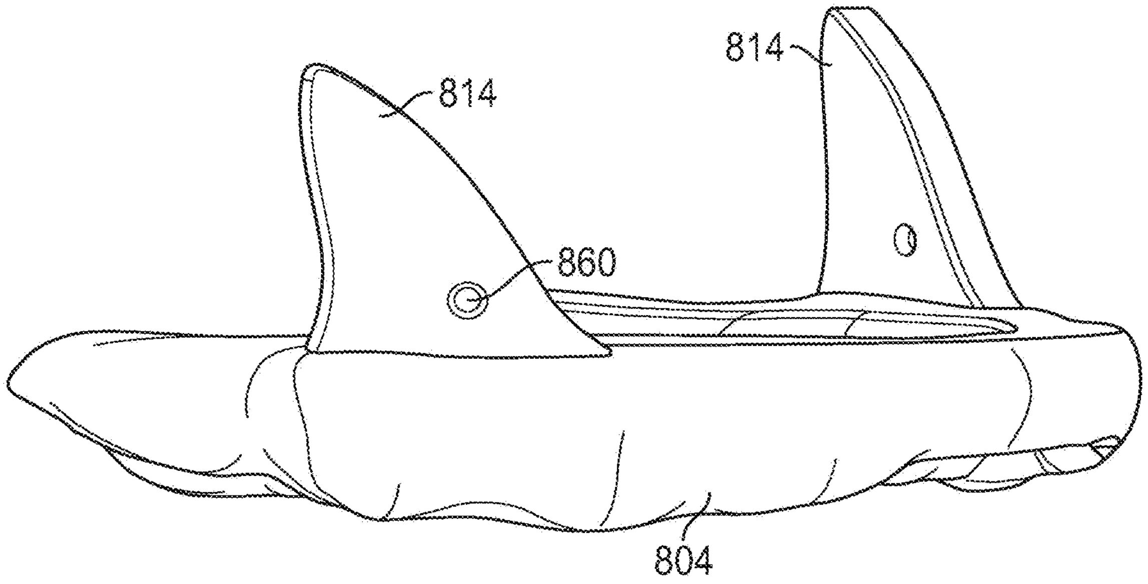
FIG. 19 is a side perspective view of the mandibular piece of the mandibular repositioning device of FIG. 18.
Figure 20:
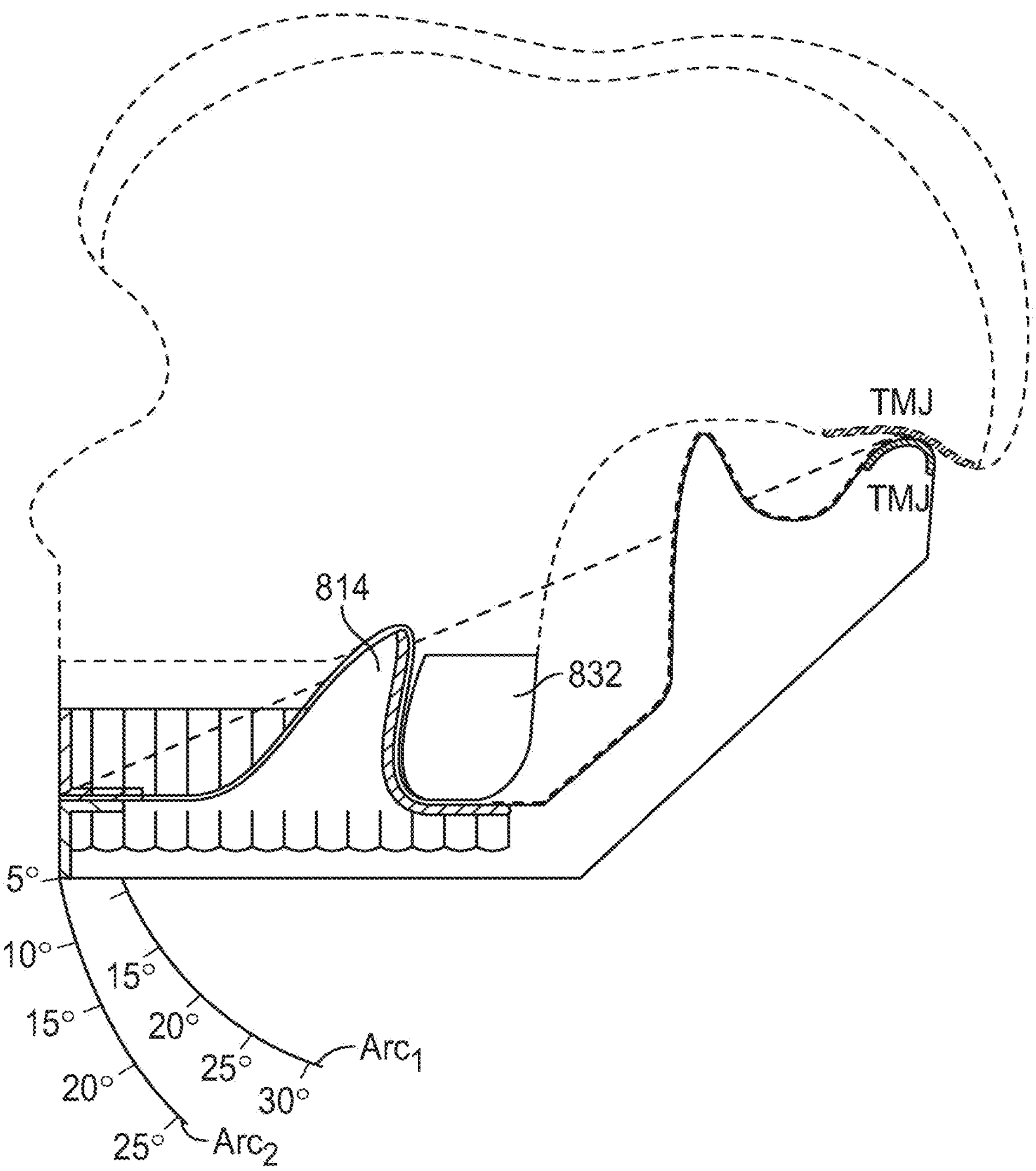
FIG. 20 is a model comparing the movement of the mandible of a user having the mandibular repositioning device of FIG. 18 against a commercially available mandibular repositioning device.
Figure 24:
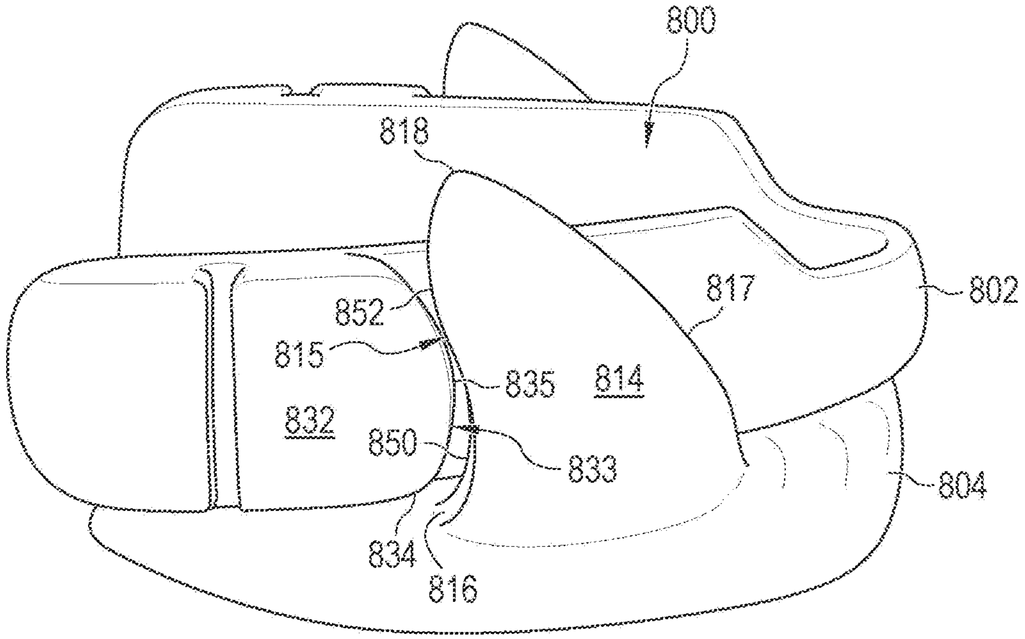
FIG. 24 is a photograph of a selected patient's mandibular repositioning device having the protrusive flange with the convex to concave curvature described herein against the convex curvature of the driver flange.

Turning now to FIGS. 18, 19 and 24, the various MRDs 800 have a concave-to-convex curvature moving from the base 816 to the most cranial point 818 of the posterior side 815 (or trailing edge) of the protrusive flange 814 of the mandibular piece 804 and a convex curvature 835 of the anterior side 833 (leading edge) of the driver flange 832. While FIG. 18 only shows the left side of the MRD 800, it is understood that the right side can be the same, and FIG. 19 shows a left side and has a mirror image for the right side. It is also understood that each side (left and right) of the mandibular piece and or the maxillary piece may, in fact, be just partial (2-5 teeth) coverings that may end with the anterior or leading edges 817 and 833 of the mandibular and maxillary pieces respectively or may extend further anteriorly to cover more teeth. The number of teeth covered may be different for the right and left side of each of these pieces as well. Thus, there may be up to 4 individual pieces, Two (mandibular and maxillary) for the right and two for the left. This will provide therapeutics for individuals who have a mouth that is too small (micrognathia) to fit an entire bulky device. For most user's the left side and the right side will be mirror images, but if the user has a difference in jaw and/or facial structure making one side different from the other, the device can be custom shaped to accommodate the differences. The protrusive flange 814 extends cranially from the mandibular piece 804 which has a teeth covering 806 for the lower teeth. The driver flange 832 protrudes laterally outward from the side of the maxillary piece 802 a distance sufficient to engage the posterior side 815 of the protrusive flange 814 with the anterior side 833 thereof. The driver flange 832 has a base 834 positioned on the maxillary piece 802, i.e., the base of the driver flange does not extend caudally in an overlapping manner with the mandibular piece 804 in this embodiment. However, in another embodiment it may extend caudally as an extension of 835 in a way that it will be alongside (buccal side) of the mandibular piece 804, thus providing additional caudal anterior surface 833 for maintaining articulation with the posterior (trailing) surface 815 of the protrusive flange 814 during extremes of mouth opening such as yawning or otherwise. The maxillary piece 802 has a teeth covering 807 for the upper teeth. The protrusive flange 814 and the driver flange 832 are not shown in these embodiments to have the housings with the motor and mechanism for moving the flanges to provide the movements described herein for the other embodiment, but they are equally usable with such mechanisms and all the systems described herein.

The concave-to-convex curvature of the posterior side 815 of the protrusive flange 814 has a concave portion 850 most proximate the base of the protrusive flange. Cranially above the concave portion 850 is the convex section 852. The shape and positions of the concave and convex portions 850, 852 is described in more detail with reference to FIG. 21. The mathematical model in FIG. 21, was created using a scale of 1 cm=10 mm. Here, the dental horizontal axis ($A_H$) is represented by segment BC and runs horizontally between the mandibular teeth (crowns of the teeth) along the plane and the maxillary teeth (crowns) above the plane. Thus, the mandibular covering's part of the MRD lies below the horizontal axis while the maxillary covering's part lies above the horizontal axis. A vertical axis ($A_V$) is drawn perpendicular to the dental horizontal axis at a position passing between the protrusive flange 814 and the driver flange 832 in the at rest position shown in FIG. 21. The rest position is a position of the mandible at which there is no stress on the TMJ. This axis passes between the mating point $V_2$ of the protrusive flange 814 and the point $P_2$ of the driver flange 832. Point A represents the TMJ at rest and an axis parallel to the vertical axis ($A_V$) is drawn through point A, called the TMJ axis ($A_{TMJ}$). Point B is the point where the horizontal axis and the angle of the mandible intersect. The angle ABC created thus represents an angle adjacent to the angle of the ramus of the mandible. It is typically 40 degrees since the angle of the ramus of the mandible is 140 degrees on average. However, significant age, race and gender variations exist. We have assumed an angle of the ramus to be 100 degrees and the adjacent angle to be 80 degrees for sake of simplicity. The more obtuse the angle of the ramus, the more obtuse the tangent T and the greater the lean in the surface 835 of the protrusive flange 814 and surface 833 of the driver flange 832. Point C is the point where the TMJH vertical axis and the horizontal axis intersect. Point D is a mid-point of the length of the segment AC. Point E is a point along the TMJ axis that is at ⅔ of the height ($H_{DF}$) of the driver flange 832. Point F is the mirror of point D along the TMJ axis and Point G is the mirror of point A along the TMJ axis, i.e., a negative value equal to point D and Point A, respectively, below the horizontal dental axis. Point E 1 is the mirror of point E on a vertical axis parallel to the TMJ axis but positioned at the front of the incisors ($A_I$). Average dimensions were used in FIG. 21, and it is therefore understood that these dimensions may vary from individual to individual based on natural variations of body size, jaw size, head size and variations created by abnormalities of the human body as well.

Figure 21:
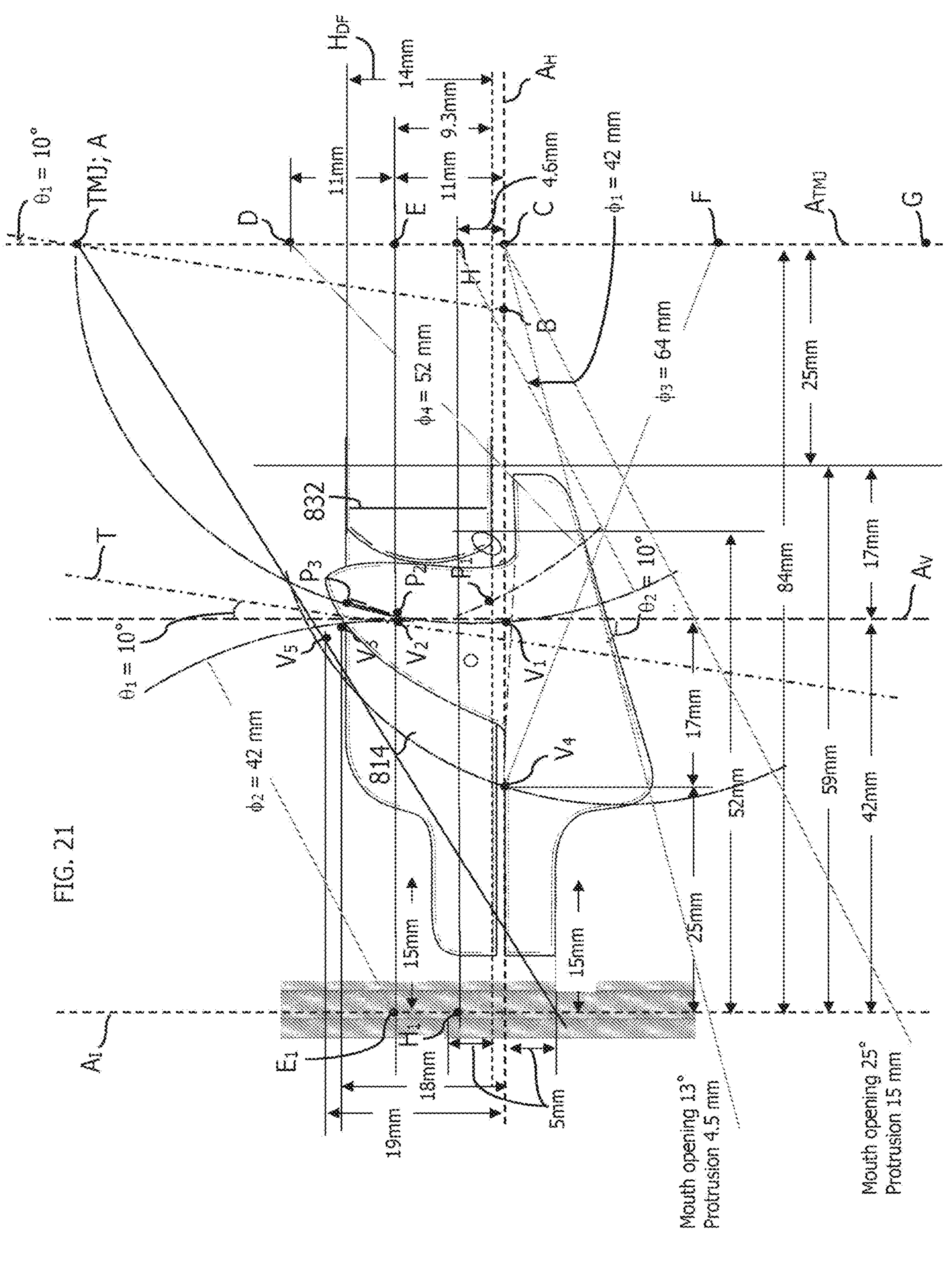
FIG. 21 is a mathematical model of how to position and determine the convex and concave curvatures of the protrusive flange and the driver flange of a mandibular reposition device.

The primary concept is to use a tangent (T) that is parallel to the lean of the Ramus of the mandible (represented by line segment AB) in relationship to the horizontal axis ($A_H$) that passes between the protrusive flange 814 and the driver flange 832 in the at rest position shown in FIG. 21. This creates an angle within the range of 10° to 50° with the vertical axis ($A_V$) on the maxillary side of the horizontal axis ($A_H$), which we call $q_1$. For the purpose of the following description and simplicity, 10° was selected for $q_1$ and $q_1=q_2$. However, $q_1$ can be any value within the 10° to 50° range. The tangent (T) defines the point $V_2$ of the protrusive flange 814 and the point $P_2$ of the driver flange 832 on the convex portions thereof, which are aligned in the at rest position. This is referred to as point $V_2P_2$ and is a point where three tangents meet to create the tangent (T). These are designed to meet at the same point although they do not always have to, especially, if a design for any individual requires a variance from this concept. Also, if the Ramus angle is different in each subject from what we have used for this discussion, T may change.

The five points labeled in FIG. 21 for the protrusive flange 814 are identified in this paragraph. Point $V_1$ is the lowest point on the trailing edge 815 of the protrusive flange 414 where it lands on the mandibular covering of the MRD. Point $V_2$ is where the tangent (T) coincides with point $P_2$. Point $V_3$ is the most cranial point of the trailing edge 815 of the protrusive flange 814. Point $V_4$ is the lowest point of the leading edge 817 of the protrusive flange 814. Point $V_5$ is the high point where $V_3$ reflects and meets the leading edge 817.

The three points labeled in FIG. 21 for the driver flange 832 are identified in this paragraph. Point $P_1$ is the lowest point of the leading edge 833 of the drive flange 832. $P_2$ is the point where tangent (T) coincides with point $V_2$. Point $P_3$ is the most cranial point of the leading edge 833.

At T=10°, the very front of the incisor part of the MRD to point C (the perpendicular dropped from A) appears to be 84 mm long. The midpoint of this segment is 42 mm (referred to herein as the midpoint length) from either end is at point $V_2$. This is an average distance and may vary on a case-by-case basis (as will all other measurements). About 4.6 mm above point C is a point that is one third of the height of segment AC measured from the horizontal dental plane, designated as point H. Using point H as a center point, a first arc $V_1$-$V_2P_2$ defining the curvature of the concave portion 850 of the trailing edge of protrusive flange 814 is drawn and a second arc $P_1$-$P_2$-$P_3$ (the entire leading edge of protrusive drive 832 is drawn using a radius 1 ($Ø_1$) of 42 mm (equal to the midpoint length). The 42 mm length for the radius could vary on a case-by-case basis.

The second arc $P_1$-$P_2$-$P_3$ defines almost the entire leading edge of the driver flange 832. The radius that will be used to draw the leading edge of the driver flange is about 0.2-0.5 mm shorter than the radius used to draw the trailing edge 815 of the protrusive flange 814 to allow a small play for the purpose of proper articulation. The leading edge 833 of the driver flange 832 has a back-cut portion 854 most proximate the point $P_1$. $P_1$ is described by a different radius, radius 4 (Ø4) of 52 mm on average. The center point used to draw the arc for the back-cut portion 854 is point D such that segment EC=ED=11 mm.

Point E is created by drawing a horizontal line from the point $V_2P_2$ such that the angle created by $V_2P_2$–C–$V_1$=10—thus allowing the point $V_2P_2$ to be the point where the tangent T=10° from the vertical axis. Now extending the horizontal line that passes through the points $V_2P_2$ and E further to the left allows creation of a point $E_1$, such that segment $V_2P_2$–$E_1$=42 mm=segment $V_2P_2$–E. Extending the line H similarly will allow the creation of $H_1$. With $E_1$ as center point using the same radius $Ø_2$=42 mm another arch is drawn that starts at $V_2P_2$ and extends upwards to $V_3$, thus completing the remainder of the trailing edge of the protrusive flange 814. $H_1$ may similarly be used and any point between $E_1$ and $H_1$ may also be used for the same purpose depending on the amount of convexity required at the top of the protrusive flange 814 to create best mandibular advancement for each individual person.

Figure 22:
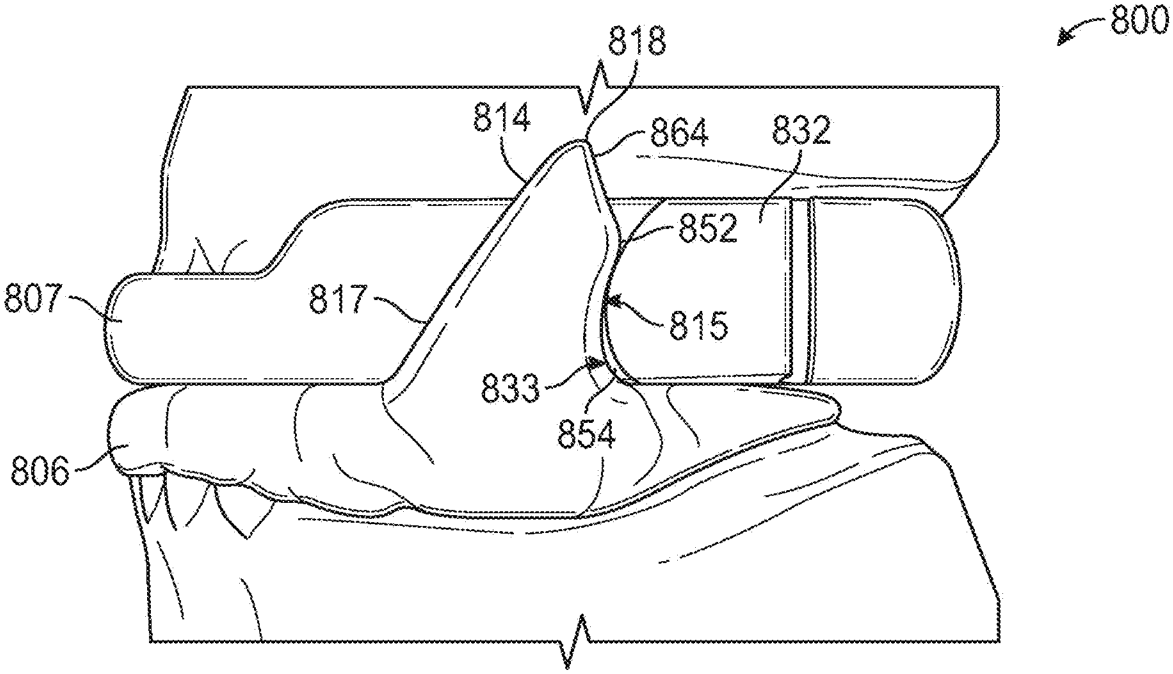
FIG. 22 is a side view of another embodiment of a mandibular repositioning device that provides Dynamic Continuous Open Airway Technology (DCOAT) to the user.
Figure 23:
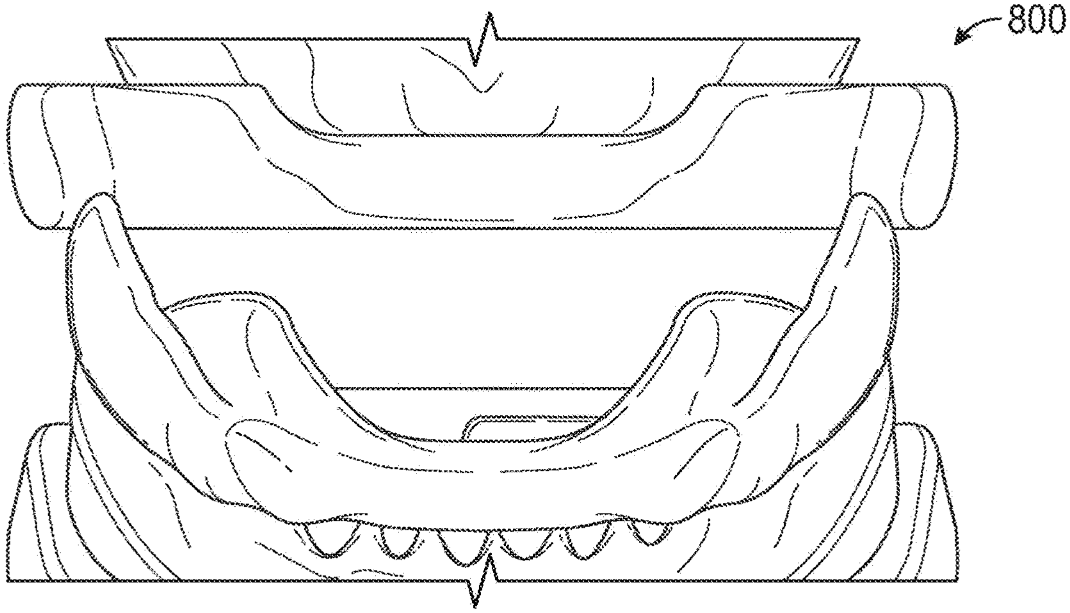
FIG. 23 is a front view of the device of FIG. 22 in a full-open mouth position.

To build the leading edge 817 of the protrusive flange 814, Point F was used as the center to draw arc $V_4$–$V_5$. This was then smoothed out at the top for a smooth transition to the trailing edge 815 and to avoid creating pointed edges. The convex curvature of the leading edge 817 is oriented with its curvature tilted toward the TMJ such that the most cranial point 818 (point $V_5$) is more proximate point $V_2$ than point $V_4$. However, turning now to FIGS. 22 and 23, an alternate embodiment 800' for the MRD is shown in which the leading edge 817 of the protrusive flange 814 can be more linear, yet still oriented tilted with the most cranial point 818 pointed toward the TMJ. Additionally, FIG. 22 has a back-cut portion 864 to the convex portion 852 most proximate the most cranial point 818, back-cut toward the most cranial point 818. FIG. 23 is a front view of the MRD 800' of FIG. 22 in a full-open mouth position with the back-cut portion 864 of the protrusive flange 814 seated against the back-cup portion 854 of the driver flange 832.

A user in need of an open airway, most often during sleep, but not limited thereto, inserts the maxillary and mandibular device of any of the embodiments disclosed herein into their mouth and goes about with their activity or goes to sleep. With respect to the shape of the flanges in FIGS. 18-29, when the user moves the mandible downward, such as normal relaxation during sleep, the protrusive flange 814 of the mandibular piece 804 moves along the convex curvature of the driver flange 832, which will move the mandible forward, see the increments of movement set forth in Table 1 above, and naturally opens the airway. Some users are capable of opening their mouths wider than others, and if, their mouth can open to a distance that is greater than the height of the protrusive flange 814 on the mandibular piece 804, there is a chance that the protrusive flange 814 could become disengaged from the driver flange 832 of the maxillary piece 802. To maintain contact between the mandibular piece 904 and maxillary piece 802 (prevent disengagement) during anterior-posterior repositioning and cranial-caudal repositioning, especially when both types of repositioning occur simultaneously, a plateau 870 of a preselected height (HP) has been added to the mandibular repositioning devices of FIGS. 25-29 between the base 816 of the protrusive flange 814 and the floor 872 of the tooth covering 806 of the mandibular piece. The preselected height (HP) of the plateau 870 prevents disconnect between each protrusive flange 814 and its respective driver flange 832 relative to a fully open mouth measurement between incisors of the user by having a height that compensates for the difference between the fully open mount measurement and the height of the protrusive flange ($H_{PF}$).

Figure 25:
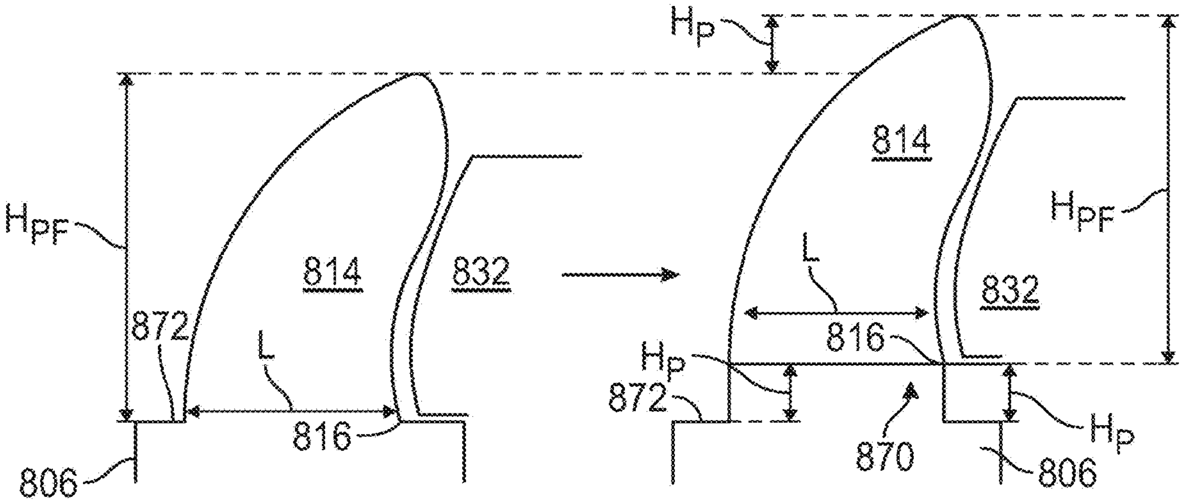
FIG. 25 is a comparison of a sketch representative of the mandibular repositioning device of FIG. 24 (left) to a sketch (right) thereof with a mandibular plateau added to the base of the protrusive flange.
Figure 26:
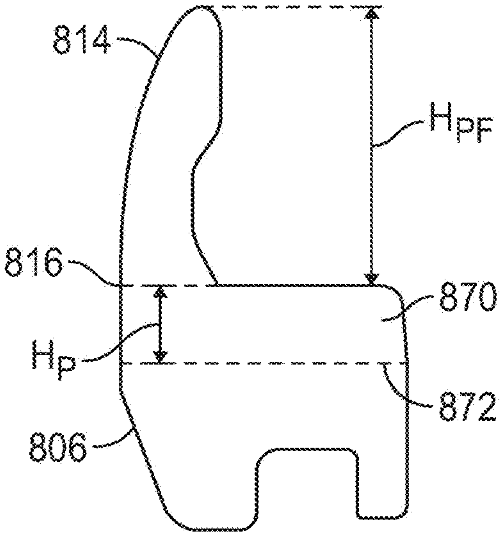
FIG. 26 is a rear view sketch of mandibular piece with the mandibular plateau of FIG. 25.

Referring to FIGS. 25-29, the preselected height (HP) for these examples was selected to be 1.06 mm because the user was capable of opening their mount 20.06 mm and the flange height ($H_{PF}$) was 19 mm. The flange height is typically less than 20 mm and is often in the range of 17 mm to 19 mm for the average adult. In another example, if a user has a fully open mouth measurement of 36 mm and the protrusive flange height is 19 mm, the preselected height for the plateau is 17 mm. As best seen in FIGS. 25 and 26, the plateau 870 extends across the full width of the tooth covering 806 and has a length (L) equivalent to the length of the base of the protrusive flange 814. Here, the plateau 870 has a uniform preselected height (HP) along the length (L) thereof.

Figure 27:
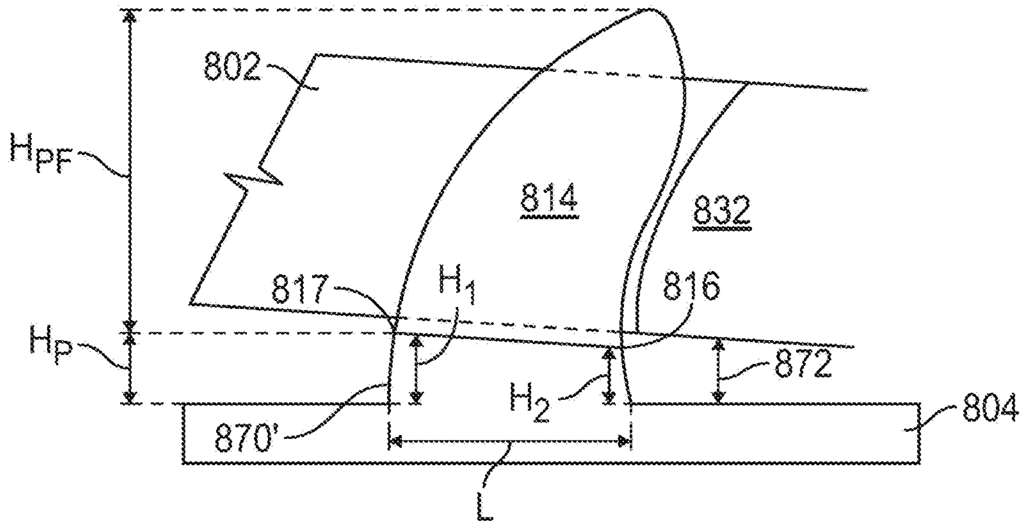
FIG. 27 is a side view of an alternate embodiment for a protrusive flange having a mandibular plateau that is wedge shaped.

Turning now to FIG. 27, the plateau 870' is wedge-shaped, thereby having a first height ($H_1$) at an anterior base 817 of the protrusive flange 814 that is greater than a second height ($H_2$) at the posterior base 816 of the protrusive flange. The plateau 870' causes the concave-convex curvature of the protrusive flange 814 to be inclined relative to the mandibular piece 804, thus the driver flange 832 is also inclined equivalently to the plateau 870' to maintain the engaged convex to convex mating curvature thereof. This creates a gap 872 between the driver flange 832 and the mandibular piece 804.

Figure 28:
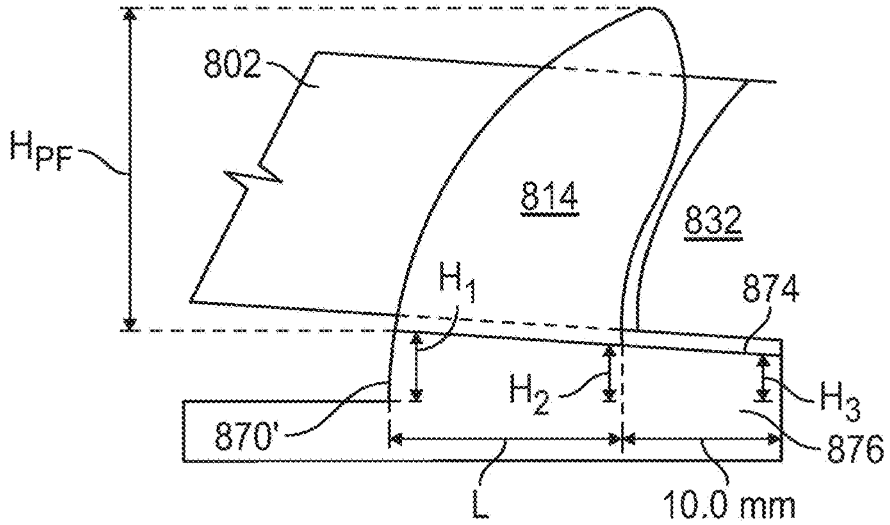
FIG. 28 is a side view of the embodiment of FIG. 27 with the mandibular plateau extended to the posterior surface to fill the gap shown in FIG. 27 created between mandibular piece and the maxillary piece.
Figure 29:
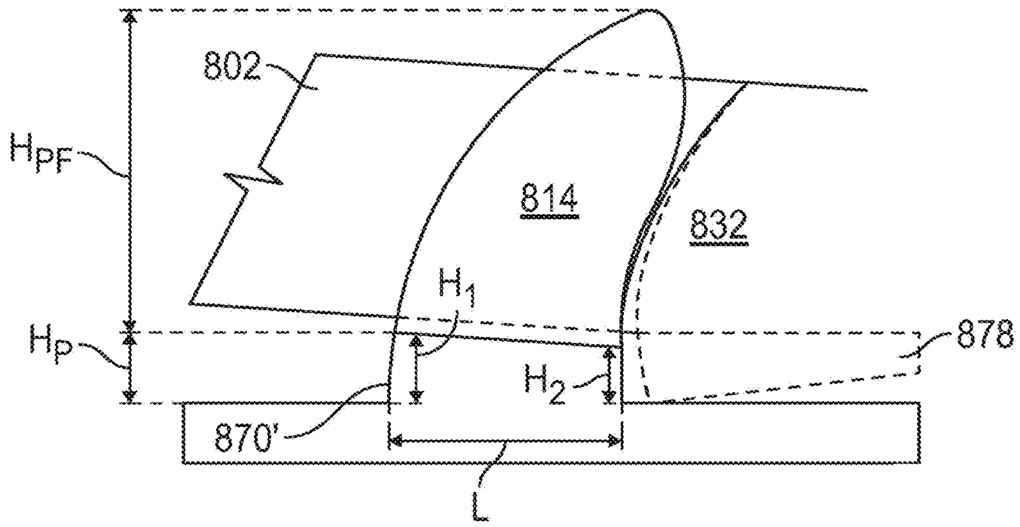
FIG. 29 is a side view of a maxillary piece having a driver flange that is extended caudally, represented by the dashed lines to fill the gap shown in 27 created between mandibular piece and the maxillary piece.

FIGS. 28 and 29 are examples of different embodiments for filling this gap with either an extension of the plateau 870' or of the driver flange 832, respectively. In FIG. 28, the plateau 870' has an extension 874 that extends posteriorly to a posterior terminus surface 876 of the tooth covering 806 of the mandibular piece 804. The extension 874 continues the wedge shape of the plateau 870' and terminates with a third height ($H_3$) that is less than the first height ($H_1$) and the second height ($H_2$). In FIG. 29, the plateau terminates posteriorly at the posterior base 816 of the protrusive flange 814 and the driver flange 832 has an extension 878 that extends caudally with its anterior side extending the convex curvature thereof past the posterior base 816 of the protrusive flange 814 into a gap 872 (FIG. 27). The driver flange 832 has a base that is seated on the mandibular piece 804 as a result of the presence of the extension 878. The extension 874 and 878 provide the benefit of added space for the housing in which the electrical components, motors, power sources, etc. that are described herein are enclosed. In another embodiment, extension 878 may extend caudally adjacent to the mandibular piece only thus allowing an extension for continued articulation between surfaces 833 and 815 with extremes of mouth opening.

Turning now to FIG. 30, the plateau provides significant benefits to the combined effect of the protrusive flange 814 and the driver flange 832 (anterior-posterior repositioning and cranial-caudal repositioning). For example, looking at columns 3 and 4 of FIG. 30, if a user actively opens their mouth 8.28 mm (5 degrees) in the absences of a plateau, the AVMLRD-aided anterior movement of the mandible is 6.25 mm for the average adult. With any of the mandibular repositioning devices of FIG. 25-29, which have a protrusive flange height of 19 mm and a plateau of 1.06 mm, and an anterior movement selected to be 5 mm at the rest position based on the curvature profiles of the protrusive flange and the driver flange, the same amount of anterior movement is achieved by opening the user's mouth just 1 degree. The anterior movement for the at rest position is typically set to be in the range of 1 mm to 6 mm (see the header of FIG. 30 at the far left). Without the plateau, the mandibular repositioning device has a limited range for the cranial-caudal repositioning as determined by the height of the protrusive flange, in other words, the addition of a plateau extends this range.

Still referring to FIG. 30, it has been determined that a combined effect within the 1 mm to 6 mm anterior movement at the rest position of: (i) Area 0: 2.25 mm to 7.4 mm is useful for treating primary snoring disorder and mild OSA; (ii) Area 1 and Area 2: 7.5 mm to 10.9 mm is useful to treat mild, moderate, and severe OSA with lowest saturation range of 81% to 90%; (ii) Area 3: 11 mm to 13.9 mm is useful to treat moderate and severe OSA with lowest saturation range of 79% to 81%; (iv) Area 4: 14 mm to 17.9 mm is useful to treat severe OSA with lowest saturation range of 76% to 79%; and (v) Area 5: 18 mm to 28 mm is useful to treat severe OSA with lowest saturation ranges below 76%. Further, the most useful is Area 1: a 5 mm to 6 mm anterior advancement in the rest position (central occlusion or centric relationship) with a 2 to 3 mm degree mouth opening by the user will treat mild to moderate OSA. Using the Area 1 configuration and the flange dimensions described for FIG. 25, the improvements expected for various parameters for a user were theoretically calculated and are listed in the table in FIG. 31.

Also, theoretical oxygen saturation improvements were calculated for the combined effect from 8.5 mm to 29 mm (from Area 1 to Area 5 of FIG. 30) and are presented in Table 2 below and further gains are expected with TAVMLR up to 32 mm or more.

TABLE 2

| TOTAL AVMLR (mm) | OXYGEN SAT. IMPROVEMENT (%) |
|---|---|
| 8.5 | 6.92 |
| 10 | 8.1 |
| 11 | 9.0 |
| 12 | 9.8 |
| 13 | 10.6 |
| 14 | 11.4 |
| 15 | 12.2 |
| 16 | 13.0 |
| 17 | 13.8 |
| 18 | 14.7 |
| 19 | 15.5 |
| 20 | 16.3 |
| 21 | 17.1 |
| 22 | 17.9 |
| 23 | 18.7 |
| 24 | 19.5 |
| 25 | 20.4 |
| 26 | 21.2 |
| 27 | 22.0 |
| 28 | 22.8 |
| 29 | 23.6 |

A sleep study of a user was conducted for a user having a mouth opening calculation: 23 mm mouth opening or 14 degrees opening with 0 mm Anterior Advancement, 23 mm Vertical Advancement, 17.5 Total AVMLR Advancement. A 17.5 total AVMLR combined effect is predicted to provide a 13.8% increase in oxygen saturation based on Table 2 above. The sleep study data is presented in FIG. 32. The AVMLR provided the user a 13.6% increase in oxygen saturation, which is in direct correlation to the theoretical improvement. Moreover, the data from the sleep study with the AVMLRD is shown in FIG. 32 in contrast to data pre-treatment and for treatment with a BiPAP machine. The user wearing the AVMLR experienced overall better sleep than using the BiPAP machine, in particular, improvement in every category of the sleep study, including a 50% decrease in respiratory disturbance and a 66.6% increase in REM sleep as compared to the BiPAP effects. The AVMLRD outperformed the BiPAP treatment with superior effect, including a greater than 10% increase in 5 out of seven categories and a greater than 20% increase in four of the seven categories.

In any and all of the embodiments disclosed herein, the protrusive flange 814 may be molded as an integral portion of the mandibular piece 804 but is preferably a removably attachable flange. When the flange is removable, it may include a hole or depression 860 as shown in FIG. 18 to receive a tool to activate a release of the fastener holding the removable attachable flange in place on the mandibular piece 804. Likewise, the drive flange 832 may be molded as an integral portion of the maxillary piece 802 or it may be removable attachable thereto. The fasteners for holding the flanges to their respective pieces 802, 804 can be any specifically described herein, and commercially available, or any hereinafter developed.

Figure 33:
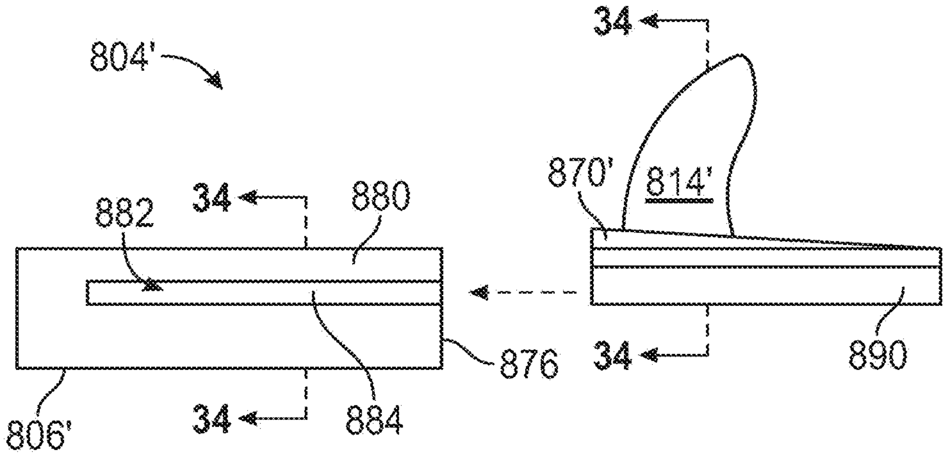
FIG. 33 is a side plan view of one embodiment of a mandibular piece with a removably replaceable protrusive flange in a pre-assembly position.
Figure 34:
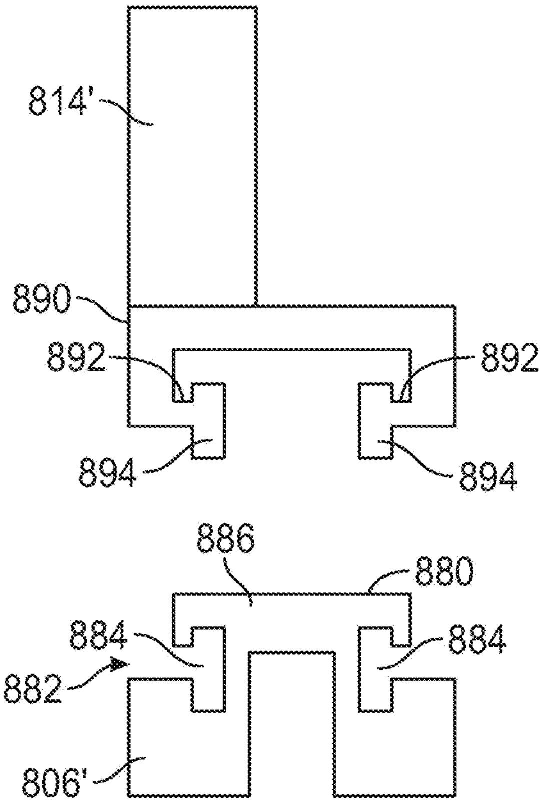
FIG. 34 is a rear view of the embodiment of FIG. 33 at the cross-section 34-34.

Turning now to FIGS. 33-34, the protrusive flange 814' can be removably replaceably attached to form the mandibular piece 804' by sliding into the tooth covering 806' from a posterior terminus surface 876 and engagingly saddles the dental crown 880 against cranial movement. The dental crown 880 defines a keyway 882 having opposed elongate grooves 884, one each open in the buccal and lingual directions, and defining a tongue 886 above the opposed elongate grooves 884. The protrusive flange 814' has a keyed slider 890 configured to slidingly mate to the keyway 882 of the dental crown 880. As such, the keyed slider 890 has an overall general U-shape with inwardly directed elongate, opposing arms 892 each terminating with elongate cranial to caudally oriented flanges 894.

Figure 35:
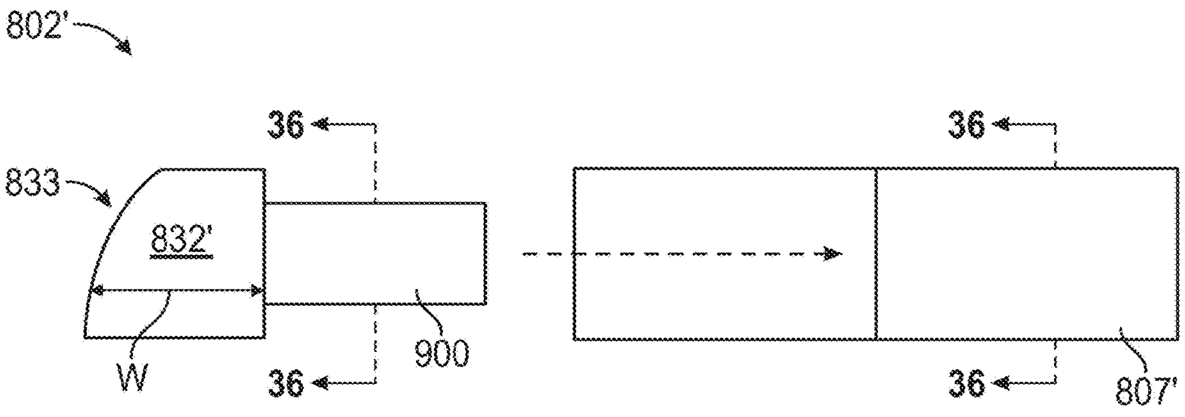
FIG. 35 is a side plan view of one embodiment of a maxillary piece with a removably replaceable driver flange in a pre-assembly position.
Figure 36:
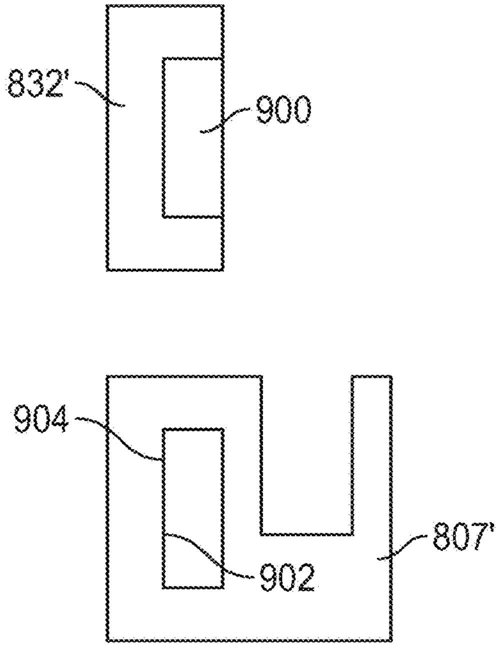
FIG. 36 is a rear view of the embodiment of FIG. 35 at the cross-section 36-36.

Turning now to FIGS. 35-36, each driver flange 832' is removably replaceably attached to the teeth covering 807' of the maxillary piece 802' by sliding a posteriorly extending post 900 into a slot 902 having an anterior opening 904. The maxillary piece 802' has a slot 902 buccally juxtaposed to a respective one of each of the left and right backmost teeth mold thereof. The orientation of the sliding attachment of each of the protrusive flange and the driver flange prevents the protrusive flange from sliding out of the mandibular pieces when the posterior side of the protrusive flange moves along the convex curvature of the driver flange as the user opens their mouth and likewise pushes the driver flange into the slot of the maxillary piece as well.

One of the benefits of the removability of the protrusive flange and/or the driver flange is the ability to offer a kit having one or both of the maxillary piece and the mandibular piece having a removable flange and a plurality of said flanges to accomplish different amounts of anterior-posterior repositioning and cranial-caudal repositioning. In one embodiment, the kit has both a maxillary piece and a mandibular piece that have removably replaceable flanges, driver and protrusive flanges, respectively and a plurality of each flange in sets of protrusive and driver flanges to achieve different amounts of anterior-posterior repositioning and cranial-caudal repositioning.

In one embodiment, a plurality of left and right protrusive flange pairs are provided with the kit and at least one of the plurality of left and right protrusive flange pairs has a plateau of a preselected height between a base of each protrusive flange and a keyed slider extending caudally from the protrusive flange. The preselected height of the plateau prevents disconnect between each protrusive flange and its respective driver flange relative to a fully open mouth measurement between incisors of the user. Each protrusive flange engagingly saddles either a left backmost teeth mold or a right backmost teeth mold of the mandibular piece as part of its respective keyways described above against cranial movement. The plurality of left and right protrusive flange pairs differ in protrusive flange height ($H_{PF}$), angle, posterior side distance from the posterior terminus surface 876, and combinations thereof to provide differing effects to the user.

The kit can also include a plurality of left and right protrusive flange pairs having a post slidingly receivable in a slot in the maxillary piece. The plurality of left and right driver flange pairs differ in width, convex curvature of the anterior side, posterior lean, and combinations thereof to provide differing effects to the user. The width (W), labeled in FIG. 35, is measured at the apex of the convex curvature and is typically in a range of 5 mm to 11 mm (thereby allowing at least 1 mm width at the superior end of the flange). When this is 5 mm, the mandibular piece will be in CO/CR position i.e., 0 mm advanced position. When this is 11 mm, the mandibular piece is advanced by 6 mm. The 5 mm to 11 mm thickness also leaves sufficient width in the slot 902 of the maxillary piece for the post 900 to slide securely therein. The width is tailorable to provide a preselected amount of anterior advancement of the mandible of the user while in the at rest position.

Figure 37:
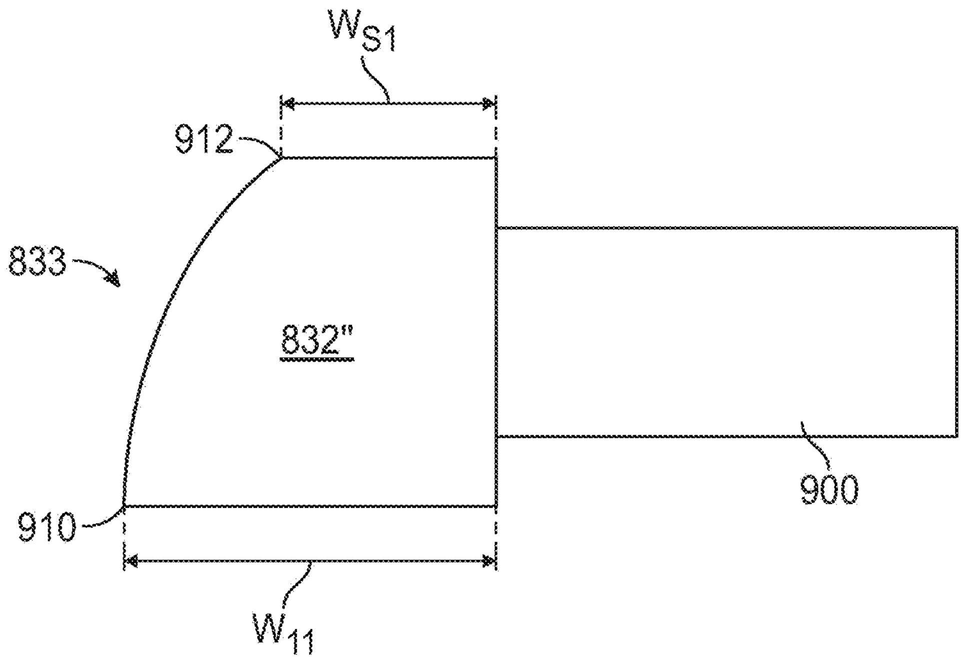
FIG. 37 is a side plan view of a second embodiment for the removable driver flange.
Figure 38:
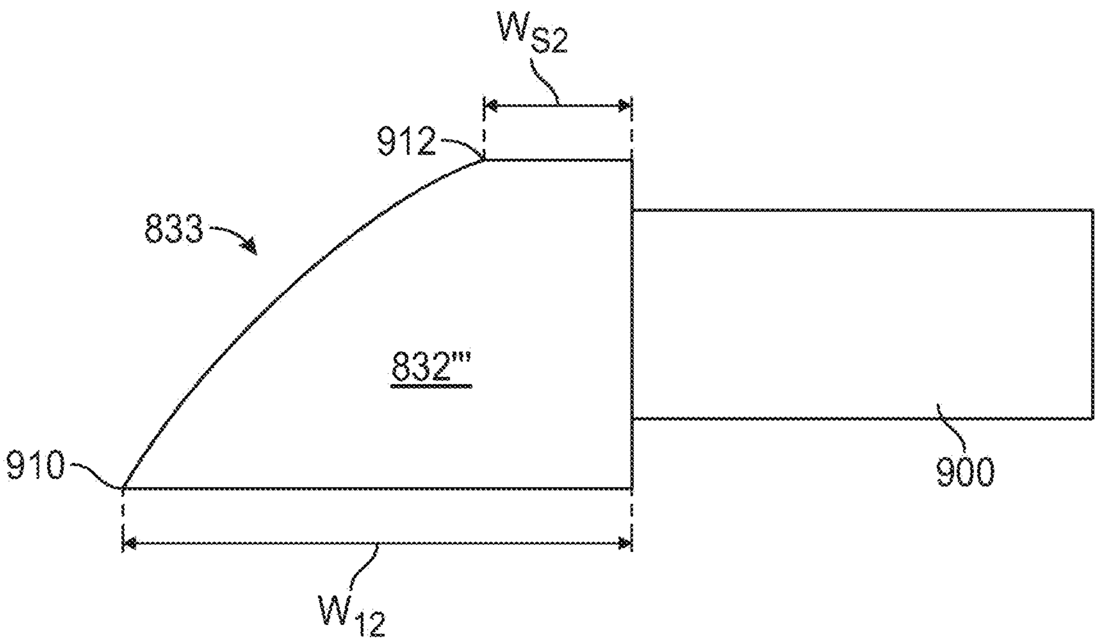
FIG. 38 is a side plan view of a third embodiment for the removable driver flange.

Differing posterior lean is shown in comparing the shape of the anterior side 833 of the driver flange 832', 832", 832"' of FIGS. 35, 37, and 38. FIG. 38 has an anterior side 833 with the most posterior lean. Here, the superior width ($W_{S2}$) is much smaller than the inferior width ($W_{I2}$) of the driver flange 833, thereby tilting the convex curvature of the anterior side 833 posteriorly as you move from the inferior base 910 to the superior cranial point 912 thereof. In contrast, the driver flange of FIG. 37 has the smallest (least) posterior lean. Here, the difference between the inferior width ($W_{I1}$) and the superior width ($W_{S1}$) is the smallest. The convex curvature can be increased, decrease, or adjusted with a preselected amount of posterior lean. Such changes to the convex curvature are selected to enable the mandible of the user to advance incrementally more with mouth opening. Less superior lean advances the mandible in the anterior direction less with each degree of mouth opening. In contrast, more superior lean advances the mandible in the anterior direction more with each degree of mouth opening. For example, the posterior lean in FIG. 37 may provide only a 1 mm anterior advancement with each degree of mouth opening, and the posterior lean in FIG. 38 may provide a 3 mm anterior advancement with each degree of mouth opening. The flange on the mandibular piece will also lean more or lean less to provide the best range of anterior and vertical mandibular advancement.

In one embodiment, one pair of the plurality of left and right protrusive flanges provides the user with a 6 mm anterior advancement of the mandible. This embodiment can also have a pair of the plurality of left and right driver flanges that provides the user with a 6 mm anterior advancement of the mandible, thereby providing a 12 mm net anterior advancement for the mandible in the rest position. As noted above, the pairs of flanges are typically mirror images of one another unless the user has a jaw or face asymmetry.

If the end user's activity would require, the removably replaceable protrusive flanges and driver flanges can include a fastener. The fastener can be a clasp, screw, snap fit, etc.

Figure 39:
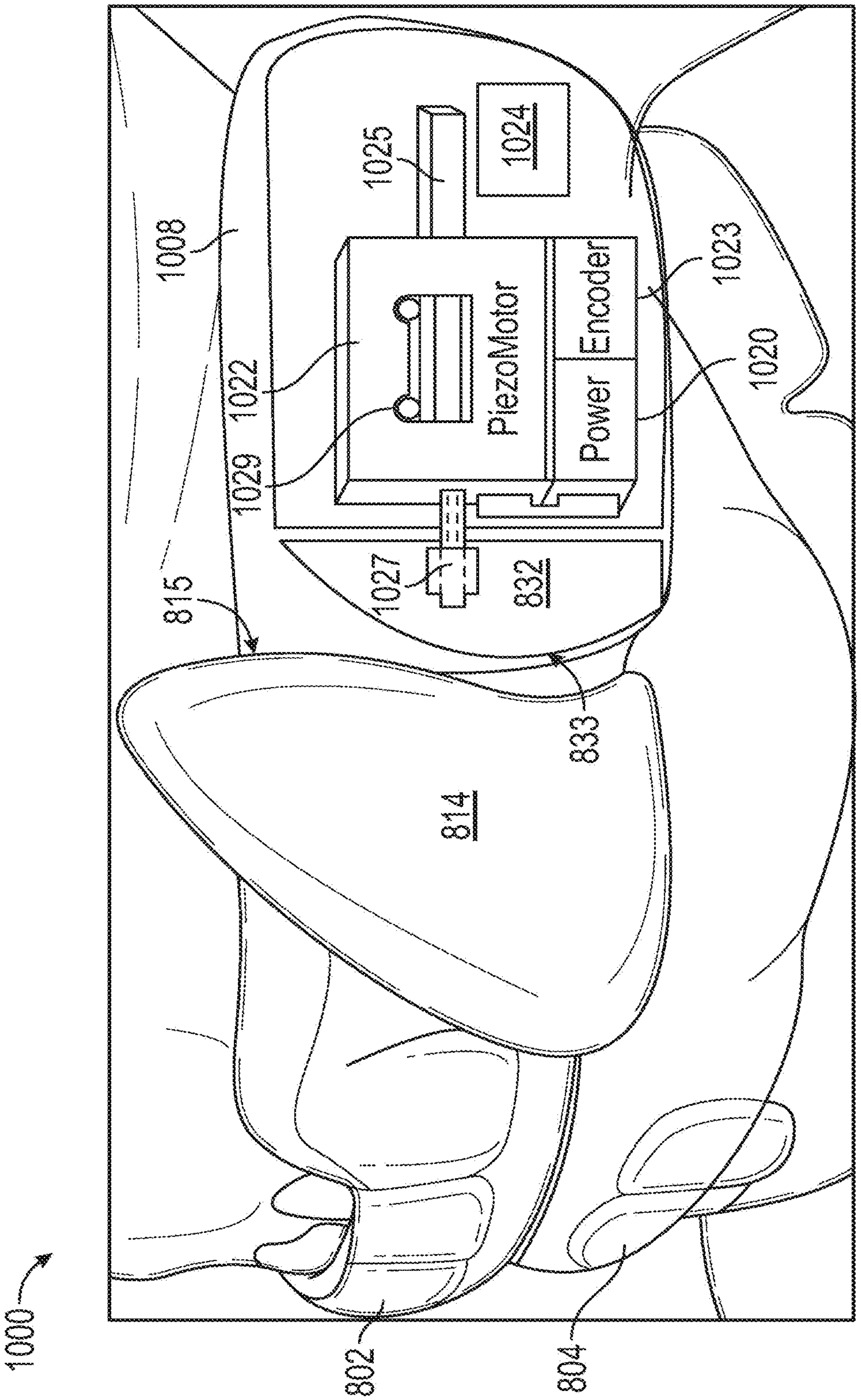
FIG. 39 is a left, side view of a first embodiment of the mandibular repositioning device having integrated anterior-posterior adjustment and cranial-caudal adjustment built into the maxillary piece.

Turning now to FIG. 39, an alternate embodiment to those in FIGS. 1-4 is shown that has both the anterior-posterior movement and the cranial-caudal movement of the mandibular repositioning device integrated into the maxillary piece 802 for control of the driver flange 832. The maxillary piece 804, on its buccal aspect, has a housing 1008 at each of the left and right molar portion, which each enclose, in a fluid-tight manner, a power source 1020 electrically connected to a piezo motor 1022 and to an encoder 1023 that controls the movement of a rod 1025 operatively connected to the piezo motor 1022 and to the driver flange 832. The power source 1020 is also electrically connected to a circuit board (microprocessor) 1024 that is in operative communication with the encoder and any of the sensor, stimulators, drug dispensers, etc. disclosed herein that are included in the maxillary piece. The rod 1025 encloses a set of robotic arms that move synchronously or opposite to each other (gliding together or sliding away from each other) driven mechanically, electrically, or electromagnetically by the piezo motor or electric and magnetic fields (EMF) generating coil that provides magnetic forces or mechanical forces to glide or slide the rod/arms. These are electric and magnetic fields (EMF) generated within using an EMF powered synchromesh and induction motor. Synchronous motors have an advantage of constant speed, steady load and operate with low voltage current or micro-voltage current. Absence of gearing gives them a smooth and quiet functionality that will be beneficial for this application. Induction motors have sustained torque and variable speed. Synchronous motors have pull up torque. Combination of these two facilitates movements starting after long periods of quiescence, continuous push-pull movements, and reversal of motor rotation. This creates the ideal combination that provides anterior and posterior, push-pull movements of the driver flange 832. A first arm drives the driver flange 832 anteriorly and posteriorly. A second arm drives the lean of the anterior surface of the driver flange. The distal end 1027 of the rod 1025 houses the two arm terminations into ball-socket terminals or other hinged terminals in the housing within driver flange 832. When both, maxillary and mandibular pieces are in place and a bite or clench is carried out or the flanges come in contact with each other or any form of trigger that will provide sensory activation of the device, such as activation through a handheld device, controller station or simply inserting all the relevant pieces into the mouth. Then the piezo motor activates (this provides the system with a signal that the device is installed in the oral cavity for use) and all components including the AVMLRD, handheld device, controller station, cloud-based repository of memory are activated. The system goes through a formal boot process and checks all components are functioning normally and live to go. The user gets a communication and then confirms active status of the system and finalizes activation. In the event that the user is incapacitated, next-of-kin followed by physician or EMS are notified in real time. It then moves the driver flange anteriorly using the first arm to bring the protrusive flange 814 to the prescribed position such as a Centric Occlusion or 1 mm to 6 mm advancement. In doing so, it clears room between the housing 1008 and the driver flange 832 that allows the second arm to perform prescribed posterior lean of driver flange 832. Both, the first arm and the second arm are actively moving back and forth (+ and – movements in their respective axes) during active operation and all movements are actively powered. The lean function allows the anterior leading edge of the driver flange 832 to maintain the prescribed lean and adjust the lean dynamically during use on an as needed basis.

The piezo motor 1022 in each housing 1008 is configured for three specific functions of the rod and the two arms within the rod. Cranial to caudal adjustments of the rod 1025 (i.e., first and second arms) through rotation around a central axis, anterior-posterior gliding of the rod (performed by first arm) and preferential sliding of the second arm perform the lean function. Alternately, the cranial to caudal adjustments is performed through movement of the entire piezo motor within the housing 1022 using a robotic armature, which is accomplished by the wheels 1029 positioned above the rod 1025. Caudal movement of the driver flange 832 enables the drive flange 832 to accompany the caudal movement of the protrusive flange 814 as the user opens their mouth and the reverse when closing their mouth. Alternately, driver flange 832 actively pushes the mandibular piece 804 caudally as the first arm anteriorly advances and the second arm leans posteriorly creating a positive pressure at the caudal anterior leading edge of the driver flange 832, nudging the trailing edge of the protrusive flange 814 and its caudal root to move caudally; thus, actively opening the user's mouth. This keeps the two flanges 814, 832 in constant contact with one another, thereby reducing the likelihood or possibility of a disconnect therebetween. The anterior-posterior movement and cranial-caudal movement directed by the piezo motor can occur simultaneously, individually, and/or sequentially.

The circuit board 1024 has a microprocessor comprising a quantum microchiplet and/or a photonic integrated circuit and nontransitory memory. While FIG. 39 shows the left housing 1008 with circuitry board 1024, the right housing will likewise include the circuit board and other components. The left and right circuit boards may have symmetric functions or shared functionality, communicating with each other continuously, and external controller, and/or other smart devices or through a two-way transmitter housed inside the protrusive flange 814. The microprocessor has stored in the nontransitory memory a first algorithm controlling the cranial-caudal movement of the piezo-electric motor relative to data receivable from one or more sensors. The sensors are typically in the oral cavity but are not limited thereto. The sensors can measure airway cross-sectional area, airflow volume, airflow velocity and pressure, airflow resistance, systolic and diastolic blood pressure, electrical activity of the heart, oxygen level, heart rate, and combinations thereof. The systolic and diastolic blood pressure and electrical activity of the heart may be measured by capacitive micro-machined ultrasound. Position sensors can be included that measure a first distance for cranial-caudal movement and a second distance for anterior-posterior movement of the driver flange.

The microprocessor has stored therein a second algorithm for anterior-posterior movement and lean functionality as described above. In one embodiment, the anterior-posterior movement is corelated to movement desirable when the user is under the influence such as effect of medication, sedation, anesthesia, or alcohol.

The microprocessor has artificial intelligence to learn from the collected data form the sensors when to make anterior-posterior and/or cranial-caudal adjustments to the driver flange and can do so before a measured parameter drops or moves out of a set range of values so as to maintain those values as close to the mean as possible and within a certain set of 1 to 6 standard deviations from the mean. In one embodiment, increasing airflow resistance, decreasing airflow volume, and decreasing cross-sectional area of the airway (SMCA) will immediately trigger the prescribed caudal and anterior movements through the first arm and required lean through the second arm thus moving the mandible and the tongue anteriorly and caudally at an incremental level desired with continuous feedback through the sensors. As airflow resistance drops, airflow volume increases and SMCA begins to increase, reverse movements of the first and second arms would result in raising the mandible cranially and simultaneously or sequentially retracting the mandible posteriorly.

Figure 40:
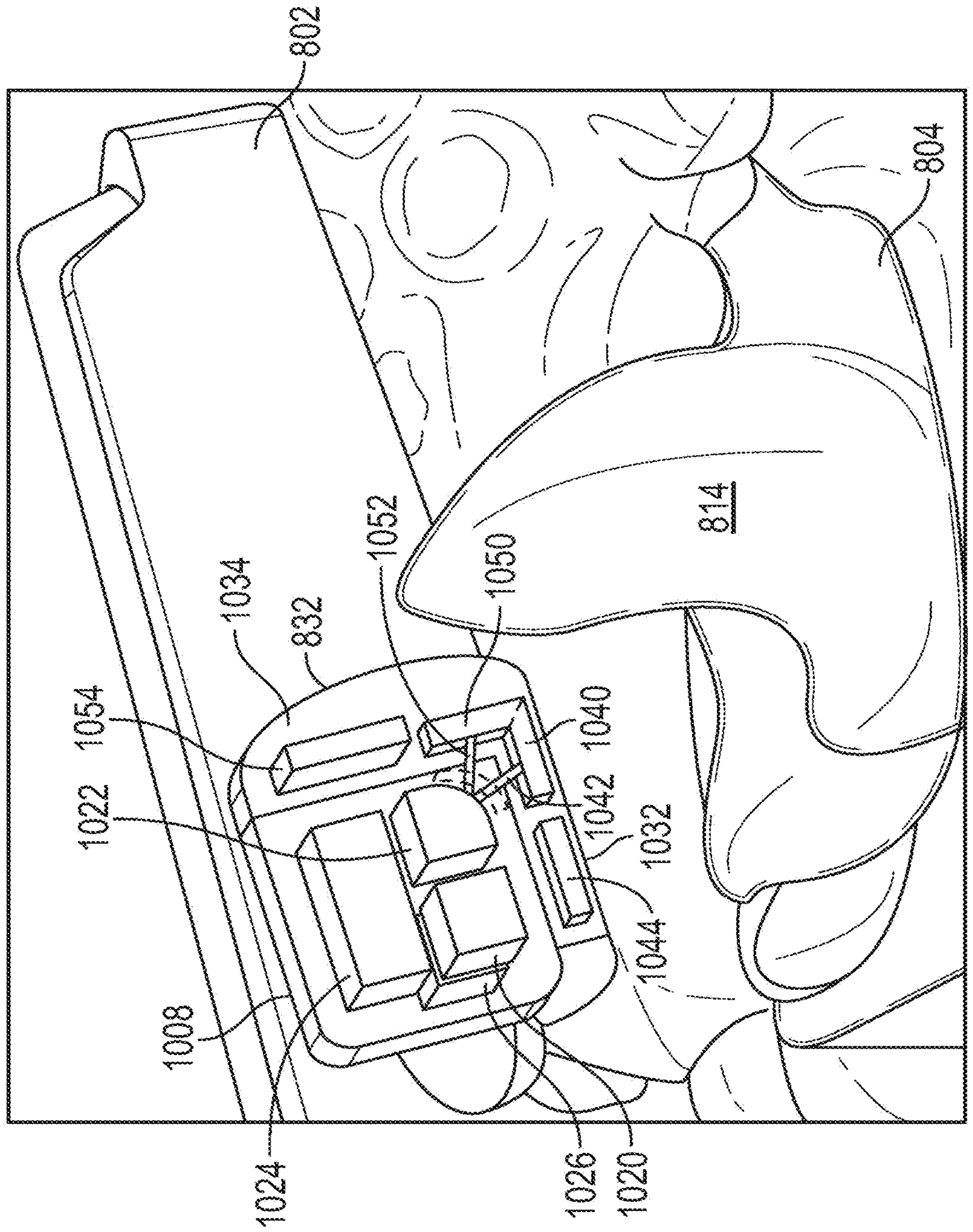
FIG. 40 is a right, side view of a second embodiment of the mandibular repositioning device having integrated anterior-posterior adjustment and cranial-caudal adjustment built into the maxillary piece.

Turning now to FIG. 40, another embodiment having anterior-posterior movement and the cranial-caudal movement of the mandibular repositioning device integrated into the maxillary piece 802 for control of the driver flange 832 is shown. The driver flange 832 has a posteriorly extending extension 1032 extending from the most caudal portion of the driver flange 832. The extension 1032 includes a first plate 1040 therein connected to a first robotic arm 1042 and a first position sensor 1044. The main portion 1034 of the driver flange 832 includes a second plate 1050 connected to a second robotic arm 1052 and a second position sensor 1054. The first plate 1040 is juxtaposed to the second plate 1050 at the junction of the extension 1033 to the main portion 1034 of the driver flange 832. The first plate and the second plate 1040, 1050 can be fixedly connected to move the entire flange together, such that the movement is more angular, thereby having both anterior-posterior and cranial-caudal adjustments simultaneously. In another embodiment, the extension 1033 may move independently from the main portion 1034 as represented by the dashed line in FIG. 40. The robotic arms, 1042, 1052 may be extending arms, such as telescoping arms, and terminate at their respective plates 1040, 1050 with an articulating joint, such as a ball and socket joint, for greater range of motion.

Figure 41:
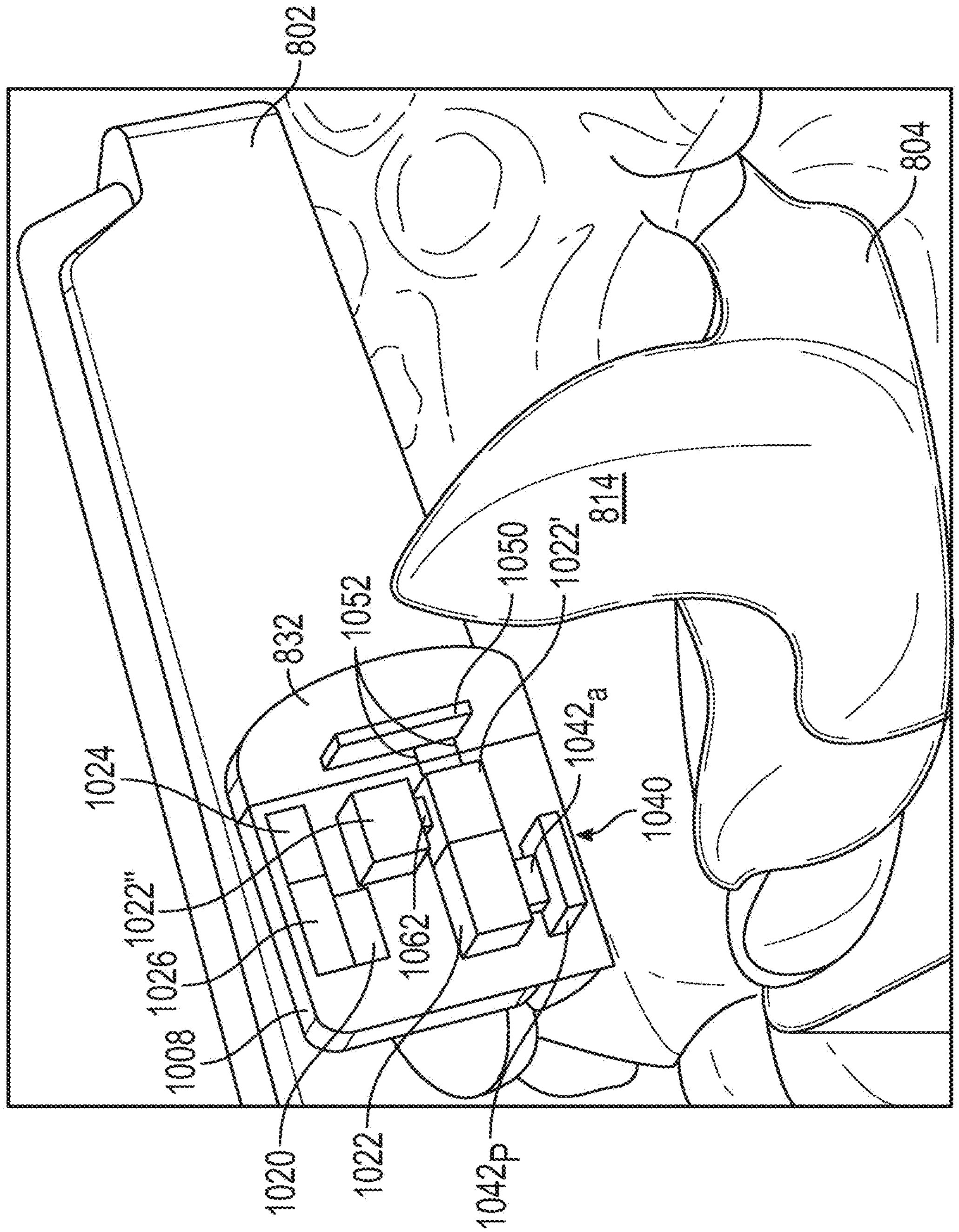
FIG. 41 is a right, side view of a third embodiment of the mandibular repositioning device having integrated anterior-posterior adjustment and cranial-caudal adjustment built into the maxillary piece.

The embodiments of FIGS. 40-41 have other features similar to the embodiment of FIG. 39, such as the microprocessor 1024 and memory 1026 for artificial intelligence control of the robotic arms 1042, 1052 relative to data from sensors, including the first and second position sensors 1044, 1054, even if not illustrated in the figures.

Turning now to FIG. 41, the first plate 1040 is separate from the driver flange 832 and is seated in the bottom of the housing 1008. The first plate 1040 has its own motor 1022 that is separate and independent form a second motor 1022' that controls the movement of the second plate 1052 which is positioned inside the driver flange 832. As indicated for the other embodiments, the arms connecting each motor to each plate may be extending, e.g., telescoping, and have an articulated connection to its plate, e.g., a ball and socket joint. Here, there is a third motor 1022''' present that is positioned with a third robotic arm 1062 to move the entire anterior-posterior assembly (second motor 1022', second robotic arm 1052, and second plate 1050) in the cranial-caudal direction, thereby moving the driver flange for cranial-caudal adjustments simultaneously, independently, and/or sequentially with anterior-posterior adjustments. As noted above, these adjustments may be used to maintain contact between the driver flange 832 and the protrusive flange 824 during caudal and anterior movement of the mandibular piece, thereby avoiding the cranial tip of the protrusive flange from dropping below the driver flange. This enables unrestricted mouth opening by the user.

In one embodiment of FIG. 41, dual robotic arms 1042 connect the first plate 1040 to the first motor 1022 and dual robotic arms 1052 connect the second plate 1050 to the second motor 1022'. The presence of dual robotic arms 1042, 1052 provides the ability to introduce a tilt to the driver flange 832 and/or the first plate 1040. For the driver flange 832, the tilt function can have the more caudally positioned arm move more than the more cranially positioned arm such that the effect of a greater posterior lean, such as in FIG. 38, is achieved, thereby providing more anterior advancement for each degree of mouth opening. Similarly, if desired, the opposite movement of the dual arms 1052 is possible to produces less posterior lean, such as in FIG. 37, thereby providing less anterior advancement for each degree of mouth opening.

Also, in the embodiment of FIG. 41, the dual robotic arms 1042 can move the posterior end of the first plate 1040 less than the anterior end of the first plate 1040. In one non-limiting example, for a mouth opening of 1 degree (1.66 mm) requires the posterior arm 1042$_p$ to move the posterior end of the first plate 0.95 mm and the anterior arm 1042*a* to move the anterior end of the first plate 1.06 mm. This can be used to introduce the equivalent of the plateau similar to those of FIG. 27-29 in the at rest position with dynamic alterations possible during activity or sleep through robotic and machine learning algorithms.

Each of the systems disclosed in FIGS. 39-42 has a power source 1020 that is rechargeable and has the recharging features described herein for other embodiments. Moreover, each system is compatible with the controller stations described herein and used artificial intelligence to drive the motor(s) 1022 and adjustments to the mandibular repositioning devices.

Figure 42:
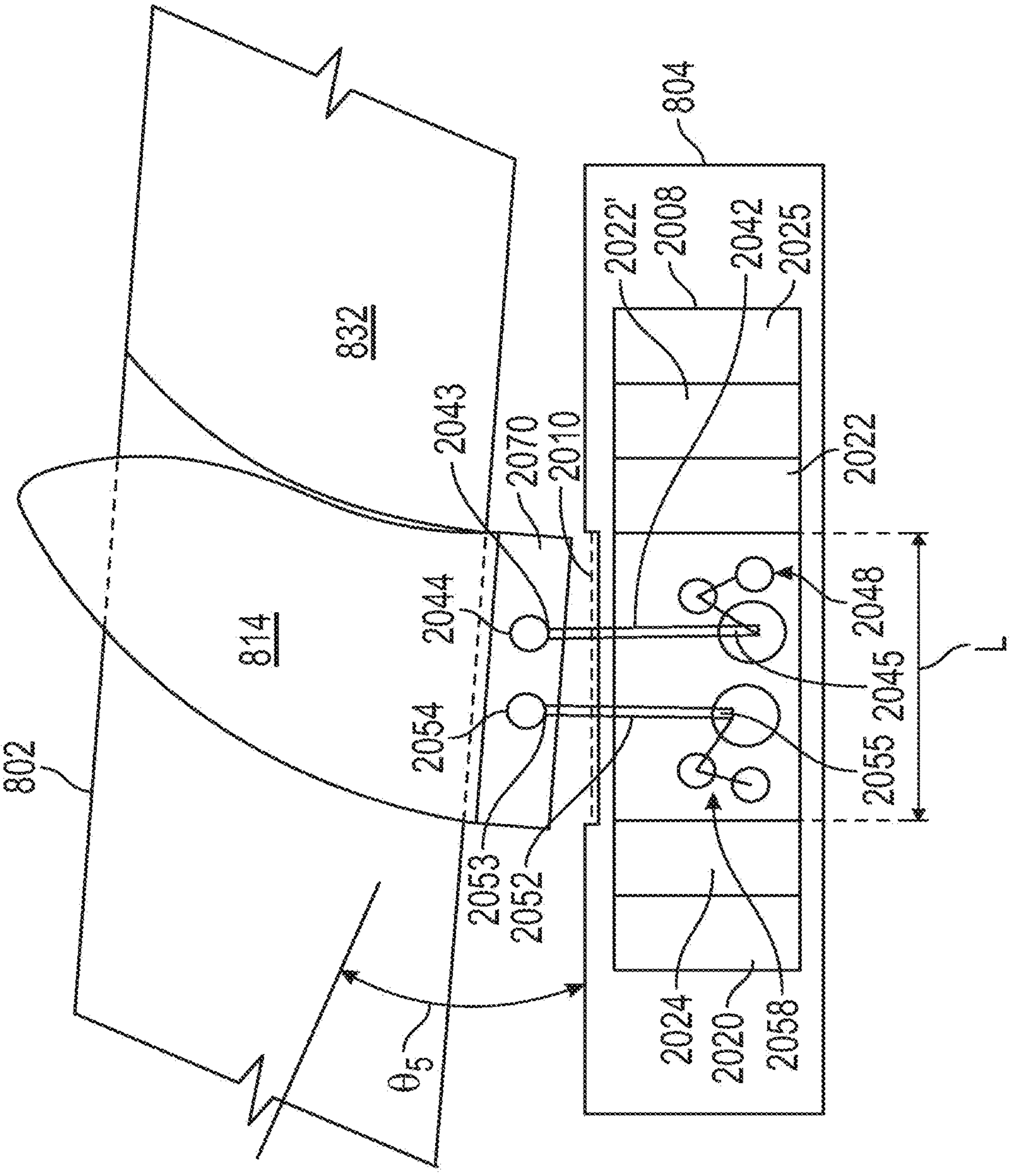
FIG. 42 is a side view sketch of a mandibular repositioning device having a robotically controlled and motorized adjustment mechanism built into the mandibular piece for movement of the protrusive flange and the plateau.

Turning now to FIG. 42, this embodiment has arms 2042, 2052 controlling movement of the protrusive flange 814 shown as the left molar region of the mandibular piece 804. The same is true for a right molar region. Each molar region has a housing 2008 of sufficient size to enclose electronics that accomplish anterior to posterior movement, cranial to caudal movement, and angular movement (05). For the anterior to posterior movement, the housing has a waterproof groove 2010 through which the arms 2042, 2052 extends. The length (L) of the groove is in a range of 1 mm to 12 mm, preferably 5 mm to 12 mm to provide a range of anterior to posterior advancement. A first end 2043, 2053 of each arm 2042, 2052 is connected to a respective receiver 2044, 2054 in the protrusive flange 814 at a position inside the base thereof or in a plateau 2070, if present, such as shown in FIG. 42. The receivers 2044, 2054 can provide a removably, replaceable snap-fit connection for changing the protrusive flange 814 or can receive a screw or other fastener. In one embodiment, the receivers 2044, 2054 facilitate a permanent attachment of the protrusive flange 814 to the arms 2042, 2052. When the plateau 2070 is present, it can have any of the features of the embodiments described herein.

The arms 2042, 2052 may be mechanically functional or may be robotic with artificial intelligence control thereof. The arms 2042, 2052 are juxtaposed to one another in an anterior to posterior relationship within the housing 2008. A second end 2045, 2055 of each robotic arm 2042, 2052 is operatively connected to a respective gear system 2048, 2058 that are individually controlled by a microprocessor 2024 within the housing 2008. The microprocessor 2024, a first motor 2022 and second motor 2022', power source 2020, at least one sensor 2025, and other optional electronics within the housing. The optional electronics can be any of the options discussed herein for any of the other embodiments. The individual control of the gear systems 2048, 2058 enables control of the arms 2042, 2052 simultaneously in synchronized or sequential operations or individually for any of the desired advancements for a particular patient's needs. The arms 2042, 2052 in any embodiment can have a removably, replaceable snap-fit to their respective gear system 2048, 2058. As such, arms of differing lengths can be provided and used as suitable for different conditions of the user, such as a change in physical activity or a change in health.

Still referring to FIG. 42, the mandibular repositioning device can include any number and type of sensors 2025 and stimulators from any of the embodiments disclosed herein and the microprocessor 2024 can execute necessary algorithms to achieve the anterior to posterior movement, cranial to caudal movement, and angular movement. The arms 2042, 2052 can provide up to 12 mm of anterior to posterior movement, up to 14 mm of cranial to caudal movement, and up to 25 degrees of angular movement ($\theta_5$) to the protrusive flange. To achieve the angular movement, the anteriorly positioned arm 2052 moves the protrusive flange more in the cranial direction than the posteriorly positioned arm 2042 as shown in FIG. 42. As discussed repeatedly herein, the anterior to posterior movement provides anterior mandibular and lingual advancement and the vertical and angular advancements provide caudal displacement of the mandible and tongue as well. In one embodiment, the microprocessor is a quantum microchip or a photonic integrated circuit, has non-transitory member, a renewable or rechargeable power source, a means to charge the power source, means for the microprocessors in each housing (right and left sides) to communicate with one another and/or external devices including those disclosed herein. Continuous machine learning will provide internal biofeedback and commands integrated with external resources. These embodiments for the protrusive flange are compatible with all other embodiments disclosed herein.

Referring back to FIGS. 1 and 4, at least one stimulator 116, but preferably both stimulators 116, include a first sensor 150L/R and/or a second sensor 152L/R, but preferably both sensors. 150L and 152L stands for the left side of the user and 150R and 152 R stands for the right side of the user. The sensors 150L/R and 152L/R may be selected from a variety of sensors to create which every combination is the most likely to be useful in diagnosing or treating the user. The sensors are selected form the group consisting of a pulse oximetry sensor, a vibration sensor, an airflow sensor, a pH sensor, a combination pulse oximetry/vibration and airflow sensor, an EKG sensor, EEG sensor, EMG sensor, EOG sensor, lactic acid sensor, a pulse transit time (PTT) sensor, an ultrasound sensor (echocardiography), an electro-oculogram sensor, a temperature sensor, a body position or jaw position sensor (such as a potentiometer), an electromyogram sensor, a pressure measurement sensor, a hygrometer sensor, a microphone or sound recording sensor, video recording, and hygroscopic/hydration sensor. In one embodiment the first sensor is a combination pulse oximetry/vibration and airflow sensor and the second sensor is a pH sensor. In another embodiment, the first sensor is a pulse oximetry sensor, and the second sensor is a vibration and airflow sensor. Any number of combinations of the sensors listed above is possible and can best be selected by a medical professional based on data relative to the pre-selected end user. Sensors in the left side and right side could be symmetric or complimentary or asymmetric. For example, CMUT/IVUS sensor may have better signal delivery and reception of carotid blood flow when placed on the left side and not as good a reading from the right side. Thus, it is placed only on the left side. The EKG sensor may have better reading from the right side than from the left side and thus is placed on the right side. Together, the EKG sensor and ultrasound sensor create complete cardiovascular hemodynamic data.

The stimulator 116 may also be accompanied by a sensor or sensors that can record EEG (electro-encephalogram), EOG (electro-oculogram), electromyogram (EMG) for the tongue muscles and NC (Nerve conduction) data from the nerves of the tongue, pharynx and muscles of mastication (jaw muscles) and phonation (speech). These sensors may transmit these data to the controller 200 (described in more detail below) through variety of industry standard wireless protocols that are currently in use for wireless EMG, NC and EEG recordings in other skin surface applications in neurology and sleep laboratories. Data from such sensors will be useful for detection of various medical diseases as it will be computed in time-synchronized manner by the controller 200 and cloud based servers in system 300 described in more detail below and will help to determine cause-effect of many medical diseases. The sensors will also provide feedback to controller 200 to gauge effectiveness of electric stimulation of the tongue or forward movement of the tongue and mandible and thus allowing the controller to make fine adjustments to all components of the system.

The length L of each stimulator 116 will be pre-selected to fit the user's mouth and tongue, in particular for adequate contact with the base of the tongue (genioglossus muscle) during sleep or while awake performing certain activities. While awake, the stimulator(s) can be used for muscle training or speech training or facilitation of swallowing mechanisms or for athletic performance enhancement. Each stimulator 116 has a single or dual electrode 154 or multiple electrodes or a large band of electrodes connected to the power source 120 and generates an electrical impulse that travels through the electrode to one or more of the lingual muscles of the tongue identified above, which contracts the lingual muscle(s) to create a forward movement of the tongue. The forward movement of the tongue increases the cross-sectional open airway diameter in transvers, vertical and antero-posterior dimensions, thus increasing the aggregate volume of open airway and exponentially reducing air-flow resistance. The power source for the single or dual electrode can be a direct current (DC) power source or may employ any other technology such as electro-magnetic energy, photon energy among other forms of energy. The electrical impulses' power source will be in volts or micro-volts and the current, likely in milli-Amps (usually 2-6 mA), will be pre-selected on a per patient basis. The power, current, and capacity will typically be within a range suitable for effective performance of mated hardware and safe for use with cardiac pacemakers, defibrillators, deep brain stimulators, or spinal cord stimulators.

The forward movement of the mandible (protrusion) is performed by lateral pterygoids, medial pterygoids and masseter muscles. These are stimulated by the mandibular branch of the trigeminal nerve. The neuronal firing rate drops during sleep relaxing these muscles causing the jaw to fall back (retrusion) and thus allowing the tongue to fall back (retro-glossal movement) into the airway as well creating a narrow airway which is the cause of obstructive sleep apnea, oxygen desaturation, elevated blood-pressure, cardiac arrhythmia, disruption in sleep and nocturnal acid reflux. The transverse stimulator 116 can specifically target these muscle groups and their distributing nerve and stimulate and sense electrical activity of these various muscles individually or together inside the oral cavity.

Also, the stimulators 116 can stimulate selected muscles to improve their strength. This can be a training or a retraining exercise, for example, after a stroke (swallowing difficulty or speech difficulty) or for children with speech pathologies. If sensors are present in the stimulators 116, the sensors can provide data to the controller station 200 and the system 300 of FIG. 11 to determine which muscle and/or muscle group needs attention. Thus, the shape of exterior surface/housing of the stimulators 116 are shaped and sized to direct each and every sensor, stimulator, or combination thereof to the appropriate location inside the oral cavity. Such a combination of sensors and stimulators will provide a pre-treatment evaluation file that can shape the strategy of treatment or performance improvements while simultaneously tracking the improvement resulting therefrom.

The pulse oximetry sensor 150 is positioned in one or both stimulators 116 at a position enabling direct contact with the base of the tongue from which data will be collected. The position of the pulse oximetry sensor 150 is generally antero-superiorly positioned for measuring pulse-oximetry through the blood-flow of the tongue. The vibration and airflow sensor 152 is positioned in one or both stimulators 116 at a position suitable for airflow measurements, which can indicate when there is a restriction of airflow, and vibration measurements (sub-sonic and sonic) that are an indication of inaudible and audible snores and speech detection or cough as well. The vibration and airflow sensor 152 faces posteriorly to measure snores and airflow resistance/pressure from the airway.

The power source 120, 121 in all embodiments may be a rechargeable battery. In one embodiment, the rechargeable battery is one or more micro-lithium ion batteries in each housing 108, 109. Solar/light charging energy source that can be recharged by ambient lighting (used in the watch maker industry) or solar power may also be considered for a rechargeable source of energy. The rechargeable battery may have a maximum discharge milli-amperage creating a mechanical mandibular protrusion or retrusion ranging between 1-10 mm in linear dimensions for the movement of the drivers 130, 132.

As seen in FIGS. 1 and 2, each housing 108, 109 of the mandibular and maxillary pieces, respectfully, include a charging member 118, 119, such as a charging plate, in an exterior surface thereof. In the figures, the charging plate is in a lateral side of the housing 108, 109, but is not limited thereto.

As best seen in FIG. 3, the first driver 130 may be a flat plate connected to the motor 122 by the linkages 134.

The motor 122, 123 in all embodiments may be a single or dual piezoelectric motor having a linearly movable linkage(s). Micro motors based on piezo electric materials are commercially available from Piezo Motor, a company headquartered in Sweden and may be modified as needed for use in the disclosed devices. The motor 122, 123 may include a position sensor.

As best seen in FIGS. 3 and 6, the maxillary piece 102 sits on the mandibular piece 104 with the first driver 130 operatively engaged with the maxillary piece 102 and the second driver 132 operatively engaged with the protrusive flange 114, 114', or 114" of the mandibular piece 104. Each of the drivers 130, 132 can move the jaws in increments of 0.1 mm up to 2 mm with each movement with a maximum of 12 mm in the respective direction. The protrusive flange 114, 114', 114", is moveable by the second driver 132 in a range from 0.1 mm to 11 mm and the first driver 130 can lift the maxillary portion in a range from 0.1 mm to 12 mm.

Referring again to FIG. 6, the second driver 132 has a head 136 that is shaped to fit the shape of the posterior side 145 of the protrusive flange 114'. The head 136 has a convexly-shaped anterior side to press against the posterior side 145 of the protrusive flange 114'.

Figure 9:
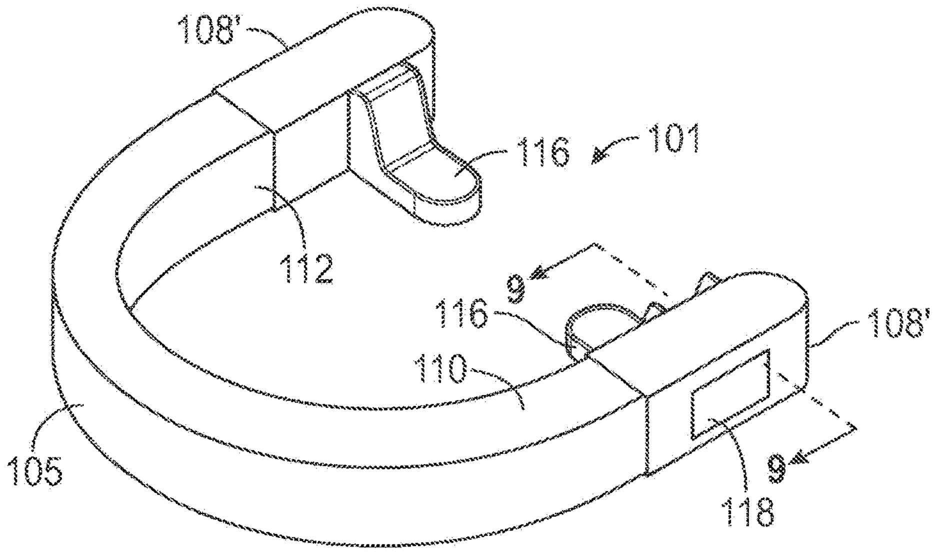
FIG. 9 is a side, perspective view of an embodiment of a mandibular device having at least a stimulator electrode therein.

Turning now to FIG. 9, a mandibular device 101 is illustrated that has just the stimulator 116 and a mandibular teeth covering 105. As such, the maxillary piece can comprise of a teeth covering 107 as shown in FIG. 2 without the housings 109 or be absent, i.e., the user can just have the mandibular device 101 in their mouth during use. Dual housings 108' are present with one each proximate a left molar portion 110 and a right molar portion 112. A stimulator 116 extends from each housing 108' toward the tongue at a position to lie under the tongue in contact with lingual muscles, in particular the Genioglossus (GG), the Geniohyoid (GH), sub-mentalis (SM), and Glossopharyngeal (GP). Each housing 108' includes a charging feature 118 for recharging any battery(ies) housed therein, as described above.

Figure 10:
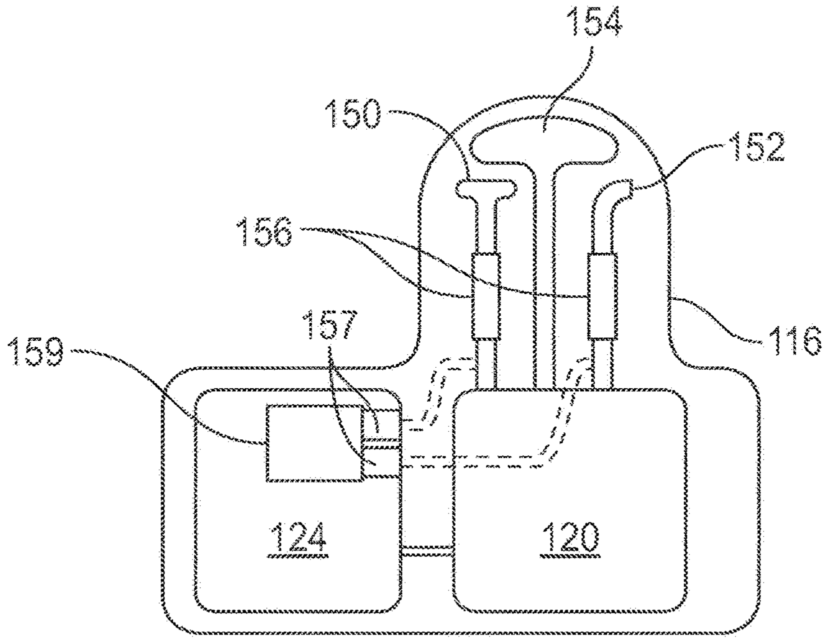
FIG. 10 is an enlarged cross-sectional view of the mandibular device along line 9-9 in FIG. 9.

Referring now to the cross-section of FIG. 10 through one of the stimulators 116, each stimulator 116 houses therein, in a fluid-tight manner, a first sensor 150, a second sensor 152, and a stimulator electrode 154. In FIG. 10, the first sensor 150, the second sensor 152, and the stimulator electrode 154 are each electrically connected to the power source 120 within housing 108'. The electrical connections may be direct connections to the power source 120, which may be accomplished by a plug-n-play electrical connector 156, or, as represented by the dashed lines, may be accomplished by a plug-in style connector 157 to the microprocessor 159 and thereby to the power source.

In one embodiment, the first sensor 150 is a pulse oxygen sensor continually measuring oxygen data at the base of the tongue and the second sensor 152 is a vibration/air flow sensor measuring snoring, turbulent flow, and vibrations from inside the user's mouth. As noted above with respect to FIG. 4, multiple other sensors and sensor combinations are possible that will provide data to the microprocessor 159. The circuit board 124 within the housing 108' is in operative connection to the power source to be powered and to control activation of the stimulator electrode 154 in response to data received by the circuit board 124, more particularly, the microprocessor 159, from the first sensor 150 and/or the second sensor 152. As discussed, the microprocessor 159 receives the sensor data, processes the sensor data, and determines whether the stimulator electrode 154 needs activated.

Each of the stimulators 116 may include a pH electrode too. The pH electrode will measure the acidity at the back of the tongue, which if too high is an indication of chronic high acid reflux.

Figure 11:
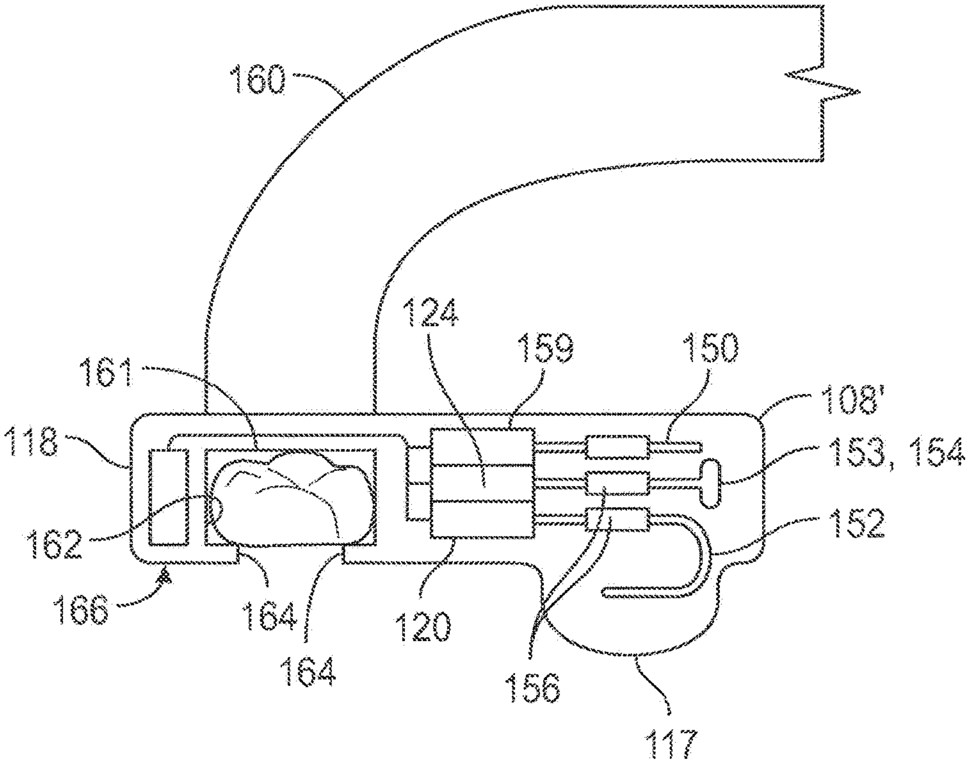
FIG. 11 is a cross-sectional view of another embodiment of a mandibular device that is removable attachable to a teeth covering.

Referring now to the FIG. 11, which is a transverse cross-section through one of the stimulator/sensor protrusions 117 and housings 108' of a mandibular device similar to the mandibular device 101 of FIG. 9. In this embodiment, each housing 108' and stimulator/sensor protrusion 117, rather than being built as part of the teeth covering 160, are removably attachable to the teeth covering 160. Each housing 108' defines a groove 162 shaped to receive therein an end 161 of the teeth covering 160, such that one housing 108' is removably attached to a first end 161 defining a left molar portion and the other housing 108'(not shown) is removably attached to a second end (not shown) of the teeth covering 160 defining a right molar portion thereof. The groove 162 may have opposing flanges 164 positioned at and parallel with a bottom surface 166 of its housing 108' and extending toward the open void defined by the groove 162. The groove 162 of each housing 108' may be slid over and be received on the teeth covering, may have a snap fit to the teeth covering, may have an interference fit, or may be fabricated in two parts that can snap into each other over a predetermined location of the teeth covering or may be fabricated with three-dimensional printing over a teeth covering. The illustrated embodiment in FIG. 11 has the housing 108' slidingly received on the first end 161 of the teeth covering 160 with the flanges 164 resting against bottom surfaces of each of the sides of the teeth covering 160. Regardless of the type of attachment, each housing 108' is movable fore and aft to adjust the position of the stimulator/sensor portion under the correct position under the tongue of the user.

Since the housings 108' are removably attachable to the teeth covering 160, each housing and or teeth covering may be disposable or reusable. When the housings 108' are reusable, the housings are constructed of a material suitable for sterilization between uses, such as by autoclave sterilization. Housed within each housing 108', in a fluid-tight manner, is a first sensor 150, and an optional second sensor 152, and an optional third sensor 153 or a stimulator electrode 154 or even a high-pressure pellet discharge system. Each of the first sensor 150, the second sensor 152, and the third sensor 153 or the stimulator electrode 154 are electrically connected to the power source 120. The electrical connections may be direct connections to the power source 120, which may be accomplished by a plug-n-play electrical connector 156, or may be accomplished by a plug-in style connector to the microprocessor 159 and thereby to the power source 120. The housings 108' each include a charging member 118 in an exterior surface thereof for coordination with one of the charging units 202, 204 of the controller station 200 of FIG. 5.

In one embodiment, only the first sensor 150 is present. The first sensor 150 may be, but is not limited to, a pulse oxygen sensor, a vibration and airflow sensor, a pH sensor, a doppler ultrasound, an M-Mode ultrasound, a 2D ultrasound, 3D ultrasound, a pressure plate for measuring bruxism, a pulse transit time sensor, non-invasive ventilation systolic/diastolic blood pressure sensor, a carotid doppler (trans-oral) sensor, or a cardiac trans-oral echocardiography sensor or a camera/videography system, or any other sensor identified herein. In one embodiment, the first sensor 150 is a pH sensor. In another embodiment, the first sensor 150 is a pulse oxygen sensor continually measuring oxygen data. The mandibular device 101 is used with the controller station 200 in a diagnostic mode.

Since there are two housings 108' each having a stimulator/sensor protrusion 117, each housing 108' may have a different type of sensor for the first sensor 150 or one may have a first sensor 150 and the other may have the stimulator 154. As such, the mandibular device 101 can be used in a diagnostic mode or a treatment mode depending upon the selection of sensors and/or stimulator in the housings 108', thereby providing great versatility in use. Furthermore, since the housings 108' are removable attachable to the teeth covering 160, the housings 108' can be switched for housings having different sensors in a sequence of nights to assess various parameters of the user or during the day or both night and day. The mandibular or maxillary housings or teeth coverings, when used alone (mandibular or maxillary) should allow most speech functions and thus can be used during the course of a normal day. The data interfaces with standard Bluetooth functionality or WIFI functionality and the controller station may be used as a mobile unit with Bluetooth and WIFI functionality and as such may be carried to work or elsewhere since it has its own rechargeable battery operations. Controller station will be interfaced with proprietary or open platform program that can be securely loaded on variety of computer systems and hand-held smart devices.

Figure 12:
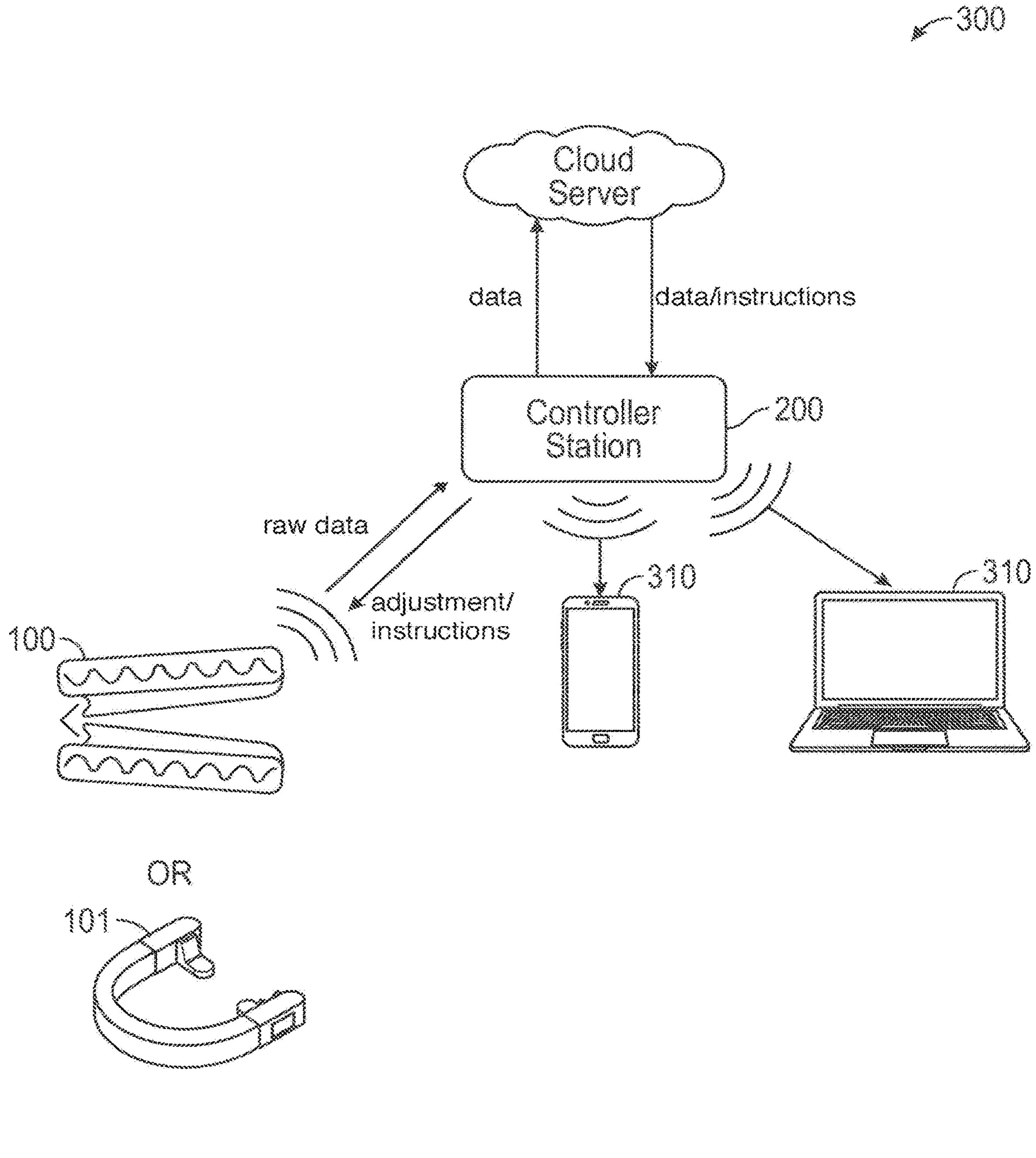
FIG. 12 is a schematic illustration of a system in operative communication with the MRLD of FIG. 1 or the mandibular device of FIG. 8.

In another embodiment, the first sensor 150 in a first of the housings 108' is a pulse oxygen sensor continually measuring oxygen data at the base of the tongue and the second sensor 152 is a vibration/air flow sensor measuring snoring, turbulent flow, and vibrations from inside the user's mouth; the second of the housings 108' has a pH sensor as the first sensor and includes the stimulator 154. Here, diagnostic and treatment functions are possible that are coordinated by the system 300 or any of its components such as controller or PC or smart device. The sensors 150, 152 provide data to the microprocessor 159. The circuit board 124 within the housing 108' is in operative connection to the power source to be powered and to control activation of the stimulator electrode 154 in response to data received by the circuit board 124, more particularly, the microprocessor 159, from the first sensor 150 and/or the second sensor 152 and/or from instructions from the controller station 200 and/or the cloud server as shown in FIG. 12 (described in more detail below) to effect a treatment. For example, if the pH sensor senses an increasing acid condition as the user sleeps and the other sensors measure airflow resistance or decreased airflow, then the stimulator will be activated to open the airway and the system will then determine if the pH decreases. Such a causal relationship may help reduce/prevent significant nocturnal acid reflux and thus minimize or eliminate the use of acid reflux medications. Moreover, the combination of sensors can be selected to determine time synchronization of the pH to other physiological occurrences of the user, such as body position, inspiration, expiration, sleep measurements, oxygenation, bruxism, snoring, apnea, etc. Ideally, a link between acid reflux and other physiological occurrences can be determined and then used for treatment.

Moreover, using the controller station 200 and cloud server of the system 300, it will be possible to receive data regarding the user's input of food and time consumed to act proactively during sleep based on a correlation of digestion time and acid reflux onset. This capability may be extended to input of any and all medications, physiological data such as BP, EKG and blood sugar, and to administering of any and all medications during the day (prompted to the user through handheld device) or night (automatically performed if pressure pellet for medication is available to the system to discharge sub-lingually or intra-orally in liquid form or inhaled as micro-aerosol powder form.

The teeth covering 160 in the embodiment of FIG. 11 can be as simple as a plastic boil and bite mandibular device onto which the housings 108' are removably attachable. In this manner, the teeth covering 160 is disposable and are readily available. Other teeth coverings 160 are commercially available that are generally cheap and disposable such as ora-guard, sonabul, oral-b etc. However, the teeth covering 160 is not required to be disposable. Instead, the teeth covering 160 can be constructed of a material that is sterilizable such that the teeth covering is reusable by a user or users over a preselected time period while sterilizing the housings 108' and utilizing any combination of housings 108' having a variety of sensors to monitor as many physiological parameters of the user as selected by administering expert.

Figure 13:
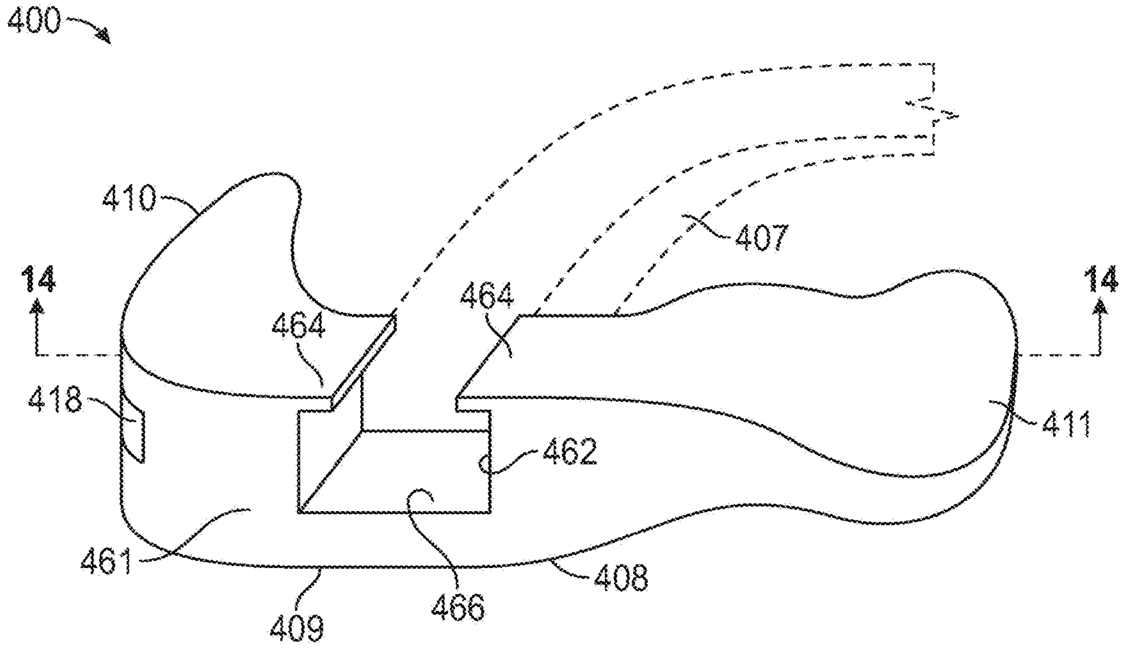
FIG. 13 is a rear, perspective view of a maxillary device having at least a stimulator electrode therein.
Figure 14:
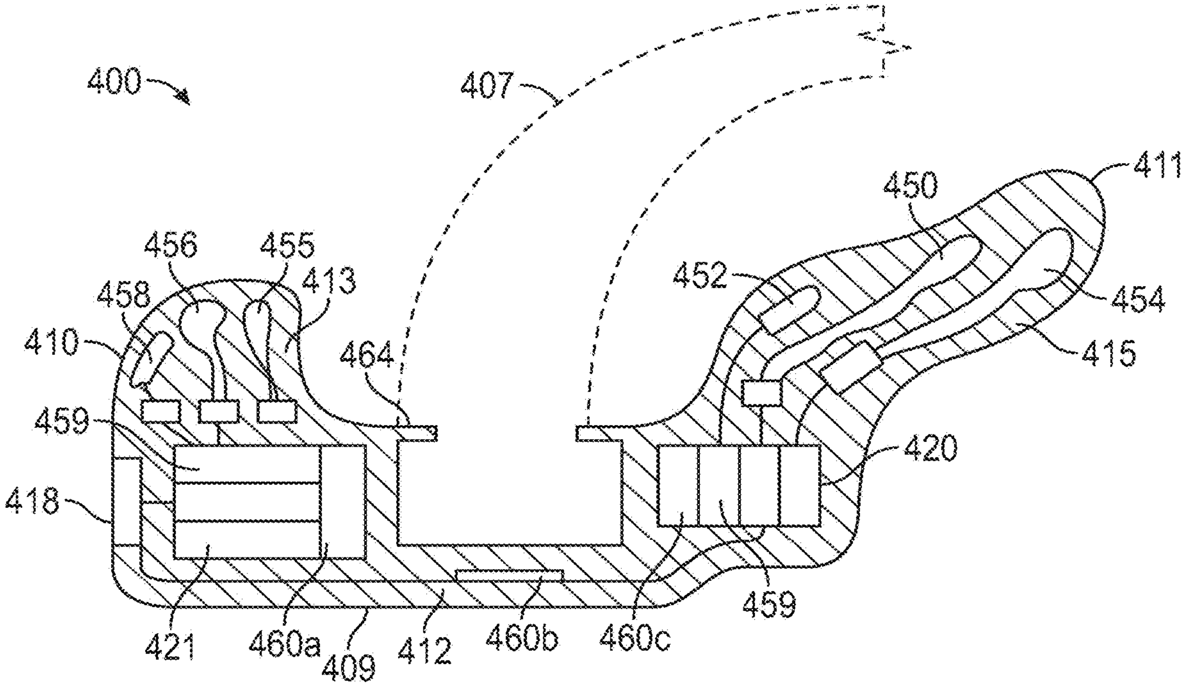
FIG. 14 is a cross-sectional view along line 14-14 of FIG. 13.

Turning now to FIGS. 13 and 14, a maxillary device 400 that is either integral with a teeth covering 407 or removably attachable to the teeth covering 407 is shown. A teeth covering includes a palatal expander or retainer device as well as mouthpiece covering the teeth. Teeth covering 407 may have one maxillary device 400 at the left molar portion and a second maxillary device (the mirror image of the maxillary device 400 in FIG. 13) at the right molar portion or places asymmetrically for individualized needs. Each maxillary device 400 has a housing 408 that defines a tooth connecting portion 409 one or both of a buccal housing 410 and a palate housing 411 that each define an internal cavities 412, 413, 415, respectively, in which is housed, in a fluid-tight manner, a stimulator electrode 454, 455 and/or one or more sensors 450, 452 and/or other data collecting devices 456.

The buccal housing 410, when present, is shaped to fit between the user's teeth and cheek and may extend anteriorly and/or posteriorly to collect data and/or stimulate muscles within the oral cavity. The buccal housing 410 can stimulate the lateral pterygoid muscles to move the jaw forward. The jaw may be moved forward during sleep or while awake. While awake, the stimulator 455 can coordinate muscles of mastication or swallowing.

The palate housing 411 is shaped/contoured to rest against the roof of the user's mouth in contact with the hard palate and the soft palate and clings to the surface of the mucosa in the mouth in order to have good contact for purpose of stimulation of the muscles of swallowing and of the soft palate. The palate housing 411 extends in any possible direction to acquire physiological data from the oral cavity and to stimulate the lateral pterygoid muscles for protrusive movement of the mandible or stimulate muscles of the soft palate and uvula so as to stiffen these structures to reduce snoring or for detection and treatment of speech or swallowing pathologies. The speech or swallowing pathologies may include, for example, post-stroke recovery or reconstructive surgery of the maxilla-facial region recovery or short frenulum syndrome with associated speech defects or micrognathia syndrome in children such as is seen in pediatric obstructive sleep apnea or in Treacher-Collins syndrome.

Each housing 408 includes a charging feature 418 in an exterior surface thereof for recharging any on-board power source 420, such as battery(ies), housed within the internal cavities 413, 415 or in any portion of the maxillary or mandibular device, even in remote parts of the device, i.e., there is no requirement for the batteries to be adjacent to the location of sensors. The batteries may be any of those discussed above with respect to other embodiments.

In FIG. 14, the housing 408 includes a photography and/or videography array 460 having photography and videography units 460*a*, 460*b*, 460*c* positioned to face each side and a bottom of a tooth, respectively, as shown in FIG. 14. The photography and/or videography array 460 can include, but is not limited to, unidirectional or multidirectional collection using single or multiple digital cameras to map dental structure, oral cavity structure, airway structure etc. and record sounds. When intended to map the oral cavity or airway structure, the unidirectional or multidirectional units are oriented outward toward the oral cavity rather than toward a tooth. These photography/videography arrays may be used to create recordings of teeth and gums (maxillary or mandibular) for use in general dentistry, endodontic and periodontal applications such as fabrication of enamel, measurement of enamel wear in bruxism, artificial teeth construction, crown construction, gum disease detection and treatment, and for 3-D printing of the mandibular and maxillary devices disclosed herein. When the photography/videography arrays face a tooth, the housing 408 may be configured to slide back and forth over the teeth to create a video or photo recording thereof for dental use. The housing 408 may attached to a wand or a fiberoptic flexible wand that can be manually moved along the teeth by the dentist or physician to help take images of single or multiple teeth or the complete dentition for dental applications or MRD (mandibular repositioning device) construction applications.

The stimulator electrodes 454, 455 are as discussed above for other embodiments. The sensors 450, 452, 456, 568 include any and all of the sensors discussed above for other embodiments. One of the sensors can be a sound sensor to collect sounds such as those during sleep (e.g., snoring or grinding of the teeth) or those related to speech and swallowing that may be useful to define specific speech defects and swallowing defects. All these functions may be stand-alone or in synergy with stimulators, mandibular and/or maxillary movement devices, videography, photography, etc.

In FIG. 14, the first sensor 450, the second sensor 452, and the stimulator electrode 454 are each electrically connected to the power source 420 within the palate housing 411. Likewise, a third sensor 456, a fourth sensor 458, and the stimulator electrode 455 are each electrically connected to the power source 421 within the buccal housing 409. The electrical connections may be direct connections to the power source 420, 421 which may be accomplished by a plug-n-play electrical connector or may be accomplished by a plug-in style connector directly to the microprocessor 459 and thereby to the power source 420, 421.

In the removably attachable embodiment of FIG. 13, the housing 408 defines a groove 462 shaped to receive therein an end 461 of the teeth covering 407. A first housing 408 is removably attached to a first end 461 defining a left molar portion and a second housing, if present, is removably attached to a second end (not shown) of the teeth covering 407 defining a right molar portion thereof. The groove 462 may have opposing flanges 464 positioned at and parallel with a bottom surface 466 of its housing 408 and extending toward the open void defined by the groove 462. The groove 462 of the housing 408 may be slid over and be received on the teeth covering, may have a snap fit to the teeth covering, may have an interference fit, or may be fabricated in two parts that can snap into each other over a predetermined location of the teeth covering or may be fabricated with three-dimensional printing over a teeth covering. It may be designed to fit directly over the teeth in the absence of any other teeth covering. In this embodiment, the housing 408 will be a teeth covering itself. The illustrated embodiment in FIG. 13 has the housing 408 slidingly received on the first end 461 of the teeth covering 407 with the flanges 464 resting against bottom surfaces of each of the sides of the teeth covering. Regardless of the type of attachment, housing 408 can be movable fore and aft to adjust the position of the stimulator/sensor portion to engage the stimulator 454, 455 with a preselected muscle.

The housing 408 can be molded from suitable plastics or built with 3-dimensional printing, especially after photographic/video graphic impressions are made of one or all teeth, for example with a system such as Carestream dental imaging. These images can be used to make the housing 408 a single tooth just like putting on a temporary crown. This would be a removable, disposable or reusable option.

Figure 15:
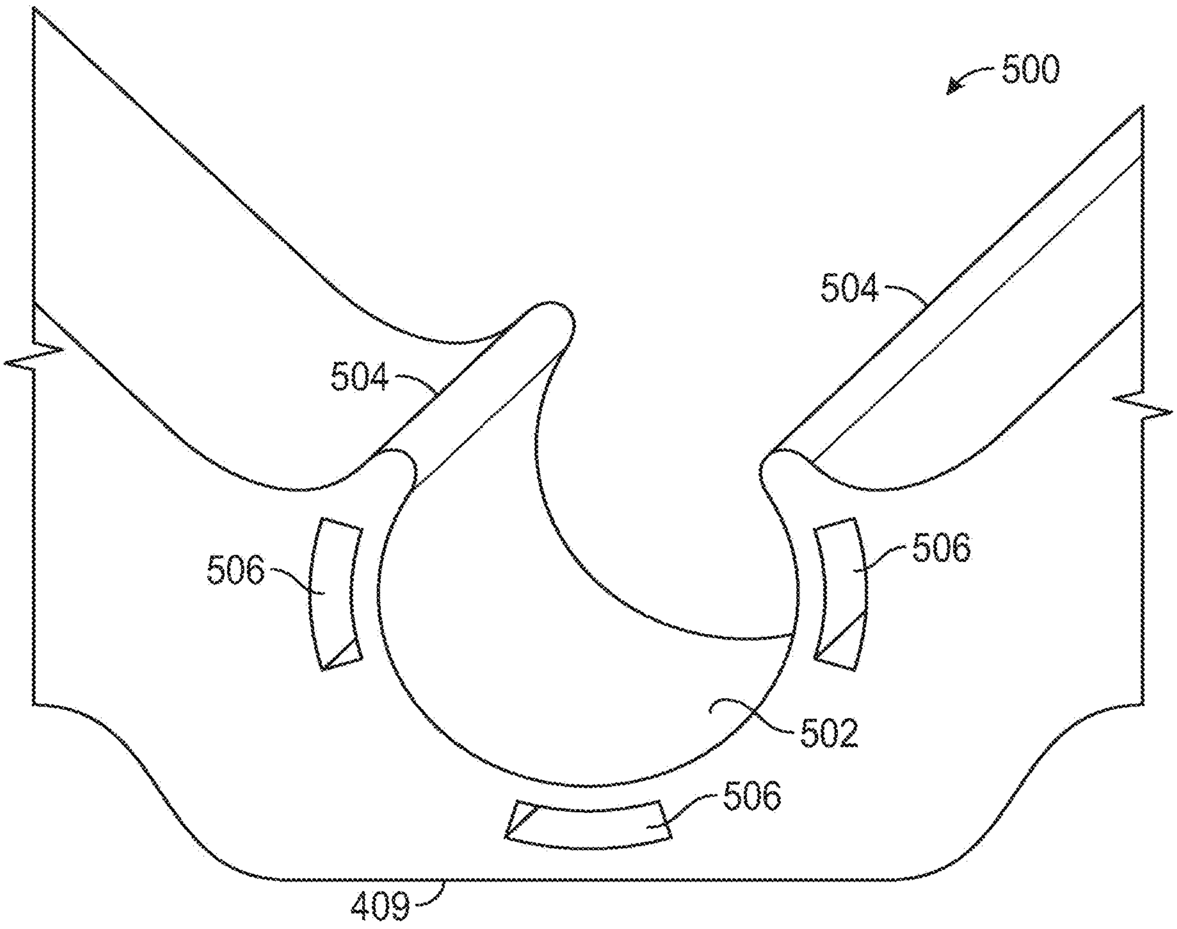
FIG. 15 is an enlarged view of a second embodiment of a connecting portion of the maxillary device.

Turning now to FIG. 15, an alternate embodiment of the tooth connecting portion 409 of housing 408 is shown. Here, the tooth connecting portion 409 defines a clasp 500 that is elastically deformable to fit over a single tooth or a plurality of teeth. The clasp 500 defines an arcuate shaped opening 502 that receive a tooth or teeth therein and has opposing teeth side flanges 504 that seat against opposite sides of the tooth/teeth or gums. The clasp 500 is made of an elastic material that will stretch open as it is fitted over a tooth/teeth and will then return to its original position for a tight fit against the tooth/teeth or gums. To enhance the elastic flexibility of the clasp 500, the body defining the arcuate shaped opening 502 can include a plurality of elongate, slightly arcuate bores 506 passing through the body in a juxtaposed arrangement to the arcuate shaped opening.

Figure 16:
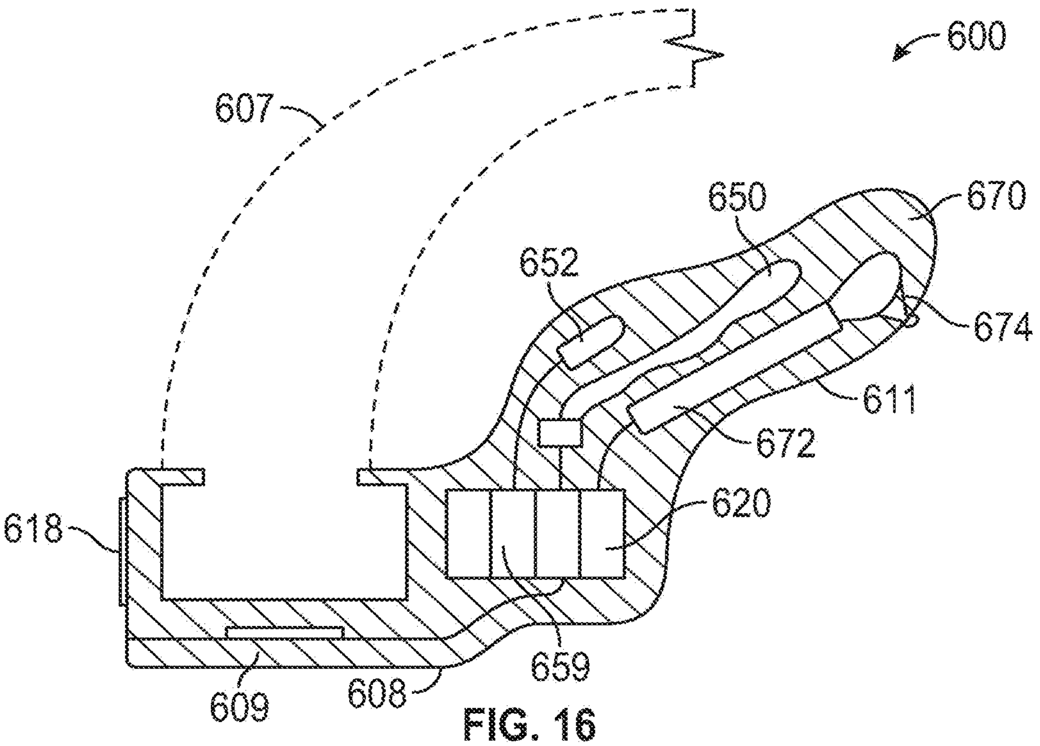
FIG. 16 is a longitudinal cross-sectional view of an embodiment of a maxillary device having a medicament dispenser.

Turning now to FIG. 16, a maxillary device 600 is shown that includes a medicament dispenser 670, but it could just as easily be any of the mandibular devices disclosed herein. The maxillary device 600 has a housing 608 connectable to a tooth of a user or connectable or integral with a teeth covering 607. The housing 608 encloses an on-board circuit board 659 and a power source 620 and comprises a tooth connecting portion 609, a palate housing portion 611 extending from the connecting portion, and a charging feature 618 in an exterior surface thereof for recharging the on-board power source 620. The palate housing portion 611 encloses therein a first sensor 650, and optional second sensor 452, and a medicament dispenser 670 each in electrical communication with a microprocessor of the on-board circuit board 659. The on-board circuit board 659 receives data from sensors 650, 652 and activates the medicament dispenser 670 to dispense a medicament to a user's oral cavity as needed under pre-selected conditions.

The medicament dispenser 670 includes a reservoir housing 672 the medicament (i.e., a plurality of doses), which can be in pellet, tablet, powder, or liquid form, and a dispenser head 674 open or openable for communication with the oral cavity. The reservoir 672 is either refillable or removable replaceable with a filled reservoir. The reservoir 672 may be manufactured separated and is insertable into the cavity of the housing 611. The reservoir 672 can likely hold 1, or more doses, for example, 2, 3, or 4 doses of a pre-selected medicament. The total dose of all batches of medication would not exceed the total FDA approved dose for a specified period of time, exemplified by an 8 hour period. The size and spread of the medicament dispenser 670 may not be limited by the drawings and may extend over any portion of the hard and soft palate.

In one embodiment, the medicament is radiation pellets for treatment of oral cancer or immuno-therapy. In another embodiment, the medicament is trans-mucosal or sublingual drugs, for example, but not limited to, nitroglycerine, intermezzo, albuterol, ADVAIR® medicine. In an embodiment where the medicament is intermezzo, the sensor is an EEF, EOG, or EMG sensor to detect insomnia and thereafter dispense the intermezzo. In another embodiment, the medicament is nitroglycerine and the sensor is an EKG monitor. Additional sensors are beneficial with this embodiment, including a blood pressure sensor, echocardiography and/or carotid doppler blood flow. In a third embodiment, the medicament is a dry powder micro-aerosol inhalation of insulin to treat diabetes and the sensor is a non-invasive continuous glucose sensor. In a fourth embodiment, the medicament is a bronchodilator and the sensor is a microphone to detect breathing difficulties such as wheezing, for example in asthmatics.

In one embodiment, the medicament is in pellet form and the pellet is filled with a liquid or aerosolized form under pressure therein. The pellet is rupturable, meltable, pierceable. or dissolvable A rupturable pellet ruptures upon application of pressure, such as being squeezed by a driver of a piezo electric motor. A meltable pellet open upon application of heat, such as heat from the power source via a heating electrode. The pellet may have a predesignated location 674 that is made of meltable material or dissolvable material which upon disintegration releases the said medication or be an on-off robotically operated valve that opens to release pre-determined concentration or dose of medication and then shuts off A pierceable pellet is opened by a micro-needle within housing 611. A dissolvable pellet is/could be simply ejected into the oral cavity and dissolves upon contact with saliva. Each pellet is a single dose unit of the selected medicament relative to the user.

As in the embodiment of FIGS. 1-3, up to four housings, a right and a left maxillary housing and a right and left mandibular housing, can be present and each could include a sensor and a medicament dispenser. As such, up to four or more medicament reservoirs 672 could be present and each can have a plurality of doses of a medicament. Different medications could be installed in different housing, each with an appropriate sensor for the medicament. If only one medication is installed in the user's device, then the medication and the sensor may be in the same housing or in different housings.

Figure 17:
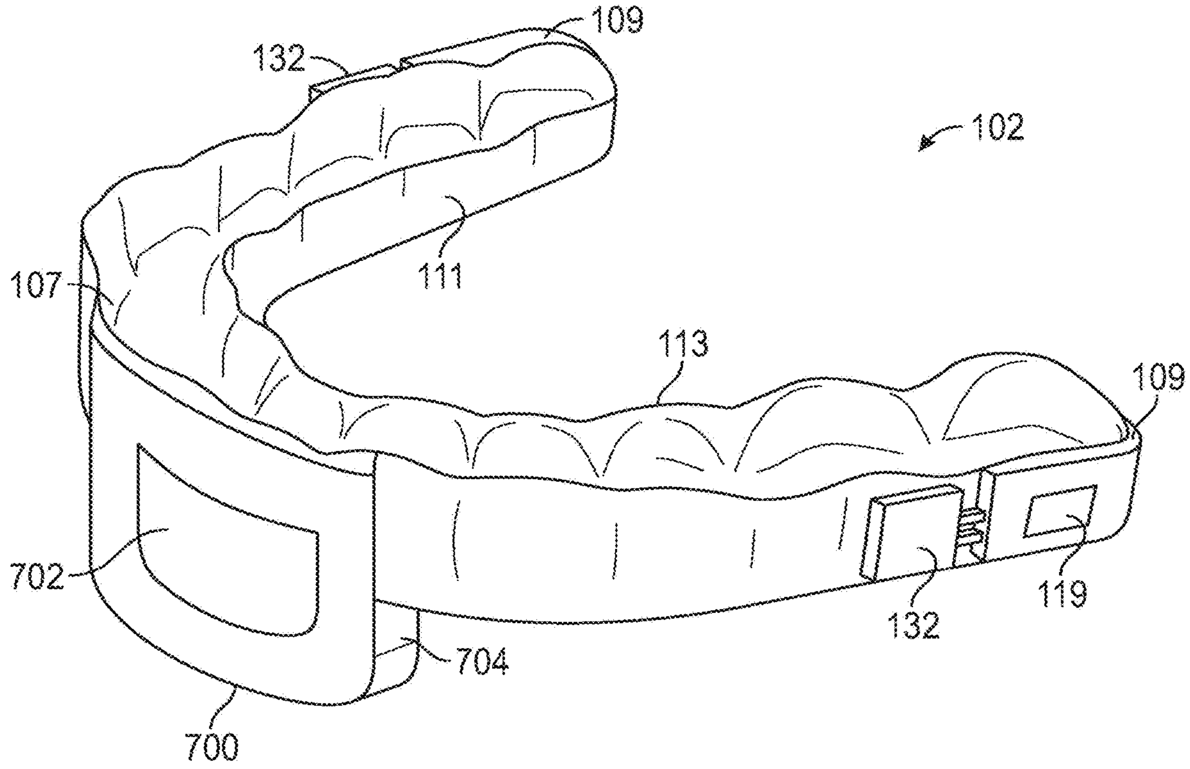
FIG. 17 is a left-side view of the maxillary device of FIG. 2 modified to include a digital camera or digital video recorder.

Turning now to FIG. 17, any of the maxillary devices disclosed herein may additionally include a forward facing photography/videography system 700, which includes a digital camera or video recorder 702 facing forward. The maxillary device here is the one from FIG. 2, modified to have an integrally molded recorder housing 704 which houses the digital camera or video recorder 702. The digital camera or video recorder 702 is electrically connected to the on-board circuit board within housing 109 or includes its own wireless transmitting system to send the data to the on-board circuit board within housing 109 or to an off-board microprocessor discussed below. Each of the features disclosed with respect to the maxillary devices of FIGS. 13-17 are equally applicable to any of the mandibular and maxillary devices of FIGS. 1-12.

Figure 5:
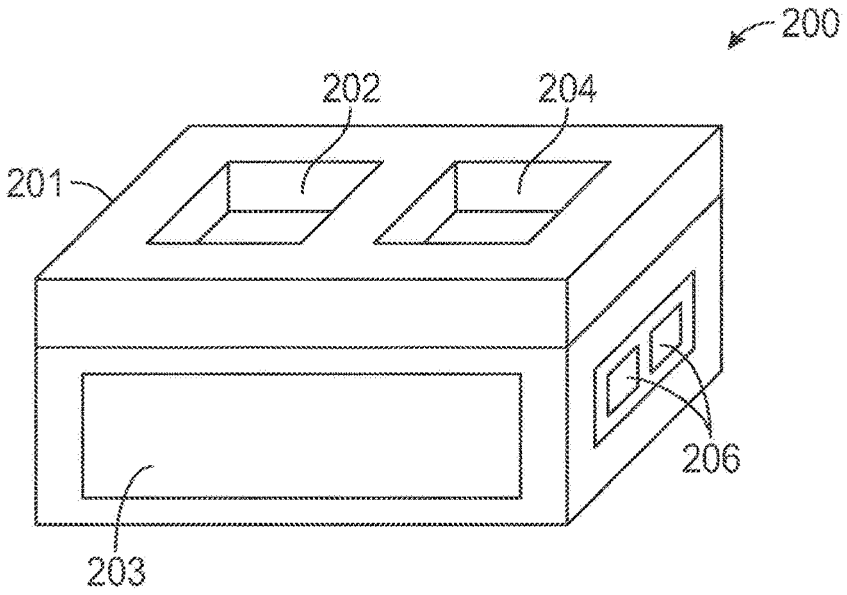
FIG. 5 is front, perspective view of a controller station for use with the devices disclosed herein.

Turning now to FIGS. 5 and 12, a controller station 200 is illustrated for operatively controlling any of the mandibular lingual repositioning devices 100, 101 described above, which together define a system 300 schematically illustrated in FIG. 12. The controller station 200 has a housing 201 defining a first charging unit 202 for receipt of the maxillary piece 102 and a second charging unit 204 for receipt of the mandibular piece 104. The first and second charging units 202, 204 may be receptacles defined in a surface of the housing 201. In another embodiment, the first and second charging units 202, 204 may be generally flat plates. The housing 201 has a display screen 203 for displaying information to a user and one or more ports 206 for connecting the charging station to power, other devices, and/or the internet. Alternately, instead of ports 206, the housing 201 can enclose wireless communication technology for other devices 310, for example, but not limited thereto, a printer, speakers, tablets, laptops, cellular phones, smart watches, and other cloud-based devices. The controller station 200 may include sensors to record ambient room conditions, such as light, temperature, humidity, noise/sound, etc. The controller station 200 optionally is battery powered and may include a rechargeable battery. The controller station 200 may be portable.

Alternately, rather than having the first and second charging units 202, 204 integrated into the controlling station 200, a separate charging station (not shown) having a first and second charging unit is possible. The charging station may be portable.

When the charging station is separate from the controller station 200, the controller station may be incorporated into a hand-held smart device and such a smart device would share blue tooth, WIFI, Video, audio and communication capability with sensors. In one embodiment, the controller can be a proprietary software program for use with or an App (software application) having full functionality to function like the controller station 200. System 300 and controller station 200 in all its embodiments will be HIPPA and HITECH compliant for purpose of medical privacy. Interface with the wide variety of electronic health formats (EHR) would allow system 300 and controller station 200 and its operated systems to be available for real-time data download and upload, active health care worker involvement in user's health care needs and would permit the health care worker to operate and alter any treatment and access and interpret diagnostic information provided by the system. As such controller station 200 and system 300 would allow newer formats of health care provisions such as tele-medicine and others yet to be defined. System 300 may be integrated into a full-function health care software-hardware system for patient assessments (such as telemedicine), tests, treatments and medications.

The controller station 200 encloses a circuit board having a microprocessor, including memory (non-transitory computer readable media) in which is stored firmware and learning algorithms, having a receiver of electronic communications, and having a transmitter of electronic communications, including wireless communication capabilities to electronically communicate with at least the MLRD 100, 101 for real-time communications with the sensors on board the MLRD. The MLRD 100, 101 has microprocessors on-board with a transmitter to transmit raw data from all sensors, stimulators and pressure pellets exemplified by the pulse oximetry sensor, the vibration and airflow sensor, lingual stimulator, lateral pterygoid stimulator, medial pterygoid or masseter stimulator, EKG sensor, sub-lingual nitroglycerine pellet discharge, etc. to the controller station 200 in real-time aided by system 300 for processing into executional commands exemplified by movements of the first driver and/or the second driver and activation of the stimulator for tandem or synchronized movements and activation thereof, i.e., simultaneous, independent, or sequential activation of the motors and the stimulator, training of muscles of speech or swallowing including the sequence of movement and strength and duration of current or release of a medication for sublingual or aerosolized use. The controller station 200 can simultaneously transmits the instructions to the MLRD 100, 101 microprocessors in each housing 108, 109, 108' which implement the instructions, exemplified by synchronizing the cranial to caudal adjustments, the anterior to posterior adjustments, and activation of the stimulator etc. The MLRD may also operate as a stand-alone mandibular protrusive and vertical advancement device or as a stand-alone lingual/pterygoid stimulator device or a timed-medication release device as preferred by treating health care provider.

The circuit board of the controller station 200, in one example, receives data from the MLRD that includes but is not limited to the pulse oximetry sensor and/or the vibration and air sensor and activates the motors and the stimulator as needed after a pre-selected number of breaths of the user. The firmware and algorithms, including learning algorithms as well as standard algorithms, stored in the memory of the circuit board may define the pre-selected number of breaths to be every breath, every other breath, every five breaths, or an absence of breath(s). Since the movements of the MLRD 100, 101 are done in real-time, the airway of the user can be opened without disturbing the sleep of the user or wake related fitness or any other activity of the user. Algorithms designed to record, interpret, and analyze, execute commands, and facilitate servo feedback functions will contain tolerance range, critical values, and reportable values. Similar application may be appropriate for sports, athletics, performance, and military users. The controller station may be miniaturized using PIC/QMC microprocessors in a hand-held device or wearable apparatus, such as a wristwatch, wrist band, helmet, waist belt, etc. or may be incorporated into an aircraft or space-ship's internal computing system.

The controller station 200 has a microprocessor configured to process the data and instruct the MLRD 100, 101. However, the controller station 200 can communication with a server, such as a cloud server, for further processing if desired, or for additional memory storage and/or communication of the data to authorized healthcare providers and/or sleep analysis experts, etc. and/or communicate with a database of said person. This intercommunication of databases can create therapeutic interventions and diagnostic testing of a user while at home, in place of work, outer space or anywhere in the world. This system 300 enables an authorized healthcare provider with capability to monitor and record patient data in real time, learn the patient, and alter the patient's treatment in real-time. The communications to and from the server can be through a wired or a wireless connection. The system 300 can also be configured to send data to a pharmacy, emergency medical services or HIPPA validated designated caregiver.

The server can also send commands, configuration data, software updates, and the like to the controller station 200. The configuration data may include, but is not limited to, configuration parameters for the system 300, configuration parameters for a particular user, and/or notifications, feedback, instructions, or alerts for the user.

The system 300, in addition to the MLRD 100, 101 can wirelessly communicate with additional sensors connected to the user to provide a broader data set for a more complete picture of the user's physiology. For example, electrocardiogram (EKG), electromyography (EMG), electrooculography (EOG), electroencephalography (EEG) sensors, echocardiography, blood pressure monitoring systems, and sensors sensing environmental conditions, such as temperature, ambient light, and humidity. The system may include a camera for video recording through the controller station 200 to evidence any nocturnal seizures, sleep-walking, other movement or violent disorders during sleep.

In operation, data from the sensors on the MLRD 100, 101, such as oxygen measurements and pulse data, is sent to the controller station 200 to be processed by the microprocessor to determine how much movement of the protrusive flange by activation of the second driver is needed, how much movement of the first driver is needed to separate the jaws of the user, and if and when to stimulate the transverse lingual muscle of the tongue to move the tongue forward. After some breaths, the controller station 200 may determine to stimulate the tongue and activate the second driver to move the mandibular piece, and hence the jaw of the user, forward (anterior) or backward (posterior) direction. In other instances, the controller station 200 may determine to stimulate the tongue and activate both the first driver and the second driver to separate the jaws and move the mandibular piece forward in order to adequately open the airway of the user.

The system 300 also creates three-dimensional images and videos of breathing, cardiac function, carotid blood flow data, eye-movements, jaw movements and brain EEG recordings for identification of medical conditions and interventions that may be useful to correct or treat those medical conditions.

A unique advantage of this system over any other existing systems is that the jaw and tongue can move synchronously, independently, or sequentially during sleep or during wake-related activities, in real-time and in anticipation of impending airway closure or changes in physiology, and in a provision of a measured response to those changes such as relief from, restriction of airflow as determined by the controller station 200 even before the airway has completely closed; thus, restoring unrestricted airflow even before the patient has completely stopped breathing (as in sleep apnea). This system can see airway obstruction before it happens and will keep the airway constantly open in any body position or depth of sleep. This is a distinct advantage over CPAP/BIPAP or any other mechanical or electrical system that is commercially available in the market. In addition, there are distinct advantages just by the breadth of functionality that has been described above.

The controller station 200 includes learning algorithms in the memory of the microprocessor that learns a user's sleep patterns and other physiological events and functions during sleep and wake, pathological events and activities during wake and sleep from the data collected over time and creates a "best response" for the simultaneous, independent, or sequential responses exemplified by tensing of the soft palate or Uvula, release of medication or stimulation of the stimulator and activation of the first and second drivers to open the airway or to train muscles of speech, and to synchronize these best responses such as exemplified by certain jaw movements that are associated with particular phases of respiration. The activation of the first and second drivers 130, 132 not only includes advancements, but also retractions of the first and second drivers 130, 132 to relax the jaws in between necessary advancements to open the airway to avoid potential TMJ problems. Any discussions herein directed to the mandibular component, with respect to the controller station 200 and the system 300, are equally applicable to the maxillary component. These are applicable to daytime (awake) related activities, including sports or athletic activities.

The controller station 200, in the memory of the microprocessor, may include a pre-programmed range for the movements of the first and second drivers 130, 132 based on sleep study data for the user conducted by an authorized healthcare provider. The pre-programmed range can be used by the controller station 200 in a stand-alone or auto servo mode. The pre-programmed range may be determined by simple or multiple linear regression models that employ data from inputs and from previous experiences, which the controller station 200 will be able to forecast ranges for the amount and direction of movements of the drivers 132, 134 and the amount or timing of energy discharge through the transverse stimulator(s). The controller station 200, in the memory of the microprocessor, may include data from tests previously performed on the user and/or the output of algorithms to set the MLRD 100, 101 each day for use just prior to sleep.

The controller station 200 can operate based on a stand-alone function or a servo function. In the standalone function, the controller station 200 operates the MLDR 100, 101 based on set parameters for the movement of the drivers, such as repetitive equal advancement and retraction of the mandible that are not based on active feedback. For example, a set 2 mm movement anteriorly of the mandible during each breath and a 2 mm posterior movement of the mandible after each breath, with a fixed amount of energy discharge to the electrode of the stimulator. The set parameters for the standalone function may be based on data collected from the specific user or may be based on a peer group of like sleep attributes. Standalone functions may also be created for these non-limiting examples, athletics, sports performance, military programs, weight loss programs, and fitness clubs.

In the servo function, the controller station 200 interactively controls the MLRD 100, 101 during sleep or wake, at home or elsewhere, based on the data collected from the sensors on-board the MLRD in a feedback loop and based on data available from the server. During operation, the continual feedback loop allows incrementally accurate interventions followed by listening to observational inputs exemplified by airflow measurements, video recordings, pulse-oximetry, doppler flow in carotids or advancement of mandible and followed by more interventions exemplified by protrusive or vertical adjustments based on real-time data even after a previous advancement or incremental increase in energy to stimulate the tongue. The changes to the advancement or application of energy to the stimulator will be capable of producing positive and negative changes regarding movement of the mandible and tongue. For example, the energy applied to the stimulator may be reduced relative to the prior application of energy discharge if the previous discharge of energy caused teeth grinding or cough. In another example, the protrusive movement of the jaw may be reversed if the previous protrusion advancement caused a deleterious change in any of the monitored physiological parameters. In another example training of muscles of swallowing would be altered upon observing retrograde movement of food or appearance of cough or gag.

Also, in the servo function, data from all sources, server, MLRD, and any other sensors attached to the user that are communicating with the controller station 200, are continuously processed through algorithms that are stored in the memory of the controller or stored in the server. Examples of other sensors includes, but is not limited to, wireless pulse-transit time sensors, and wireless EKG sensor. These two additional sensors would be utilized in addition to the MLRD to diagnose and treat sleep-induced hypertension and/or cardiac arrhythmia such as lack of oxygen to the heart, especially by collecting time synchronized data from the EKG sensor and the pulse oximeter sensor. For example, the server may include data related to sleep attributes and alcohol consumption to make adjustments for the user during sleep after drinking alcohol. For example, it may require a change in current applied to the stimulators 116 after alcohol consumption to effectively stimulate the lingual muscles. The same may be true of a user taking certain medications, especially those that depress brain function. As another example, the server may include data on myriad patients correlating sleep attributes to weight loss. As such, if the user loses 5 or 10 pounds, data from the server can be considered in the algorithm determining how much movement of the jaws is needed and/or whether to stimulate the tongue.

The system 300 may be used to treat many medical diseases, including but not limited to any type of sleep apnea, bruxism, sleep related GERD, sleep-induced hypertension, snoring, etc.

The system 300 may be used to diagnose any possible medical conditions related to sleep or while awake, including sleep apnea or other sleep disorders including sleep-induced hypertension, sleep-related cardiac arrhythmia, sleep related seizures, RLS and periodic limb movement disorders and other medical diseases, even those unrelated to sleep. Here, the MLRD 100 or 101 is placed in the user's mouth during a sleep period, such as at night, with the controller station 200 in a "test mode" in which the on-board sensors measure and monitor the user's physiological parameters mentioned above. The test mode is used for multiple sleep periods of over two to 30 days or longer, based on a time period set by a medical professional. For example, the user may have the controller station in "test mode" for seven days or longer. Then, the seven days of data is reviewed by the medical professional to determine whether the user has sleep apnea or any other sleep disorder, and if so, determines the parameters for the standalone mode, which are then stored in the controller station 200. The same system may be used even during the day and outside of the home of the user such as at place of work.

The system 300 may have a therapeutic mode, which implements the servo function. Here, the feedback loop is on for data from the on-board sensors, which is processed through an algorithm to determine the least amount of anterior and caudal movement to maintain an open airway and the least amount of energy discharge to stimulate the tongue and maintain an open airway and the order in which to take such actions, i.e., simultaneously, sequentially, or individually.

The device and system disclosed herein have numerous advantages, including artificial intelligence utilizing data collected by the MLRD during use to actively in real-time adjust the MLRD in response to the phases of respiration, degree of obstruction of the airway, snore sounds and vibrations and amount of hypoxemia present relative to each breath irrespective of the stage of sleep of the user, various levels of exertion, physical activity, and other applications. The system is capable of measuring a large number of cardiac, neurological and endocrine sensory inputs as described above exemplified by continuous non-invasive glucose, oxygen, blood pressure, pH monitoring, heart rhythm and temperature etc. The system is capable of photography for creating dental impressions, dentures or to diagnose gum disease etc. The system is capable of executing a large spectrum of functions such as mandible protrusion, administering sub-lingual insomnia medication like Intermezzio or cardiac medication like nitroglycerine or training muscle groups for swallowing or speech. The system is capable of communicating with user, provider, EHR (Electronic Health Record) and pharmacy etc. This system is capable of determining restriction to airflow, increase in velocity of air and turbulence, decreasing levels of oxygen and increasing levels of heart rate, pH monitoring and any other physiological parameter that could be installed in the future with constant inputs of physiological parameters (unlike with CPAP machine or oral appliances that are available in the industry), such as those mentioned above. This 24 hour a day seven days a week capability of collection and processing of data allows the system to actually make adjustments exemplified by the movement of the mandible and tongue prior to closure of the airway and hence will work as a preventative form of treatment for sleep apnea.

Age and gender specific physiology of the airway and the mouth during sleep are known to affect sleep and cause sleep disorders. The system 300 and 310 will collect data that will enable the development of algorithms that are age and gender specific, which can improve treatment outcomes for future users. System 300 and 310 has ability to create database of all physiological and pathological events measured in real-time and time synchronized with each other in its users and develop algorithms for normal and abnormal manifestations of disease states during wake and sleep and develop new cause-and-effect understanding of these events that have never been observed before. Recording and correlation of these phenomenon with sensors, especially during sleep would help understand conditions such as 'wake-up strokes' (occur during sleep) that account for 14% of all strokes and diagnose conditions like obstructive sleep apnea that occurs with almost 83% of cardiovascular disease, 58% of heart failure and 53% of atrial fibrillation, to name a few.

The system not only advances movement of the mandible (cranially and anteriorly), but enables a relaxed movement of the mandible (caudally and posteriorly), which allows the temporomandibular joint to relax periodically to prevent jaw discomfort, temporomandibular joint strain and destabilization, morning stiffness of said joint, and alteration of the user's bite.

The system 300 can also be used for users that snore, but who do not yet have sleep apnea. The inclusion of the vibration and airflow sensor enables the measurement of the intensity of snoring and can open the airway before the sub-sonic snore has become audible. The inclusion of stimulators of soft palate and uvula can reduce or eliminate snoring in users that do not have sleep apnea yet. Also, the system 300 can be used along with a CPAP machine and enable the CPAP machine to be used at a lower air pressure than a typical setting for user's that cannot tolerate CPAP machine at their typical air pressure.

In one example, the devices disclosed herein are worn by a user at nighttime and includes sensors to monitor nocturnal silent angina or myocardial ischemia (measured by continuous EKG monitoring) that could cause sudden death or acute myocardial infarction during sleep or wake (especially silent ischemia). With the medical dispenser present, an incident could be treated with release of sublingual nitroglycerine from medicament reservoir while data such as continuous blood pressure recording, EKG, echocardiography and carotid doppler blood flow is continuously recorded and transmitted to the controller station 200 or cloud server 300. The cloud server 300 can then send the data to a monitoring on-call physician, a handheld device or computer to alert the patient, as well to the nearest ER/ED (emergency room) for early ambulance dispatch.

In other examples, the sensors selected for use in the maxillary and mandibular devices disclosed herein can be those that can diagnose cardiovascular, gastrointestinal, and/or neurological medical conditions. The devices can have sensors and treatment methods to treat the same medical conditions.

In an athletic environment, the sensors selected for use in the maxillary and mandibular devices disclosed herein can be the pulse-oximetry, CDT/CNT based infra-red oxygenation receptors, heart rate and EKG, PTT with non-invasive blood pressure recording, carotid blood flow, CMUT/IVUS doppler ultrasound, blood glucose level (in tongue or soft palate) for diabetic or hyperglycemic individual, airway resistance and total tidal volume (airflow measurement per breath), EEG recording, respiratory rate measurement, core body temperature, temperature and humidity derived from respiratory (inspiratory and expiratory) airflow, computational mini-Incentive Spirometry based on above inspiratory-expiratory airflow or time ratio (early detection of exercise-induced asthma in an athlete, a soldier or a fitness or weight loss buff), and combinations thereof. Data from these sensors will allow determination of performance restrictions and methods to physiologically improve performance such as legal nutritional supplementation or medications, such as aerosolized asthma medication or aerosolized insulin for a diabetic athlete, soldier or a fitness or weight loss buff, for underlying medical conditions or increasing the size of airway to help improve oxygenation and reduce heart rate, reduce elevations of body temperature or loss of humidity during exercise or athletic performance.

Also, evaluation and prevention of concussion injuries is possible with maxillary and mandibular devices. There is a significant need here because statistic show that 1.6 to 3.8 million sports related concussions occur per year in the US, and the National Institute of Health reports that chronic post-traumatic headache occurs in 47 to 95 percent of all traumatic brain injuries. Football in particular has staggering stats.

TABLE 3

Chronic traumatic encephalopathy (CTE) in deceased football players

| Football Players | Percentage with CTE |
|---|---|
| National football league | 99% |
| CFL | 88% |
| Semi-professional | 64% |
| Collegiate | 91% |
| High School | 21% |

Figure 56:
FIG. 56 is a left side computer generated image of an embodiment of the mandibular repositioning device in an open position in the mouth of a skull.

The first ten minutes after a concussion are extremely important in preventing brain injuries. A concussed athlete loses consciousness, muscles relax, and thereafter, the tongue and jaw fall back and obstruct the airway. As shown in FIG. 56, the anterior to posterior advancement and cranial to caudal advancement of the mandibular repositioning device 800 (also referred to as an anterior vertical mandibular lingual repositioning device (AVMLRD)) disclosed herein holds the jaw and hence the tongue forward and down relative to the maxillary piece, which improves opens the airway (increases the size of the airway) for improved airflow, breathing and oxygenation of the brain and heart (along with other organs). For a concussed athlete wearing an AVMLRD, another person needs to place two hands behind the jaw and using two thumbs gently move the chin down, thereby the AVMLRD automatically draws the jaw and tongue forward creating a bigger airway and clearing an obstruction thereto. This can save an athlete's life and reduce brain injury resulting from loss of oxygen. This positive effect will be further incrementally improved upon with electrical stimulation of the tongue (when a lingual stimulator is installed in the AVMLRD) to aid in moving the tongue forward. The AVMLRD can reduce the recovery period, reduce long-term damaging consequences of concussions, and prevent traumatic brain injury (TBI) and chronic traumatic encephalopathy (CTE). Sensors useful for application to concussions that can be included in the AVMLRD include EEG sensors, carotid doppler blood flow ultrasound sensor, airway SMCA and airflow sensors.

In one aspect, methods of lowering heart rate during physical activity are disclosed. The method starts by identifying a person having a smaller than normal SMCA (discussed in the background section) in need of being increased while awake. Most people are not aware of the size of their smallest concentric airway cross-sectional area, and many people have a SMCA that is ⅓ of the normal size average of 149 $mm^2$. These people often think that their athletic performance or ability to lose weight is limited by their talent or effort, but it may actually have a direct correlation to the size of their SMCA. Breathing is simply less efficient for these people and the increased effort to breath causes early fatigue of the diaphragm and the abdominal-thoracic muscle of respiration and drives the heart rate up to the cardiovascular workout rate rather than remaining at the fat burning rate. Increase in exercise causes an increase in body temperature, heart rate, and respiratory rate. Hear rate increases by 10 beats per minute for every 1 °C increase in body temperature. Women are inherently more prone to early fatigue because of a natural tendency to have smaller SMCA, thereby demonstrating greater hypoxemia than the same size man with similar height and build. This device and method, therefore, has the potential to help women improve their fitness, weight, and thus impact their overall health in a positive manner.

Next, the identified person is provided with a mandibular repositioning device fitted for their respective mandible and maxilla that has a maxillary piece comprising a tooth covering having a driver flange protruding laterally outward on a right side proximate a backmost teeth mold and/or on a left side proximate a backmost teeth mold, each driver flange having an anterior side with a convex curvature and a mandibular piece comprising a tooth covering having a protrusive flange extending cranially therefrom positioned to have a posterior side engaged with the anterior side of each driver flange, the posterior side of each protrusive flange has a concave-to-convex curvature from its base toward its most cranial point and a convex portion of the concave-to convex curvature engages the convex curvature of the driver flange in a rest position. In such a mandibular repositioning device downward movement of the mandibular piece moves the convex portion of the posterior side of the protrusive flange along the convex curvature of the driver flange, thereby moving a user's mandible forward. During physical activity, simply by opening the mouth, the mandibular repositioning device advances the mandible caudally and anteriorly, whereby it increases the size of the person's smallest concentric airway cross-sectional area making breathing easier (decrease the resistance to airflow during beathing), increasing airflow, decrease (or preventing an undesired increase) said person's heart rate for a given level of exercise, decrease in $CO_2$ level, increase oxygen saturation, decrease in relative respiratory rate for a given level of exercise, reduction in generation of excessive body heat at a given exercise level, and decrease loss of water from a reduction in sweating and through respiration (respiratory rate), decrease loss of electrolytes, decrease in muscle cramps, increased endurance, increased speed, increased stamina, increased strength during exercise, increase in physical performance.

The mandibular repositioning devices disclosed herein by increasing the smallest concentric airway cross-sectional area of a user's airway, which is behind the tongue, works for both mouth breathing and nose breathing. The improvements in breathing (respiratory rate) from decreases airflow resistance achieved by the anterior-posterior repositioning and cranial to caudal repositioning yield the additional benefit of maintaining body water content (decreasing the amount of dehydration relative to the given exercise) and lowering the rate of rise in body temperature, both of which improve endurance.

In one embodiment, the physical activity is athletic or military training in which data from sensors included in the mandibular repositioning device are monitored by a coach or superior to determine or monitor how anterior-posterior and cranial-caudal repositioning adjustments effect the user and various parameters such as heart rate, body temperature, respiratory rate, oxygen saturation level, etc. In particular, the height of the open mouth in the cranial-caudal direction can be "dialed in" to maximize endurance or another aspect of the user's performance. This may be determined by monitoring the user's physical activity while making incremental changes in the anterior-posterior and cranial-caudal repositioning adjustments. In another embodiment some sensors are in the oral appliance while others may be on the athlete/trainee's skin, inside a wristwatch-type wearable biometric sensing device or other bodily biometric sensors that are all feeding data into the controller station or handheld smart device that is being monitored by the coach or supervisor.

Figure 53:
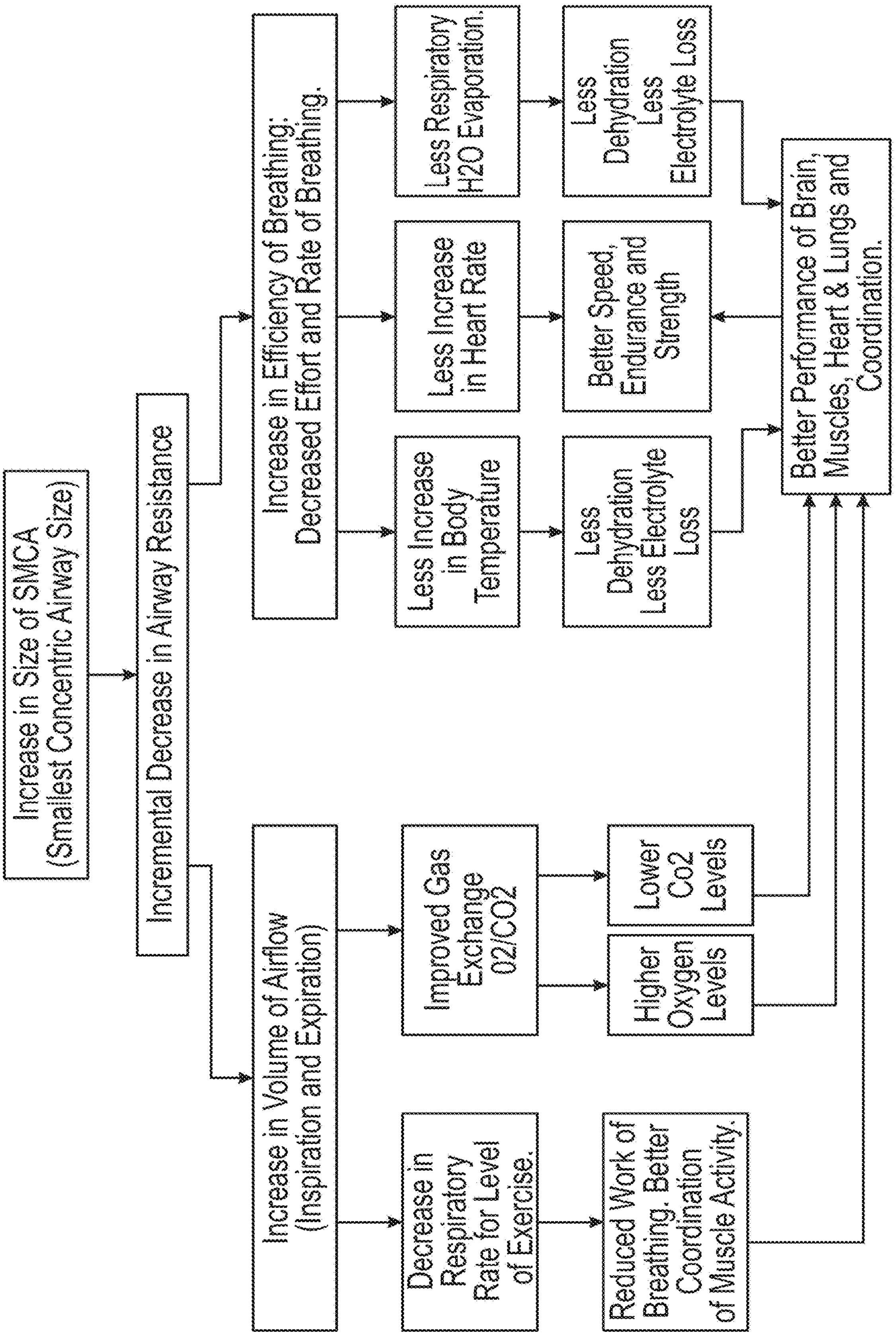
FIG. 53 is a flowchart of the physiological effects of increasing the size of the SMCA of a user with the mandibular repositioning devices herein.

The above is equally applicable to weight loss activities. Determining the user's anterior-posterior and cranial-caudal repositioning adjustments for fat burning activity is of great importance. Most individuals that try to exercise for the purpose of losing weight give up because of unsatisfactory results over a short period of time. Due to the body's deconditioned state, heart rate rises rapidly into the cardio range with light exercise. This prevents the individual from losing weight although they do get cardio exercise. Moreover, carrying excess weight causes increased oxygen consumption. The individual is unable to increase oxygen delivery due to a limited capacity to breathe. This is a limitation of the narrowest cross-sectional area in their airway (SMCA) posterior to the tongue. Under normal circumstances, an individual simply has no choice but to breath harder to bring in more oxygen. This increases work of breathing, increased body fluid loss, sweating, increased body heat, increased heart rate and quicker fatigue. Thus, resulting in termination of the workout and eventually majority of individuals give up the training. AVMLRD can increase the narrowest cross-sectional area (SMCA) that is the limiting factor. With reference to FIG. 53, incremental reduction in airflow resistance and increase in airflow and oxygenation with lesser work of breathing will delay dehydration, sweating, body heat rise, fatigue and keep the heart rate at a lower level (within the fat burning range) while offering higher amount of calorie consumption for a longer period of time, thus increasing the possibility of successful weight loss. It is also expected that users will experience an improvement in personal self-image, emotional markers and mental health, and possibly an increase in endorphins and decrease in adrenaline production during exercise and better control of diabetes and blood sugar problems.

A predictive table of expected improvement in breathing efficiency as the SMCA increase is presented below.

TABLE 4

| Airway Radius (mm) | Airway Diameter (mm) | Airflow Resistance | Airflow Increase (%) | SMCA ($mm^2$) | Breathing Efficiency (%) |
|---|---|---|---|---|---|
| 3.86 | 7.71 | 0.659 | 0 | 46.6 | 2 |
| 4.18 | 8.36 | 0.476 | 38.4 | 54.8 | 2 |
| 4.39 | 8.77 | 0.394 | 67.5 | 60.2 | 3 |
| 4.58 | 9.16 | 0.331 | 99.3 | 65.7 | 3 |
| 4.77 | 9.54 | 0.282 | 133.9 | 71.2 | 4 |
| 4.95 | 9.90 | 0.243 | 171.3 | 76.7 | 4 |
| 5.12 | 10.24 | 0.212 | 211.4 | 82.1 | 5 |
| 5.61 | 11.22 | 0.147 | 348.4 | 98.6 | 7 |
| 6.06 | 12.12 | 0.110 | 510.4 | 115.0 | 9 |
| 6.61 | 13.22 | 0.076 | 765.0 | 136.9 | 13 |
| 7.00 | 13.99 | 0.061 | 985.1 | 153.3 | 16 |

Figure 43:
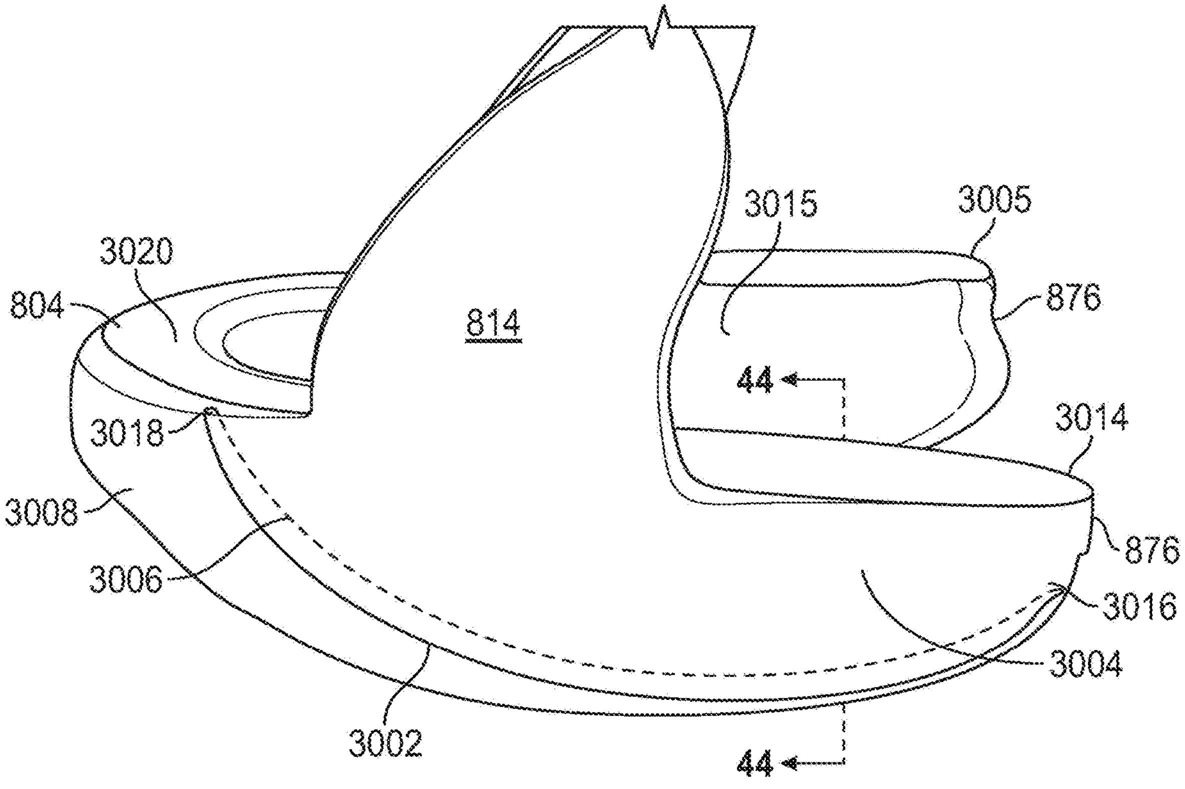
FIG. 43 is a photograph of a mandibular piece having a buccal saliva drain.
Figure 44:
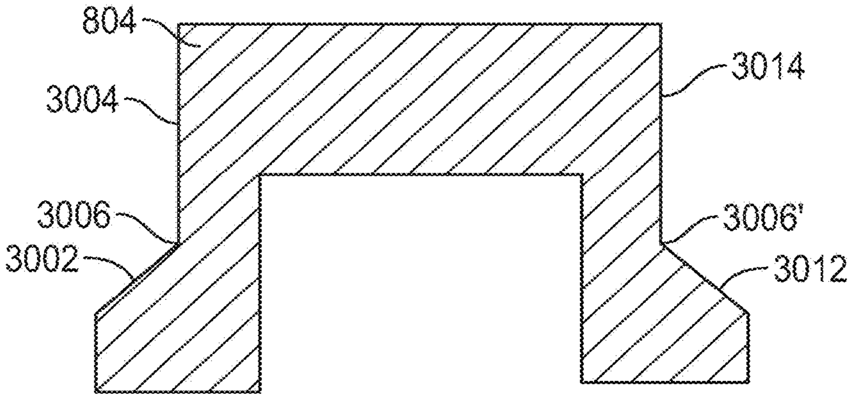
FIG. 44 is a cross-sectional representation of the mandibular piece of FIG. 42 along line 43-43.

Turning now to FIGS. 43 and 44, in all aspects, the presence of a mandibular repositioning device in a user's oral cavity, as with all mouthpieces, triggers the production of saliva. All of the mandibular repositioning devices disclosed herein can include saliva drain features in one or both of the mandibular piece and the maxillary piece. The mandibular piece 804 comprises a first buccal saliva drain 3002 in a right buccal surface 3004 and a second buccal saliva drain (not shown) in a left buccal surface 3005, each comprising an elongate arcuate ridge 3006 extending from proximate an incisor region 3008 to a posterior terminus surface 876 and a first lingual saliva drain 3012 in a right lingual surface 3014 and a second lingual saliva drain (not shown) in a left lingual surface 3015, each comprising an elongate arcuate ridge extending from proximate the incisor region 3006 to the posterior terminus surface 876. Each elongate arcuate ridge 3006, 3006' is sloped caudally away from the tooth covering. Each elongate arcuate ridge 3006, 3006' begins at a first end 3016 more caudally proximate the posterior terminus surface 876 than an opposing end 3018 proximate the incisor region 3008. The opposing end 3018 terminates most proximate an upper surface 3020 of the tooth covering. This saliva drain feature rapidly removes excess saliva from the lingual side and the buccal side posteriorly for swallowing and anteriorly for transport to the superior surface of the tongue to be then transported back across the palate and swallowed. Some saliva will move up the incisors for deposition on the tongue anteriorly.

Figure 45:
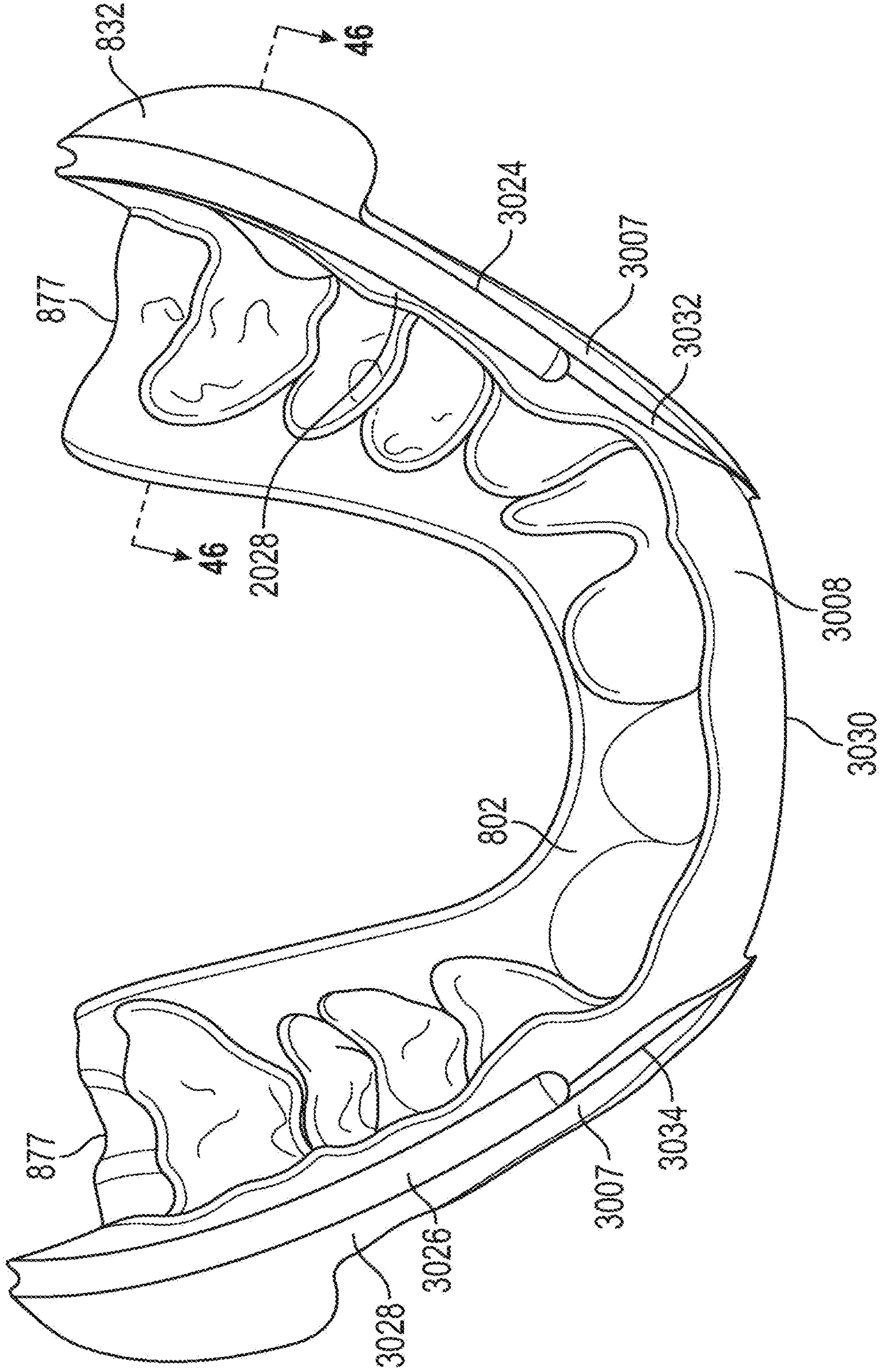
FIG. 45 is a photograph of a maxillary piece having an anterior saliva trough.
Figure 46:
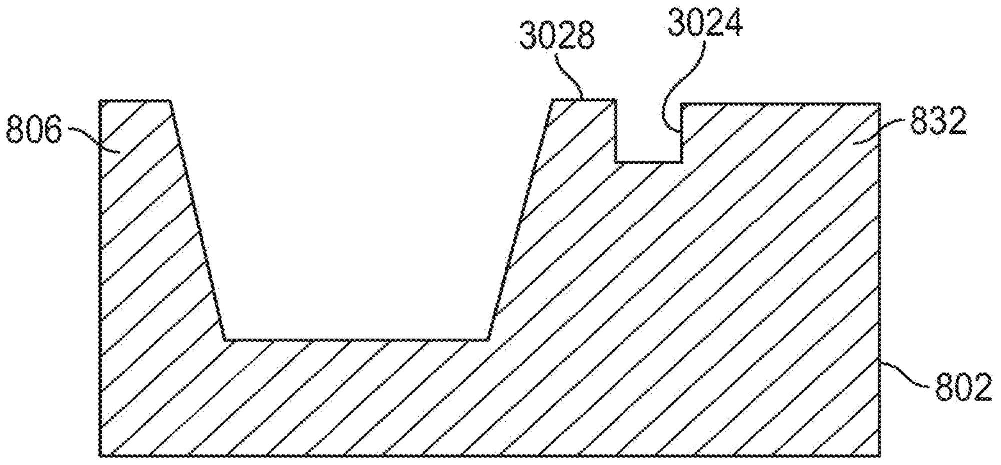
FIG. 46 is a cross-sectional representation of the maxillary piece of FIG. 42 along line 45-45.

Turning now to FIGS. 45 and 46, the maxillary piece 802 comprises a first cranial saliva drain 2024 and a second cranial saliva drain 2026, each being an elongate trough in a cranial surface 2028 thereof on the buccal side thereof and extending from proximate the incisor region 2007 to the posterior terminus surface 877 thereof. The first and second cranial salvia drains 2024, 2026 are sloped to drain saliva posteriorly. Each of the first and second cranial salvia drains 2024, 2026 also open anteriorly into a sloped gutter 2032, 2034 leading to the buccal surface most proximate the incisor region. The sloped gutter 2032, 2034 slope anteriorly and caudally, which forms a gentle excavation on the anterior surface of the maxillary piece that moves saliva like a sloped dam. This moves a large amount of saliva due to the large surface area anterior to the incisors while keeping the thickness of the layer of saliva at a minimum. This prevents flooding of the space between the lips and teeth. The saliva will naturally flow along the caudal surface of the maxillary piece back to the tip of the upper surface of the tongue for transportation along the upper surface along the palate to the back to be swallowed. Also, the maxillary piece can have a front saliva flow channel 3030 extending across and between left and right incisor regions.

Figure 47:
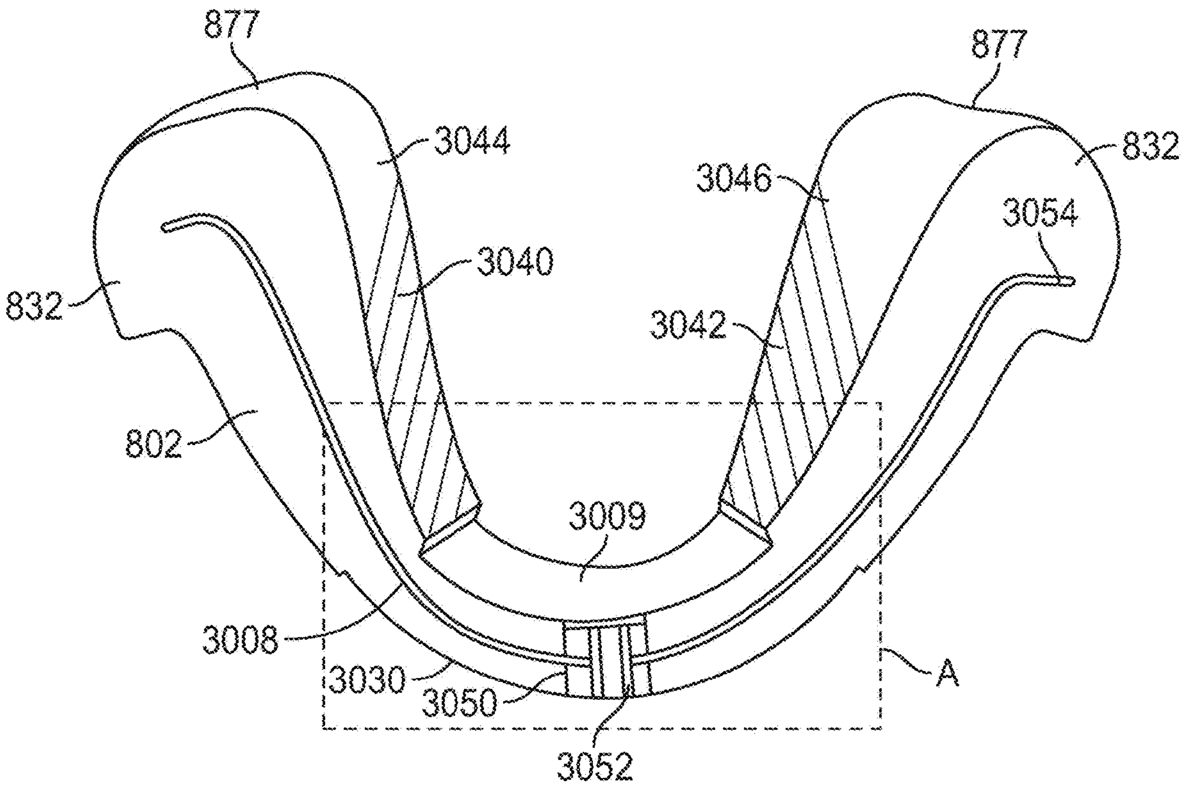
FIG. 47 is a photograph of a maxillary piece having additional saliva drain features and a flow tube.
Figure 48:
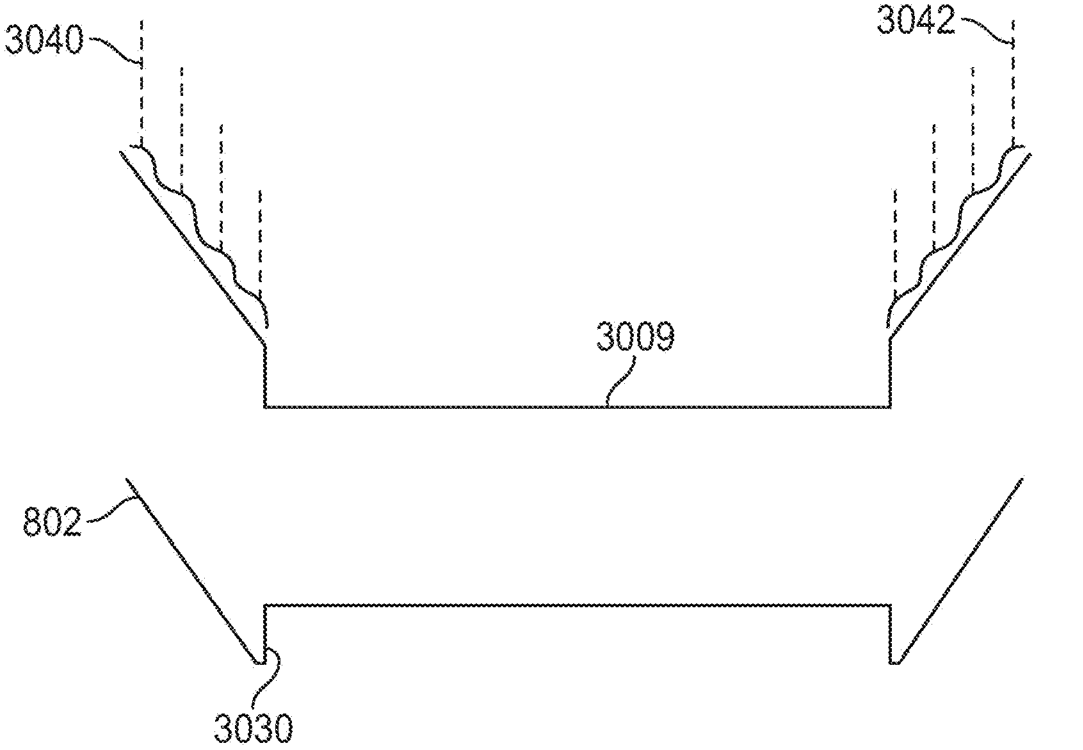
FIG. 48 is an enlarged, rear view of the details of FIG. 46 within dashed box (A).

Turning now to FIGS. 47 and 48, the maxillary piece 802 comprises undulated sloping saliva drain channels 3040, 3042 on each of the lingual palatal surfaces 3044, 3046 beginning proximate the lingual incisor region 3009 and extending posteriorly to the respective posterior terminus surface 877. The undulating sloping saliva drain channels 3040, 3042 are angled to direct saliva posteriorly to the soft palate, i.e., slope from an anterior inferior position to a posterior superior position. This moves saliva along, up and back, rapidly to facilitate swallowing. FIG. 48 is an enlarged, rear view of the section of the maxillary piece 802 from FIG. 47 shown in the dashed box (A).

The mandibular piece and maxillary piece with the saliva drain features facilitate rapid emptying of excess saliva from the mouth, around the teeth and cheeks back into the oropharynx in a well distributed pattern. This will ensure that no single spot in the mouth will be flooded. The saliva drain features provide numerous benefits or improvements to athletic performance. First, it reduces salivary interference with breathing, swallowing, and speaking while engaged in individual or team sport performance or training. It swiftly removes saliva and ingested liquids from the oral cavity into the gastro-intestinal tract, thus enhancing the athlete's ability to breath without interference. It improves hydration levels of the athlete by preventing the need or desire to constantly spit excess saliva or ingested fluids.

Figure 49:
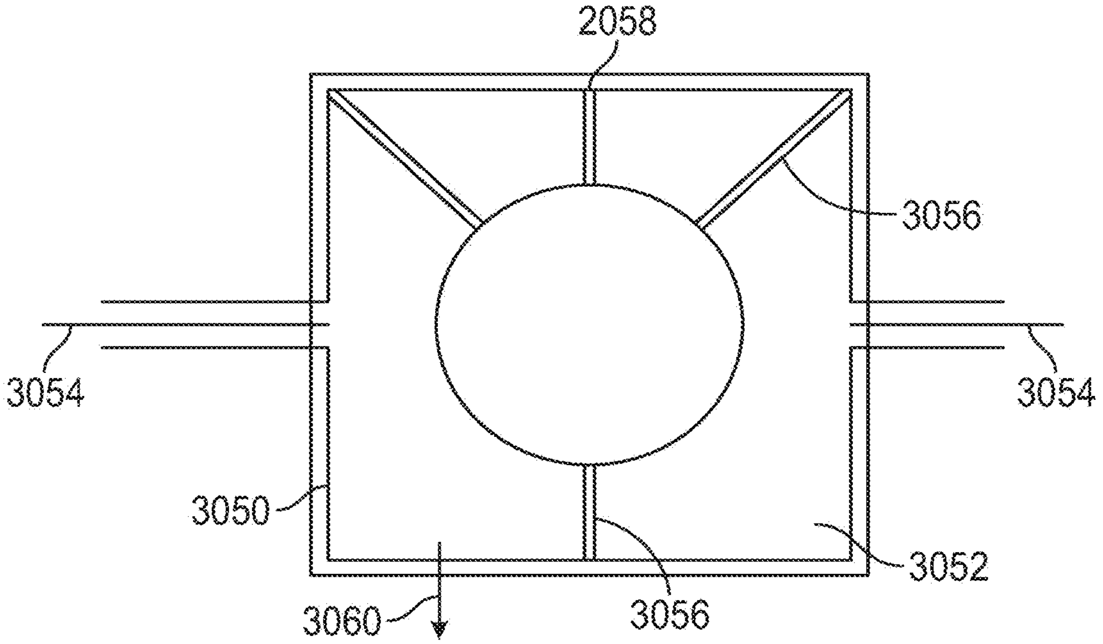
FIG. 49 is a transverse cross-sectional view of the flow tube.

If the mandibular repositioning device is used as a sleep device for obstructive sleep apnea, the saliva drain system will prevent drooling or pooling of saliva and choking during sleep. It will also reduce difficulty falling asleep associated with excess salivation, a phenomenon commonly observed among people who use an oral appliance for sleep apnea or for bruxism. Thus, it will reduce one of the most common causes of rejection of oral appliance as a treatment of OSA or bruxism. Also, it will deepen sleep because it will eliminate the constant need to swallow or cough with excess salivation that pools in the oral cavity of users of oral appliances. Referring to FIGS. 47 and 49, the maxillary piece 802 can include a detachable (i.e., removably, replaceable) or integral flow tube 3050 at the incisor region having a flow direction from anterior to posterior and vice versa. The flow tube 3050 may have a snap-fit feature snapping to or into the incisor regions of the maxillary piece. As more clearly seen in FIG. 49, the flow tube 3050 is shaped and sized to reduce drag on airflow and simultaneously receive a drinking straw for fluid intake. The flow tube 3050 can include a sensor 3052 electrically connected to one or both of the electronics housed within the maxillary piece 802. The electrical connection may be provided by a low voltage wire(s) 3054. The sensor 3052 can be an airflow pressure and volume sensor. A nanotech airflow pressure and volume sensor may be needed because of size constraints. The sensor may also measure velocity of the airflow, temperature, and humidity of the airflow. The data from this sensor can be used to calculate tidal volumes, minute ventilation, airflow resistance, which can be used by the microprocessor in the driver flange 832 or in a controller station, as described herein, to directly impact decision making related to adjustments of the mandibular repositioning device relative to the cross-section of the smallest concentric airway cross-sectional area. The sensor can be shaped to define supports 2056 that positions a conduit 3058 or defines a conduit 3058 that receives a drinking straw.

Still referring to FIG. 49, the flow tube 3050 houses a speech module 3060 configured to adjust the volume and amplitude of speech and/or clarify the speech, which can be useful for a sports team or the military or medical speech training purposes. The sensor 3052 and speech module 3060 can communication wirelessly with a recording system worn by the user, for example in a helmet or on the body, or with a mobile electronic device, including an app on the mobile electronic device, or with a recording system in the electronics of the maxillary piece (by a wired connection or a wireless connection) and/or with a controller station disclosed herein. The flow tube 3050 may also include a camera or video recording device such as daylight or infrared night vision system or thermal capture system to provide feed to recording systems with sprots, military or medical purpose.

Figure 50:
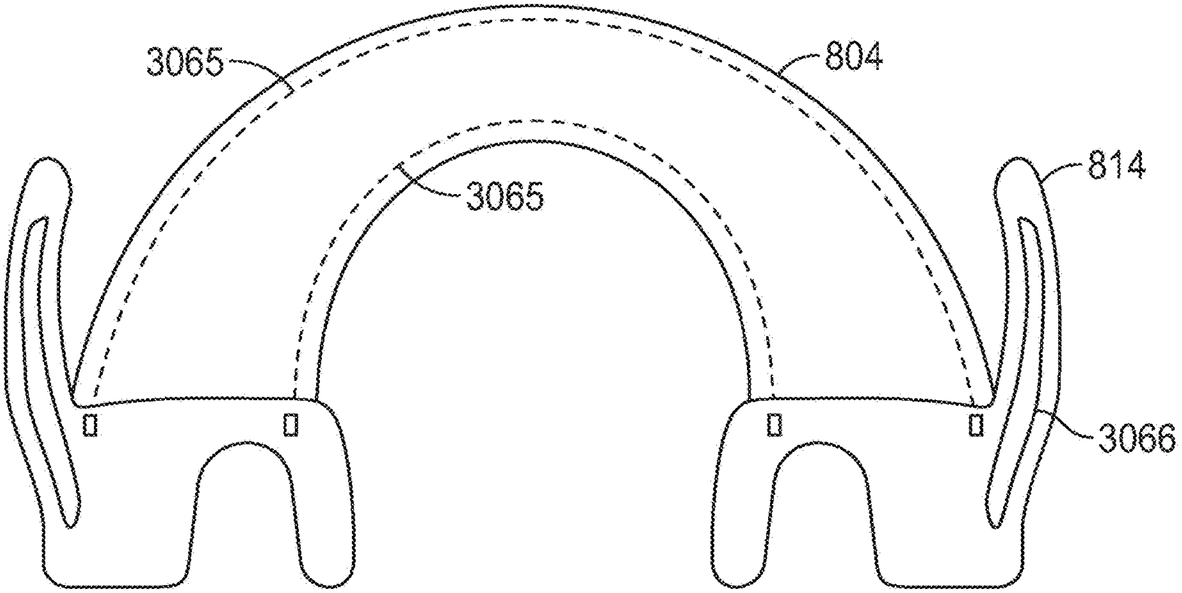
FIG. 50 is a rear perspective view of a mandibular piece having strength reinforcement features.

Referring to FIG. 50, the mandibular piece 804 is shown to exemplify adding a strength feature 3065 thereto. The strength feature 3065 in this example is present in the tooth covering and includes a metal cable or rod on the medial and lateral sides of the tooth covering. The metal cable or rod can be titanium or stainless steel and may be braided cables or rods, or any equivalent material relative thereto. The carbon or rods may be 0.1 to 0.3 mm in vertical thickness and 0.1 to 0.2 mm in horizontal thickness. The strength features 3065 can be encapsulated by the polymer during the molding process, or two channels can be formed in the polymer and the strength feature can be pushed or pulled therethrough. The purpose of strength feature is to allow levels of flexibility in maxillary or mandibular appliance materials while providing torsional strength required to maintain effective structural integrity of the device, provide quality of absorbing kinetic or torsional forces and protect device and the user of the device from potentially harmful/damaging excessive internal or external forces. Any channel openings formed in the polymer can be sealed by UV curing of polymer. The same strength features can be incorporated into the maxillary piece using the same procedures.

Still referring to FIG. 50, a stainless steel or titanium plate, strength feature 3066, can be installed in the protrusive flange 814. A hollow cavity matching the shape of this metal plate is formed inside the protrusive flange and a receiving recess is formed in the mandibular piece with the opening thereof in the infero-lateral surface below the protrusive flange. The first end of the plate is inserted into the protrusive flange and the second end is seated in the recess in the mandibular piece. Thereafter, the protrusive flange is sealed to the mandibular piece with UV curing of the polymer.

Figure 51:
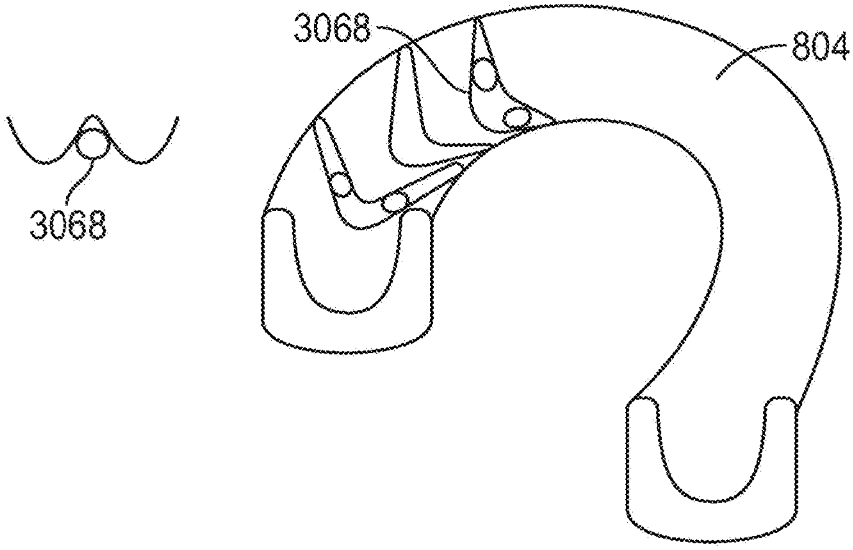
FIG. 51 is an example embodiment of a retention feature for mandibular repositioning devices for use during physical activity.
Figure 52:
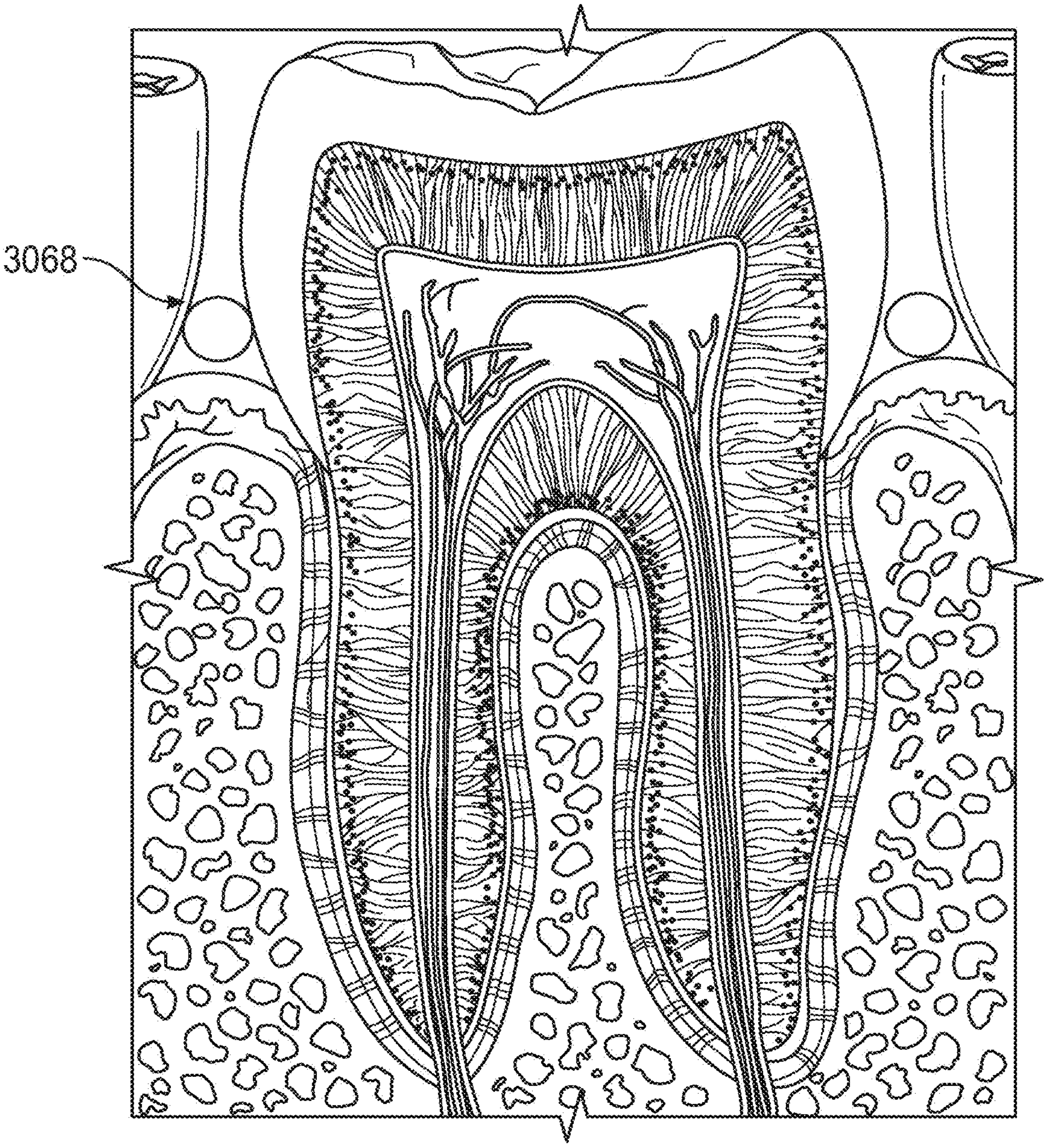
FIG. 52 is an illustration of the positioning of the retention feature of FIG. 50 relative to adjacent teeth.

Referring now to FIGS. 51 and 52, a retention feature 3068 is included in the mandibular piece or the maxillary piece to help maintain the same in a secure position while in the user's oral cavity. In this example, the retention feature 3068 is a clasp formed by forming or molding a small bump inside the tooth covering at a position that is at an intersection of immediately adjacent molar and/or premolar teeth. In one embodiment, a first clasp is positioned to be between the second and third molars and may be on the lingual side or the buccal side, with the lingual side being preferred, and a second clasp is positioned between the first molar and the premolar. The position of the clasps should be same on the left and the right of the tooth covering. The clasp typically has a diameter in a range of 0.2 mm to 1 mm, which will be determined on the basis of the interdental gingival sulcus close to the gingiva of the user.

Additionally, for physical activity uses, the mandibular repositioning devices, each of the mandibular piece and the maxillary piece in particular, can include a shock absorbing feature, such as sealed air pockets to cushion the teeth from impact and prevent wear and tear on the TMJ, or one or more polymer layers inside an outer acrylic hard shell, or a soft outer polymer on the frictional surface of the mandibular and maxillary pieces. In one embodiment, one or both of the mandibular piece and the maxillary piece have an outer hard acrylic shell and inner soft polymer with a 0-0.02 to 0.5 mm continuous layer of air with supports at the cusp of the teeth and horizontal band of supports across the mid-dental plane of the maxillary and mandibular teeth.

Figure 54:
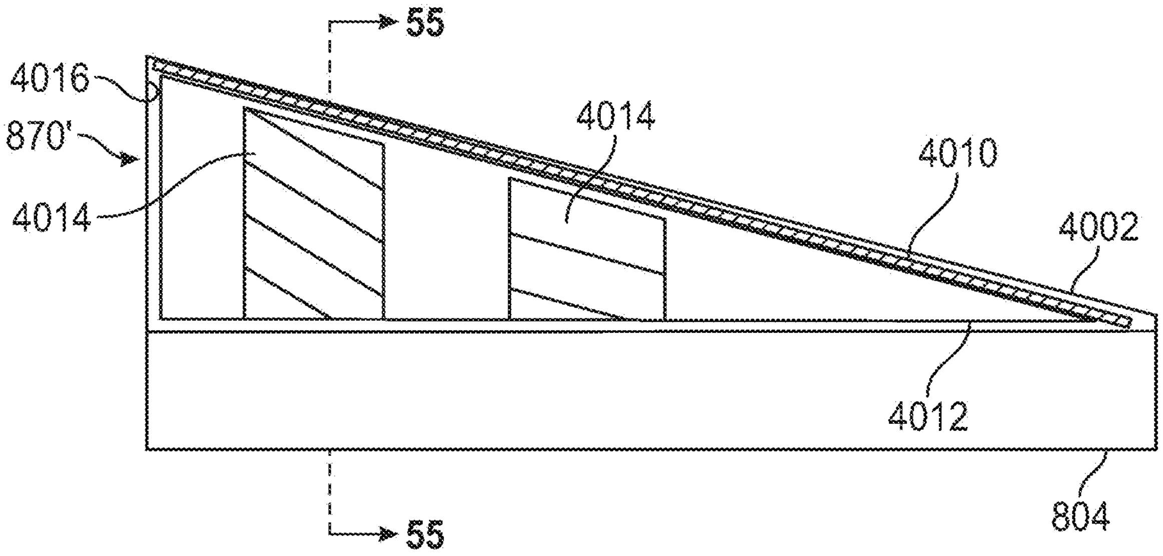
FIG. 54 is a longitudinal cross-section through a wedge-shaped plateau to reveal a shock absorbing feature.
Figure 55:
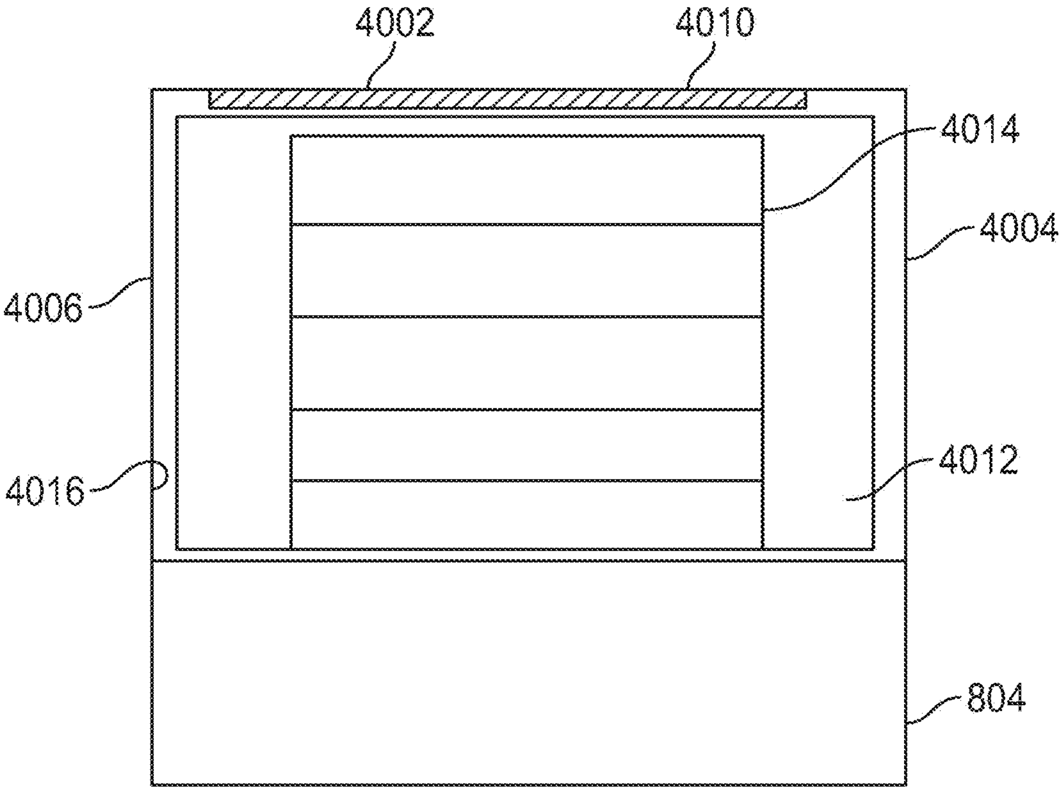
FIG. 55 is a transverse cross-sectional view along line 55-55 in FIG. 54.

Turning now to FIGS. 54 and 55, one embodiment for a shock absorbing feature is presented in the wedge-shaped plateau 870' of the mandibular piece 804. The wedge-shaped plateau 870' has an outer firm layer 4002, which may comprise a polymer, for the upper, outermost surface of the plateau 870' with a rigid plate 4010 thereunder, such as a titanium plate, and has a flexible material forming the buccal side 4004 and the opposing side 4006 thereto, which both compress and expand as needed by the user to absorb shock. The plate 4010 sits on an air cushion 4012 and one or more springs 4014. The plate 4010 holds the spring(s) 4014 in partial compression and forms an airtight (hermetically sealed) chamber 4016 in which the air cushion 4012 and spring(s) 4014 are housed. The wedge-shaped plateau as described above can have various sizes depending upon the user and the number of protrusive flanges in a kit. The spring(s) 4014 can have a preselected spring rate and/or degree of partial compression for a selected level of shock absorbance desired for a particular user.

The spring(s) 4014 may be coil springs or elastomeric springs. Non-limiting examples of materials for the outer firm layer include polymeric resins of varying curing layers, acrylic or acrylate material or metal additive printed materials with flexibility and non-traumatic surfaces. Non-limiting examples of materials for the flexible material for the sides include polymeric resins of varying curing layers, acrylate or thicker but softer dental resins. The coil springs, elastomeric material and air cushion form the bulk of the cushion structure, the titanium or other metal additive materials create the firmness and body while the side soft walls prevent excessive rigidity during impact or shock.

The shock absorbance feet can be beneficial to the athlete, soldier, etc. to absorb external shock forces on the jaw or face and precent those forces from being transmitted to the neck, skull, brain, and orbit of the eye. This will help reduce concussion G forces related injury, concussions, orbital blow-out, ocular ruptures, retinal tears, retinal detachment, and whiplash of the neck. Additionally, any shock absorbing feature can provide pressure absorption for Bruxism during sleep. Absorbing G forces (linear and torsional) reduce cerebral edema, hypotension and improve levels of consciousness (post-concussion). All these elements also reduce muscle relaxation associated with concussion which otherwise would cause obstruction of the airway by the jaw and tongue.

System 300 can be used for scheduled timed administration of medication through the mechanisms and devices discussed above, especially for those medications best administered while the user is asleep. When medicaments are being administered by the devices disclosed herein, the controller station 200 or system 300 would identify a physiological problem of the user from data received from the sensors and/or from data received from an external EKG monitoring system or external blood-glucose monitoring system of the user followed by generation of an executable instruction sent to the device's on-board microprocessor through wireless data system (blue tooth or other protocols) with back-up confirmation system for dangerous medications. The back-up may be the user themselves (smart phone or display screen of controller Station 200) or an on-call nurse or ER physician or authorized health care provider or tele-medicine through a smart handheld device or through videography/audio from a camera or video recorder in the mandibular or maxillary housing. Data related to administration of the medication would require a response the following day prompting replacement of discharged pellets or other forms of the medicament, a visit to the health care provider's office, or a tele-medicine visit.

The mandibular repositioning devices disclosed herein with their ability to increase the dimensions of the smallest concentric airway cross-sectional area will be able to be used in the field of pediatrics, adult cardiology, adult pulmonology, adult endocrinology, and metabolism, adult gastro-enterology, adult neurology and sleep, adult rheumatology, adult hematology and oncology, adult ophthalmology, and adult nephrology. In pediatrics, the devices can improve or reduce problems caused by asthma, vasomotor rhinitis, pediatric obstructive sleep apnea, cystic fibrosis, bronchiectasis, tracheomalacia, gastro-esophageal reflux, hiatal hernia, recurrent URI, recurrent tonsillitis, adeno-tonsillar hypertrophy, bruxism, hypoplastic palate retrognathia, ADD/ADHA, childhood obesity, failure to thrive, learning difficulty, depression, epilepsy, headaches, nightmares, night-terrors, sleep-walking nighttime bedwetting, pediatric hypertension, Duchene's Muscular Dystrophy, Becker's Muscular Dystrophy, Spino-muscular atrophy, facio-scapulo-humeral dystrophy, and Marfan's Syndrome. In adults, the devices can improve or reduce problems caused by hypertension, coronary artery disease, congestive heart failure, left ventricular hypertrophy, diastolic dysfunction, right ventricular hypertension, mitral regurgitation, tricuspid regurgitation, aortic regurgitation, aortic stenosis, supra-ventricular tachycardia, ventricular tachycardia, atrial fibrillation, and atrial flutter, premature atherosclerosis, atrial enlargement, ventricular enlargement, asthma, COPD, emphysema, bronchiectasis, pulmonary fibrosis, pulmonary embolism, acute respiratory failure, ventilator weaning program management in ICU or rehabilitation, cardio-pulmonary rehabilitation, aspiration pneumonia, obesity, hypothyroidism, diabetes mellites, hyperclolesterolemia, osteoporosis, gastro-esophageal reflux, esophageal stricture, hiatal hernia, gall bladder disease, gall stones, non-alcoholic steatosis of the liver, non-alcoholic cirrhosis, irritable bowel syndrome, embolic and thrombotic stroke, cerebral hemorrhage due to rupture of aneurysm, cluster headaches, migraines, periodic limb movement disorder of sleep, restless leg syndrome, nightmares, night terrors, REM sleep behavior disorder, dementia, Alzheimer's disease, neurodegenerative disease like Parkinson's, Ley Body disease, chronic or acute inflammatory demyelinating polyneuropathy, seizures, PTSD, myasthenia gravis, fibromyalgia, RA, SLE, Barrett's esophagus, esophageal cancer, secondary polycythemia, myelodysplastic syndrome, glaucoma, retinal vein occlusion, tortuosity of retinal veins, retinal artery disease, retinal detachment, macular degeneration, acute retinal stroke, chronic renal failure, benign and malignant nephrosclerosis, renal artery stenosis, fibromuscular dysplasia of renal artery, and noctuna.

Referring now to FIGS. 57 to 58, Algorithm I and the results for one individual as example are shown. Algorithm I predicts the total anterior vertical mandibular lingual repositioning adjustments for effective use of the mandibular repositioning devices herein with a user during physical activities, such as weight loss, athletics, military, and aerospace activities.

The baseline heart rate is the heart rate at rest for a selected user. The target hear rate is the heart rate that is selected by the user or a professional assisting the user with the physical activity such as a coach, fitness expert, doctor, physical therapist, etc. For example, a heart rate that is less than 70% of the peak heart rate may be desired for fat burning activities and can be used in a weight loss program. The peak heart rate is a variable that is dependent upon the age of the selected user and is not gender specific.

Airflow resistance is determined by setting a fixed length of airway to 10 cm and the air viscosity to 1.81 (typical for normal elevations). An increase in airflow resistance causes an increase in heart rate, respiratory rate, work of breathing, and core body temperature, and affects calorie or energy consumption, water loss through sweat, and evaporation through breathing.

Referring now to FIGS. 59 to 61, Algorithm II and results for one individual as an example are shown. The use of Algorithm II for physical activity monitoring, such as during a sporting activity, is meant to be used to improve the individual's performance, such as work efficiency, lower heart rate, etc. while mitigating risk of deterioration from other indices, such as dehydration, core body temperature, etc.

The actual exercise hear rate is measured during a preselected activity. In one embodiment, the preselected activity is running on a treadmill at 4 miles per hour while at a 5% incline. The change in heart rate is important for determining the progress of the individual at a fitness program or physical activity. Monitoring the incremental increase/decrease in the heart rate with adjustment of TAVMLR or intensity of exercise provides a new method of monitoring an individual. The physical activity can be adjusted for the individual at any given time including adjustment of the TAVMLR for the mandibular repositioning devices disclosed herein to create an optimal size of SMCA for the level of exercise desired at that time.

The respiratory rate is a determinant of the work of breathing, which is dependent on oxygen consumption, demand, and cardio-pulmonary coupling. The faster an individual is breathing, the greater the work being performed and the earlier the individual will be fatigued. It also determines the generation of body heat and amount of water evaporation (dehydration). The minute ventilation (MV) has a proportion relationship to the respiratory rate. However, with increasing respiratory rate there is also increase in dead space ventilation and the proportion of alveolar ventilation for each breath begins to decrease. This creates inefficiency of breathing seen in Table 4 above. Increasing inefficiency of breathing (the greater the respiratory rate) generates greater lactic acidosis which clouds consciousness and decision making, produces easy muscle cramps with deterioration in coordination, and creates higher heart rates. It is very important to keep the minute ventilation (respiratory rate) in a manageable (in a range so as to maintain greatest efficiency of breathing or lowest airflow resistance) range to optimize the individual's work, i.e., minimize effort and maximize performance.

The air pressure or airway pressure is the pressure generated by forceful inhalation and exhalation. It is reflective of the work of breathing but also is a determinant of airway resistance. It may cause the airway to be sucked inward (Bernoulli's effect) during inspiration which decreases the SMCA further and deteriorates performance. An increase in pressure may precipitate exercise induced asthma. The work of breathing, typically, needs to be maintained at <10% of the basal metabolic rate (BMR) for an endurance athlete. Greater values are reflective of greater calorie consumption and may be desirable for weight loss programs. These algorithms help optimization of work of breathing to suit the intended or desired result.

Rising core body temperature can be a source of dehydration and rapid fatigue. It may also generate conditions like heat stroke and all its associated complications like rhabdomyolysis, in endurance athletes. The closer this value is to baseline, the safer for the individual. This value is dependent on heart rate and airway resistance, with the airway resistance being dependent on the size of SMCA. Each heart rate increase of 10 beats per minute increases the core body temperature by 1 °C.

Dehydration is expressed in the Algorithms as milliliters per hour. Many individuals fail to complete an activity because of poor management of dehydration. Dehydration is also a factor in injuries suffered during physical activity. Muscle weakness and cramping and decreasing blood pressure due to decreasing intravascular volume are important complications of dehydration. Water loss is inevitable. Understanding the anticipated volume of water loss and replacing it judiciously is now possible because the algorithms estimate the volume of water loss.

An individual that experiences a decrease in the systolic blood pressure (SBP) with exercise is referred to as a "Dipper." Such a decrease in the SBP is a predictor of cardiovascular risk of myocardial infarction and cardiac arrhythmia. A severe increase in SBP is associated with exercise related cardiac complications like stroke and cardiac arrhythmia. Algorithm II enables the SBP to be monitored, thereby enabling the identification of either fluctuation in the SBP for timely intervention and/or prevention of such complications during physical activity. The double product (DP) output of Algorithm II is the SBP multiplied by the pulse rate. This numerical value is used in stress tests as an index of myocardial oxygen consumption. A safe range for DP is 14,000 to 18,000. DP can be monitored by Algorithm II during physical activity to prevent severe increases and decreases in cardiac oxygen consumption. For Dippers, the Algorithms provide a TAVMLR value that when implemented in a mandibular repositioning device that is worn during physical activity can result in a healthy increase in SBP while reducing the heart rate using better provision of oxygen through an increased SMCA, thus keeping the DP within a safe range. Target Peak SBP=1.2*Resting SBP and the same goes for target DBP. In a Dipper, Target Peak SBP=0.8*Resting SBP. The multiplier 1.2 represents a 20% increase in SBP that occurs in normal individuals while the multiplier 0.8 represents the 20% drop in SBP from resting value.

Methods that include the algorithms are numerous. The method can determine the SMCA without requiring a CT Cone Scan of an individual's airway, can determine the TAVMLR to manufacture a customized mandibular repositioning device of the kinds disclosed herein to improve an individual's performance during physical activity, can determine and/or prevent a risk of a cardiac event during exercise, can build fitness programs to fulfill or satisfy a large range of variables and individual needs, can set incremental targets for any of the variables in either algorithm to increase physical performance, such as speed, endurance, ability to jump higher or longer, swim faster, can set incremental targets for any of the variables to reduce the TAVMLR in order to purposefully increase airway resistance to build greater endurance or decrease/increase airflow resistance to mimic conditions of extremely high or low G forces in space or in a military or civilian aircraft during distress, can predict target outcomes and set nutritional supplementation and hydration levels to maximize the success of such targets, can protect athletes and individuals from medical conditions like asthma, unsafe high or low levels of SBP or DBP, can be used in medical practice to adjust the TAVMLR to ease breathing or optimize cardiac performance in conditions like, but not limited to, cystic fibrosis, bronchiectasis, COPD and CHF, Angina, or to treat obesity or diabetes.

The methods include determining baseline parameters for a selected individual, the baseline parameters comprising age, baseline heart rate, respiratory rate, core body temperature, and minute ventilation while at rest, determining the air pressure for an exercise location of the individual, selecting a target heart rate for a preselected physical activity, and calculating the total anterior and vertical mandibular lingual repositioning (TAVMLR) for a mandibular repositioning device using one or more of Algorithms I and II. In one embodiment, the TAVMLR is calculated according to the equation:

$$TAVMLR = 0.1839 * \Big(3.142 * \big((8 * V_a * L_{aairway}) / ((\text{target heart rate} - \text{baseline heart rate})/(\text{the air pressure} * 100))\big)^{1/4}\Big)^2\Big)$$

wherein $V_a$ is the viscosity of air=1.81 and $L_{airway}$ is the length of the airway=10 cm. The TAVMLR value determines the amount of anterior repositioning and vertical repositioning to include in the mandibular repositioning device of the selected user for an at rest position of the mandible.

For Algorithm II, the method includes measuring the individual's actual exercise heart rate at a preselected activity and intensity. In one embodiment, the preselected activity and intensity is a run on a treadmill at 4 miles per hour at a 5% incline. In another embodiment, it is a brisk walk on the treadmill instead of a run. In another embodiment, it may be a brisk walk at 5 miles per hour at an 8% incline. The duration of the preselected activity may very as part of the intensity, such as being for a half hour or 45 minutes, whatever the overseer of the physical activity deems appropriate for the individual to establish an exercise heart rate that fits the ultimate goal of the method.

The methods can include reviewing the output parameters of Algorithm II for any outputs that are outside of a desired range for the individual or for making intensity adjustments to the physical activity for the individual to prevent injury, medical emergencies, etc., and gradual changes in intensity (increases in particular) can be projected and implemented. For example, the double product is outside of the range of 14,000 to 18,000, the blood pressure is too high or too low for the individual, the heart rate is too high for fat burning exercise, etc.

In one embodiment, the individual has their blood pressure monitored while exercising for continual live updating of the Algorithms, especially Algorithm II. The live updating can be accomplished with a mobile device, computer, or other screen capable of displaying the data generated by the algorithms. If the individual is one whose systolic blood pressure (SBP) drops with exercise, e.g., SBP changes from 160 mm Hg to 128 mm Hg, the overseer of the exercise/physical activity can monitor this in real time and can terminate the exercise or reduce the intensity as needed. Software can connect the biometric parameters with the exercise equipment and even control the exercise parameters on the associated equipment (like treadmill or a stationary bicycle) such as slowing or speeding up the treadmill in response to the algorithm. The overseer of the physical activity may even create exercise scenarios to push the physiologic parameter outside of the normal range to increase the endurance or tolerance during physical activity of the individual for example so as to create conditions of severe stress in order to condition the individual to be properly conditioned for the physical activities demands. The individual as mentioned before can be an athlete, military personnel, astronaut, pilot, etc.

Moreover, the overseer can adjust the variables INPUT or OUTPUT in the Algorithms as needed to tailor suitable exercise conditions for individuals with pre-existing conditions. Some example conditions include, but are not limited to, asthma, COPD, cardiac arrhythmia, and excessive sweating syndrome. For example, if the individual has Asthma, the Desired Air Pressure can be selected to stay under 1.32 because expiratory airway pressure rises with intensity of exercise can precipitate an attack of exercise induced asthma. In this example, we still want the Target % Peak HR to stay close to 55-60%. Using the Goal Seek tool in the Excel program, we set the Target Airway Pressure to 1.32 and the algorithm then creates the scenario for safe athletic training at 1.32.

Working Example 1

The inventor has a mandibular reposition device fitted for his oral cavity that has a plateau included at the base of the protrusive flange. The mouth opening calculation for his device is: 23 mm mouth opening (14 degrees opening) set at a zero mm Anterior Advancement, 23 mm Vertical Advancement for a 17.5 Total AVMLR Advancement according to the table that is FIG. 32. The device was designed to treat severe sleep apnea.

The device was worn during physical exercise at the gym with a personal trainer rowing machine. On the rowing machine, the inventor's maximum was 1820 RPMs with a sustained RPM of 1600 over 4 weeks of training. In the first session with the mandibular repositioning device, he reached a maximum of 1910 RPMs and sustained 1880 RPMs while rowing with maximum heart rates ranging between 145-165 beats per minute and being able to recover to 112 beats per minute in 1 minute and 106 beats per minute at the end of 3 minutes. Better results were achieved in strength and number of repetitions as well as reduced recovery time between sets on weight training exercises. Simply put, an increased volume of air went into the lungs, increased ease, and complete expiration of air out of the lungs occurred, and an overall reduced effort to breath was experienced.

Over a period of 12 weeks following the initial 4 weeks of observations, the inventor was able to reach a maximum rowing rate of 2020 RPM, sustained rate of 1940 RPM. The inventor lost 6 lbs. of weight in the same period of time reaching a value of 187 lbs. This weight loss was in excess of weight loss incurred previous to use of this device (weight loss having reached a plateau of 193 lbs.). There was an incremental decline in maximum heart rate that was observed with incremental increase in level of physical exertion. The observed maximum heart rates range was 124-146 beats per minute being able to recover to 98 beats per minute at the end of 1 minute and to 92 beats per minute at the end of 3 minutes.

Working Example 2

Part A

Referring to FIG. 60, INPUT data for an individual of age 56 that weighed 185 lbs and is 67 inches tall was entered into Algorithm I to determine the TAVMLR (total anterior vertical mandibular lingual repositioning) needed for the individual. The INPUTS were: target heart rate 117, baseline heart rate of 60, baseline respiratory rate 12, core body temperature of 98.4 °F, baseline minute ventilation of 12, and a baseline air pressure of 1.69. The calculated TAVMLR value is 8.9. This TAVMLR value is then looked up in the chart in FIG. 30 to determine the anterior advancement and the degrees of mouth opening needed during exercise with the mouth in the at rest position. This correlates to a 4 mm anterior advancement and 4 degrees of mouth opening, which can be accomplished by a plateau having a preselected height of about 4.24 mm and the appropriate mating curvatures of the protrusive flange and driver flange. Additionally, the individual will need to hydrate at a rate of about 277 ml/hr because they are going to lose at least this amount through breathing and sweating (provided ambient room temperature is 70 °F). She/He should expect core body temp to rise to 110 °F, a respiratory rate=23 breaths per minute. AVMLRD that can achieve a SMCA radius of 4.17 mm will dial in TAVMLR=8.9 (predicted SMCA=54.86 sq mm), given a baseline airway SMCA=46.55 sq mm. The baseline airway SMCA for this individual, a sufferer of sleep apnea without a mandibular repositioning device to increase the SMCA, can be determined using a CT Cone Scanner or Algorithm I.

Keeping the above variables constant, employing Algorithm II adds peak Actual Exercise HR (give a predicted existing SMCA) of 137 beats per minute (BPM) that was observed while the individual exercised during a dry run. A dry run is exercise at a given intensity of 4 MPH on a treadmill at 5% incline in this example. This provides additional information like Target v/s Actual % peak HR, Target v/s Actual (patient's) SMCA, Target v/s Actual Work of Breathing. The data for Algorithm II is found in the bottom table of FIG. 60. Here, differences between the change in physiology and airway SMCA are made possible. The individual's actual SMCA is predicted to be 47.20 $mm^2$. Previously, an actual SMCA was only determined by insertion of a Cone CT Scanner into the individual's mouth/throat in a CT scan department of a hospital.

The natural SMCA creates a workload that yields a peak heart rate of 137 BPM during the dry run while the individual exercises at the given intensity of 4 MPH on a treadmill at 5% incline. The Algorithm II calculates a Target SMCA of 54.86 $mm^2$ to produce the Target HR of 117 BPM and recommends using an AVMLRD with TAVMLR=9 mm to get there, given all other input variables held constant. This level of detail helps the expert overseeing the physical activity to tailor the needs of the individual or the desired weight loss program and the various steps and time required to achieve successful outcomes.

If the individual is already using a mandibular repositioning device disclosed herein with a certain TAVMLR to yield the actual results in Algorithm II, then the overseer can see the change in TAVMLR that will be needed to get the Target Exercise HR and other physiological outcomes. This may be accomplished by changing flanges if the individual has a kit with a plurality of removably replaceable flanges or by having a new mandibular repositioning device made for the individual.

Part B

The individual in this example gains 15 pounds which changes the baseline heart rate to 45 BPM, a respiratory rate to 20 and the minute ventilation to 10. This is reflected in the Table in FIG. 61. The air pressure on the day of the test was 1.6 atm. Because of the weight gain, the overseer has determined a target heart rate of 100 beats per minute during physical activity. Algorithm I indicates a TAVMLR of 10.9 (rounded to 11) is needed to open the airway for an SMCA of 65.49 $mm^2$.

The individual should hydrate at a rate of 275 ml/hr or more. Algorithm II indicates that the individual can have a fat burning (weight loss) exercise by exercising while maintaining their hear rate at a level of 61% of the Peak Heart Rate. This individual's baseline SMCA is 46.55 $mm^2$, so to achieve the heart rate necessary for fat burning exercise, they need a mandibular repositioning device as disclosed herein with a TAVMLR=9-11 to bring the SMCA to about 65.49 $mm^2$. This individual's double product number is 19200, which is an indication of excessive oxygen consumption by the heart. This is higher than the normal range of 14000-18000. The overseer can use this information to implement a lower exercise intensity to keep the systolic blood pressure from elevating unreasonably to safely continue a fat burning exercise program until the individual's physician can treat the high blood pressure. The overseer can use Algorithm II to input a desired double product number, such as 17000, and apply the Gool Seek tool in the Excel Program to reverse the calculations based on this preselected value for what is typically an OUTPUT. The values from the Algorithm II will indicate a new TAVMLR and dehydration values and a new level of % of Peak Heart Rate for the exercise program to continue.

It should be noted that the embodiments are not limited in their application or use to the details of construction and arrangement of parts and steps illustrated in the drawings and description. Features of the illustrative embodiments, constructions, and variants may be implemented or incorporated in other embodiments, constructions, variants, and modifications, and may be practiced or carried out in various ways. Furthermore, unless otherwise indicated, the terms and expressions employed herein have been chosen for the purpose of describing the illustrative embodiments of the present invention for the convenience of the reader and are not for the purpose of limiting the invention. Having described the invention in detail and by reference to preferred embodiments thereof, it will be apparent that modifications and variations are possible without departing from the scope of the invention which is defined in the appended claims.

What is claimed is:

1. A mandibular repositioning device comprising:

a maxillary piece comprising a tooth covering having a right side backmost teeth mold and/or a left side backmost teeth mold and a driver flange protruding laterally outward on either or both of the right side and left side backmost teeth mold, the driver flange having an anterior side with a non-arcuate straight surface; and a mandibular piece comprising:

a tooth covering having a protrusive flange extending cranially therefrom positioned to have a posterior side engaged with the anterior side of the driver flange, the posterior side of the protrusive flange has a non-arcuate straight posterior surface that engages the non-arcuate straight surface of the driver flange in a rest position; and a plateau of a preselected height between the base of the protrusive flange and the tooth covering, wherein the preselected height is set to prevent disconnect between the protrusive flange and the driver flange relative to a fully open mouth measurement between incisors of the user;

wherein the posterior side of the protrusive flange and the anterior side of the driver flange have a posterior lean in a respective vertical axis to define an angle $\theta_1$.

2. The mandibular repositioning device of claim 1, wherein the maxillary piece has a housing configured proximate one or both of a left molar portion and a right molar portion, wherein the housing encloses a power source electrically connected to a motor and to an on-board circuit board and has a driver operatively connected to the motor and to the driver flange for anterior and posterior movements of the driver flange and/or cranial and caudal movements of the driver flange.

3. The mandibular repositioning device of claim 2, wherein the mandibular piece has a housing configured proximate one or both of a left molar portion and a right molar portion and the mandibular device has a laterally inward extending protrusion extending from the housing toward a tongue at a position proximate a lingual muscle of the tongue, wherein the housing of the mandibular piece encloses a power source electrically connected to an on-board circuit board which is in electrical communication with one or more sensors enclosed within the laterally inward extending protrusion, or the maxillary piece has a palate housing portion and/or a buccal housing portion extending from the housing thereof and the palate housing portion and buccal housing portion encloses therein a power source electrically connected to an on-board circuit board which is in electrical communication with one or more sensors.

4. The mandibular repositioning device of claim 3, wherein the mandibular piece houses the one or more sensors, and the on-board circuit within housings of the maxillary piece include a receiver and a microprocessor having an instruction stored in nontransitory memory to activate the motor and the on-board circuit board within housings of the mandibular piece include a receiver, a transmitter, and a microprocessor having an instruction in nontransitory memory to activate the motor within housing of the maxillary piece simultaneously based on data received from the one or more sensors, and, when the maxillary piece houses the one or more sensors, the on-board circuit within the housings of the maxillary piece include a microprocessor having an instruction in nontransitory memory to activate the motor within housings of the mandibular piece and housings of the maxillary piece simultaneously based on data received from the one or more sensors.

5. The mandibular repositioning device of claim 4, wherein the maxillary piece only has anterior to posterior movement of the driver flange, and the mandibular piece has a motor housed within the housing thereof and has a cranial-to-caudal driver operatively connected to the motor; wherein the cranial-to-caudal driver is operatively engaged with the maxillary piece for cranial and caudal adjustment of the device from instructions stored in the nontransitory memory of the on-board circuit board within the housing of the mandibular piece based on data received from the one or more sensors.

6. The mandibular repositioning device of claim 4, wherein one or both of the laterally inward extending protrusion house an electrode operatively connected to the on-board circuit board and the power source of the housing from which laterally inward extending protrusion extends; wherein the on-board circuit board within the housings of the mandibular piece include instructions that based on data from the one or more sensors activates the motor within housing of the maxillary piece and the electrode simultaneously or sequentially as needed to open an airway of a user.

7. The mandibular repositioning device of claim 1, wherein the maxillary piece has a housing configured proximate one or both of a left molar portion and a right molar portion, wherein the housing encloses a power source electrically connected to a motor and to a microprocessor and has a driver operatively connected to a means for moving the driver flange for anterior-posterior movement and cranial-caudal movement.

8. The mandibular repositioning device of claim 7, wherein the means for moving the driver flange comprises a piezo-electric motor and an internal robotic armature positioned for repositioning of the piezo-electric motor as a cranial-caudal movement, or robotic arms connected to integrated plates in the driver flange, or robotic arms connected to separate plates for the independent cranial-caudal movement and anterior-posterior movement of the driver flange.

9. The mandibular repositioning device of claim 8, wherein the microprocessor comprises a quantum microchiplet and/or a photonic integrated circuit.

10. The mandibular repositioning device of claim 9, comprising position sensors measuring a first distance for cranial-caudal movement and a second distance for anterior-posterior movement of the driver flange.

11. The mandibular repositioning device of claim 1, wherein the plateau is wedge-shaped, has a first height at an anterior base of the protrusive flange, a second height at a posterior base of the protrusive flange, and the first height is greater than the second height; and wherein the protrusive flange and driver flange are inclined equivalently to the plateau to maintain engagement of the non-arcuate straight posterior surface and the non-arcuate straight surface thereof.

12. The mandibular repositioning device of claim 11, wherein the plateau extends posteriorly to a posterior terminus of the tooth covering and terminates with a third height that is smaller than the first height and the second height.

13. The mandibular repositioning device of claim 1, wherein the driver flange is removably replaceably attached to the maxillary piece.

14. The mandibular repositioning device of claim 13, wherein the protrusive flange slides into the tooth covering of the mandibular piece from a rear surface and is configured to engagingly saddle a dental crown against cranial movement.

15. The mandibular repositioning device of claim 1, wherein the plateau extends across a full width of the tooth covering.

16. The mandibular repositioning device of claim 1, wherein the protrusive flange is removably replaceably attached to the mandibular piece.

17. The mandibular repositioning device of claim 1, wherein the mandibular piece has a housing proximate one or both of a left molar portion and a right molar portion and the mandibular device has a laterally inward extending protrusion extending from the housing toward a tongue at a position proximate a lingual muscle of the tongue, wherein the housing of the mandibular piece encloses a power source electrically connected to an on-board circuit board which is in electrical communication with one or more sensors and with an electrode, and wherein the on-board circuit board within the housings include instructions that based on data from the one or more sensors activates the electrode as needed to open an airway of a user.

18. The mandibular repositioning device of claim 1, wherein $\theta_1$ is an angle in a range of 1 to 15 degrees.

19. The mandibular repositioning device of claim 1, wherein $\theta_1$ is an angle in a range of 5 to 14 degrees.

20. The mandibular repositioning device of claim 1, wherein $\theta_1$ defines the amount of protrusion of the mandible with each degree of mouth opening.

* * * * *